(12) United States Patent
Gallego et al.

(10) Patent No.: US 7,763,615 B2
(45) Date of Patent: Jul. 27, 2010

(54) ECTEINASCIDIN ANALOGS FOR USE AS ANTITUMOUR AGENTS

(75) Inventors: Pilar Gallego, Madrid (ES); Carmen Cuevas, Madrid (ES); Simon Munt, Madrid (ES); Ignacio Manzanares, Madrid (ES); Valentin Martinez, Madrid (ES)

(73) Assignee: Pharma Mar, S.A., Madrid (ES)

( * ) Notice: Subject to any disclaimer, the term of this patent is extended or adjusted under 35 U.S.C. 154(b) by 860 days.

(21) Appl. No.: 10/485,536

(22) PCT Filed: Aug. 6, 2002
(Under 37 CFR 1.47)

(86) PCT No.: PCT/GB02/03592

§ 371 (c)(1),
(2), (4) Date: May 18, 2005

(87) PCT Pub. No.: WO03/014127

PCT Pub. Date: Feb. 20, 2003

(65) Prior Publication Data

US 2006/0128711 A1    Jun. 15, 2006

(30) Foreign Application Priority Data

Aug. 7, 2001   (GB) .................... 0119243.4

(51) Int. Cl.
| | | |
|---|---|---|
| A01N 43/58 | (2006.01) | |
| A01N 43/60 | (2006.01) | |
| A61K 31/50 | (2006.01) | |
| A61K 31/495 | (2006.01) | |
| C07D 487/00 | (2006.01) | |
| C07D 491/00 | (2006.01) | |
| C07D 513/00 | (2006.01) | |

(52) U.S. Cl. ...................... 514/249; 540/468
(58) Field of Classification Search ................ None
See application file for complete search history.

(56) References Cited

U.S. PATENT DOCUMENTS

| 5,089,273 A | | 2/1992 | Rinehart et al. | |
|---|---|---|---|---|
| 5,149,804 A | * | 9/1992 | Rinehart et al. | 540/466 |
| 5,256,663 A | * | 10/1993 | Rinehart et al. | 514/250 |
| 5,478,932 A | * | 12/1995 | Rinehart et al. | 540/466 |
| 5,654,426 A | | 8/1997 | Rinehart et al. | |
| 5,721,362 A | | 2/1998 | Corey et al. | |
| 5,985,876 A | | 11/1999 | Rinehart et al. | |
| 6,124,292 A | | 9/2000 | Corey | |
| 6,124,293 A | | 9/2000 | Rinehart et al. | |
| 6,316,214 B1 | | 11/2001 | Rinehart et al. | |
| 6,348,467 B1 | | 2/2002 | Corey | |
| 6,686,470 B2 | | 2/2004 | Danishefsky et al. | |
| 6,867,334 B2 | | 3/2005 | Rinehart et al. | |
| 2003/0216397 A1 | | 11/2003 | Flores et al. | |
| 2004/0019056 A1 | | 1/2004 | Manzanares et al. | |

FOREIGN PATENT DOCUMENTS

| EP | 0 309 477 B1 | 11/1991 |
|---|---|---|
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/51238 | 10/1999 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |

OTHER PUBLICATIONS

Sakai, et. al., Proceedings of the National Academy of Sciences of the United States of America (1992), 89(23), 11456-60.*

(Continued)

*Primary Examiner*—James O Wilson
*Assistant Examiner*—Jeffrey H Murray
(74) *Attorney, Agent, or Firm*—Kenneth H. Sonnenfeld; King & Spalding LLP

(57) ABSTRACT

Derivatives of ecteinascidin 736 of general formula (I) wherein the groups $R_1$, $R_2$, $R_3$, $R_4$ and $R_5$ are each independently selected from the group consisting of H, OH, OR', SH, SR', SOR', $SO_2R'$, C(=O)R', C(=O)OR', $NO_2$, $NH_2$, NHR', $N(R')_2$, NHC(O)R', CN, halogen, =O, substituted or unsubstituted $C_1$-$C_{25}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heterocyclic; wherein X is independently selected of OR', CN, (=O), or H; wherein each of the R' groups is independently selected from the group consisting of H, OH, $NO_2$, $NH_2$, SH, CN, halogen, =O, C(=O)H, $C(=O)CH_3$, $CO_2H$, substituted or unsubstituted $C_1$-$C_{25}$ alkyl, substituted or unsubstituted $C_2$-$C_{18}$ alkenyl, substituted or unsubstituted $C_2$-$C_{18}$ alkynyl, substituted or unsubstituted aryl; wherein m is 0, 1 or 2; and wherein n is 0, 1, 2, 3, or 4, and their use as antitumoral agent.

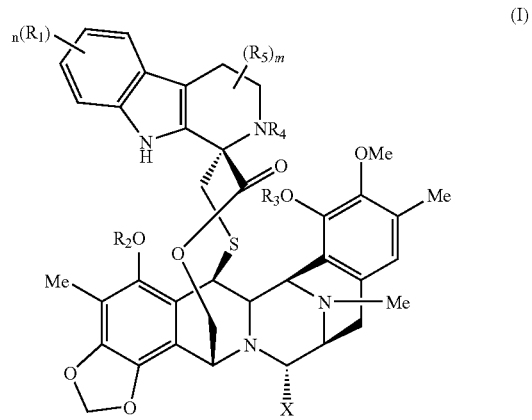

32 Claims, No Drawings

OTHER PUBLICATIONS

Cecil Textbook of Medicine, 21st Edition (2000), Goldman & Bennett (Editors), W.B. Saunders Company (Publisher), Chapter 198, pp. 1060-1074.*
Internal Medicine, 4th Edition, Editor-in-Chief Jay Stein, (1994); Chapters 71-72, pp. 699-715.*
Dorwald F. A. Side Reactions in Organic Synthesis, 2005, Wiley: VCH, Weinheim p. IX of Preface.*
Arai, T. et al., "The Structure of a Novel Antitumor Antibiotic, Saframycin A", *Experientia*, vol. 36, pp. 1025-1027 (1980).
Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).
Arai, Tadashi et al., "Increased Production of Saframycin A and Isolation of Saframycin S", *The Jounral of Antibiotics*, vol. XXXIII, No. 9, pp. 951-960 (1980).
Arai, Tadashi et al., "Isoquinolineinones from Actinomycetes and Sponges", *The Alkaloids Chemistry and Pharmacology*, vol. XXI, pp. 56-100 (1983).
Arai, Tadashi et al., "New Antibiotics, Safraycins A, B, C, D and E", *The Journal of Antibiotics*, vol. XXX, No. 11, pp. 1015-1018 (1977).
Asaoka, Takemitsu et al., "A New Saframycin, Saframycin R", *The Journal of Antibiotics*, vol. XXXV, No. 12, pp. 1708-1710 (1982).
Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).
Brown, J.M., "NCI's Anticancer Drug Screening Program May Not Be Selecting for Clinically Active Compounds," Oncol. Res. 9(5):213-215 (1997).
Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).
Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).
Corey, E.J. et al., "Enantioselective Total Synthesis of Ecteinascidin 743", *Journal of the American Chemical Society*, vol. 118, No. 38, pp. 9202-9203 (1996).
Cuevas, Carmen et al., "Synthesis of Ecteinascidin ET-743 and Phthalascidin Pt-650 from Cyanosafracin B", *Organic Letters*, vol. 2, No. 16, pp. 2545-2548 (2000).
Draetta, G. and Pagano, M., "Annual Reports in Medicinal Chemistry, vol. 31," Academic Press, San Diego, pp. 241-246 (1996).
Eckhardt, S.G. et al., "Activity of ecteinascidin, a novel marine cytotoxic, against primary human tumor colony-forming units", *Proceedings of the American Association for Cancer Research*, vol. 37, #2791, pp. 409 (1996).
Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).
Flam, Faye, "Chemical Prospectors Scour the Seas for Promising Drugs", *Science*, vol. 266, pp. 1324-1325 (1994).
Frincke, James M. et al., "Antimicrobial Metabolites of the Sponge *Reniera* sp.", *Journal of the American Chemical Society*, vol. 104, pp. 265-269 (1982).
Fukuyama, Tohru et al., "Stereocontrolled Total Synthesis of (±)-Saframycin B", *Journal of American Chemical Society*, vol. 104, pp. 4957-4958 (1982).
Fukuyama, Tohru et al., "Total Synthesis of (±)-Saframycin A", *Journal of American Chemical Society*, vol. 112, pp. 3712-3713 (1990).
Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).
Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).
Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).
He, Hai-yin et al., "Renieramycins E and F from the Sponge *Reniera* sp.: Reassignment of the Stereochemistry of the Renieramycins", *The Journal of Organic Chemistry*, vol. 54, No. 24, pp. 5822-5824 (1989).
Hendriks, H.R. et al., "High antitumor activity of ET743 in human tumor xenograft models", *Proceedings of the American Association for Cancer Research*, vol. 37, #2653, pp. 389 (1996).
Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).
Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).
Ito, Yoichiro, "High-Speed Countercurrent Chromatography", *Critical Reviews in Analytical Chemistry*, vol. 17, No. 1, pp. 65-143 (1986).
Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).
Kofron, William G. et al., "A Convenient Method for Estimation of Alkyllithium Concentrations", *The Journal of Organic Chemistry*, vol. 41, No. 10, pp. 1879-1880 (1976).
Kubo, Akinori et al., "Structure of Saframycin D, A New Dimeric Isoquinolinequinone Antibiotic", *Chem. Pharm. Bull.*, vol. 35, No. 1, pp. 440-442 (1987).
Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).
Lichter, W. et al., "Biological Activities Exerted by Extracts of Ecteinascidia Turbinata", *Food and Drugs from the Sea Proceedings*, pp. 117-127 (1972).
Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).
Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).
Martinez et al., "A New, More Efficient, and Effective Process for the Synthesis of a Key Pentacyclic Intermediate for Production of Ecteinascidin and Phthalascidin Antitumor Agents", *Organic Letters*, 2(7):993-996 (2000).
Martinez et al., "Enantioselective Synthesis of Saframycin A and Evaluation of Antitumor Activity Relative to Ecteinascidin/Saframycin Hybirds", *Organic Letters*, 1(7):75-77 (1999).
Martinez, Eduardo J. et al., "Phthalascidin, a synthetic antitumor agent with potency and mode of action comparable to ecteinascidin 743", *Chemistry*, vol. 96, pp. 3496-3501 (1999).
Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).
Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).
Moore, B.M. et al., "The NMR model of an ecteinascidin 743-DNA adduct", *Proceedings of the American Association for Cancer Research*, vol. 38, #2105, pp. 314 (1997).
Myers et al., "A Concise, Stereocontrolled Syntheis of (-)-Saframycin A by the Directed Condensation of α-Amino Aldehyde Precursors", *J. Am. Chem. Soc.*, 121:10828-10829 (1999).

Nakagawa, Masako et al., "Total Synthesis of (−)-Eudistomin L and (−)-Debromoeudistomin L", *Journal of the American Chemical Society*, vol. 111, No. 7, pp. 2721-2722 (1989).

Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).

Remers, William A., "Saframycins, Renieramycins, and Safracins", *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Bioactive Compounds from Aquatic and Terrestrial Sources", *Journal of Natural Products*, vol. 53, No. 4, pp. 771-792 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Ecteinascidins 729, 743, 759A, 759B, and 770: Potent Antitumor Agents from the Caribbean Tunicate Exteinascidia Turbinata", *The Journal of Organic Chemistry*, vol. 55, No. 15, pp. 4512-4515 (1990).

Rinehart, Kenneth L., "Antitumor Compounds from Tunicates", *Medicinal Research Reviews*, vol. 20, No. 1, pp. 1-27 (2000).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Shamma, Maurice et al., *Carbon-13 NMR Shift Assignments of Amines and Alkaloids*, pp. 206 (1979).

Still, W. Clark et al., "Rapid Chromatographic Technique for Preparative Separations with Moderate Resolution", *Journal of Organic Chemistry*, vol. 43, No. 14, pp. 2923-2925 (1978).

Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Takahaski, Katsuhiro, "New Antibiotics, Saframycins A, B, C, D and E", *The Journal of Antibiotics*, vol. XXX, No. 11, pp. 1015-1018 (1977).

Trowitzsch-Kienast, Wolfram et al., "Isolierung und Strukturauflclarung der Saframycine Mx 1 und Mx 2, neue antitumor-aktive Antibiotika aus Myxococcus xanthus", *Liebigs Ann. Chem.*, vol. XXXV, pp. 475-481 (1988).

Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).

Calabresi et al., "Chemotherapy of Neoplastic Diseases", Goodman & Gilman's The Pharmacological Basis of Therapeutics, 9th ed. New York: McGraw-Hill, 1996, pp. 1225-1229.

"Cancer" definition, http://www.medterms.com/script/main/art.asp?articlekey+2580, accessed Nov. 27, 2007.

Cecil Textbook of Medicine (Bennet, J.C. and Plum, F., eds.) 20th Edition, vol. 1, pp. 1004-1010 (1996).

Cecil Textbook of Medicine (Goldman & Bennett, eds.) 21st Edition, Chapter 198, 2000, pp. 1060-1074.

Fregeau, Nancy Louise, "Biologically Active Compounds froma Clam and a Tunicate", Thesis, University of Illinois art Urbana-Champaign, 1992.

Greene et al., Protective Groups in Organic Systems, 1999, Table of Contents for Chapters 2 and 7.

Internal Medicine, 4th Edition, Editor-in-Chief Jay Stein, Chapters 71-72, 1994, pp. 699-715.

"IUPAC Gold Book", http://goldbook.iupac.org/A00123.html, accessed Dec. 26, 2007.

Holt, Tom Grady, "The Isolation and Structural Characterization of the Ecteinascidins", Thesis, University of Illinois art Urbana-Champaign, 1986.

Kania, "The first Enantioselective Total Synthesis of Dolabellatrienone and Ecteinascidin 743", Harvard University, Sep. 1997, pp. 1-225.

Morales, Jose Javier, "Marine Natural Products Chemistry of a Caribbean Tunicate and a Palau Sponge", University of Illinois art Urbana-Champaign, 1999.

Sakai, Ryuichi, "Biologically Active Compounds from Tunicates and a Sponge", Thesis, University of Illinois art Urbana-Champaign, 1991.

Valoti et al. Clin. Cancer Res. 4(8): 1977-83 (1998).

Wright, Amy E. et al., "Antitumor Tetrahydroisoquinoline Alkaloids from the Colonial Ascidian Ecteinascidia Turbinata", *The Journal of Organic Chemistry*, vol. 55, No. 15, pp. 4508-4512 (1990).

Yazawa, Katsukiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).

Zmijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

Cecil Textbook of Medicine, 21st Edition (2000), Goldman & Bennett (Editors), W.B. Saunders Company (Publisher), Chapter 198, pp. 1060-1074.

Sparidans Rolf W. et al., "Search for metabolites of ecteinascidin 743, a novel, marine-derived anti-cancer agent, in man." *Anti-Cancer Drugs*, vol. 12, pp. 653-666, 2001.

Internal Medicine, 4th Edition, Editor-in-Chief Jay Stein, Chapters 71-72, pp. 699-729, 1994.

Parulekar, A.H. et al., "Bioactivity and Chemical Ecology of Some Interdial Animals" *Bioactivity and Chemical Ecology*, pp. 29-35, 1991.

\* cited by examiner

ECTEINASCIDIN ANALOGS FOR USE AS ANTITUMOUR AGENTS

The present invention relates to derivatives of the ecteinascidins, particularly ecteinascidin 736 (ET-736), pharmaceutical compositions containing them and their use as antitumoral compounds.

BACKGROUND OF THE INVENTION

The ecteinascidins are exceedingly potent antitumour agents isolated from the marine tunicate *Ecteinascidia turbinata*. Several ecteinascidins have been reported previously in the patent and scientific literature. See, for example:

U.S. Pat. No. 5,256,663, which describes pharmaceutical compositions comprising matter extracted from the tropical marine invertebrate, *Ecteinascidia turbinata*, and designated therein as ecteinascidins, and the use of such compositions as antibacterial, anti-viral, and/or antitumour agents in mammals.

U.S. Pat. No. 5,089,273, which describes novel compositions of matter extracted from the tropical marine invertebrate, *Ecteinascidia turbinata*, and designated therein as ecteinascidins 729, 743, 745, 759A, 759B and 770. These compounds are useful as antibacterial and/or antitumour agents in mammals.

U.S. Pat. No. 5,149,804 which describes Ecteinascidins 722 and 736 (Et's 722 and 736) isolated from the Caribbean tunicate *Ecteinascidia turbinata* and their structures. Et's 722 and 736 protect mice in vivo at very low concentrations against P388 lymphoma, B16 melanoma, and Lewis lung carcinoma.

U.S. Pat. No. 5,478,932, which describes ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,654,426, which describes several ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,721,362 which describes a synthetic process for the formation of ecteinascidin compounds and related structures.

U.S. Pat. No. 6,124,292 which describes a series of new ecteinascidin-like compounds.

WO 0177115, WO 0187894 and WO 0187895, which describe new synthetic compounds of the ecteinascidin series, their synthesis and biological properties.

See also: Corey, E. J., *J. Am. Chem. Soc.*, 1996, 118 pp. 9202-9203; Rinehart, et al., *Journal of Natural Products*, 1990, "Bioactive Compounds from Aquatic and Terrestrial Sources", vol. 53, pp. 771-792; Rinehart et al., *Pure and Appl. Chem.*, 1990, "Biologically active natural products", vol 62, pp. 1277-1280; Rinehart, et al., *J. Org. Chem.*, 1990, "Ecteinascidins 729, 743, 745, 759A, 759B, and 770: potent Antitumour Agents from the Caribbean Tunicate *Ecteinascidia turninata*", vol. 55, pp. 4512-4515; Wright et al., *J. Org. Chem.*, 1990, "Antitumour Tetrahydroisoquinoline Alkaloids from the Colonial ascidian *Ecteinascidia turbinata*", vol. 55, pp. 4508-4512; Sakai et al., *Proc. Natl. Acad. Sci. USA* 1992, "Additional anitumor ecteinascidins from a Caribbean tunicate: Crystal structures and activities in vivo", vol. 89, 11456-11460; *Science* 1994, "Chemical Prospectors Scour the Seas for Promising Drugs", vol. 266, pp. 1324; Koenig, K. E., "Asymmetric Synthesis", ed. Morrison, Academic Press, Inc., Orlando, Fla., vol. 5, 1985, p. 71; Barton, et al., *J. Chem Soc. Perkin Trans.*, 1, 1982, "Synthesis and Properties of a Series of Sterically Hindered Guanidine bases", pp. 2085; Fukuyama et al., *J. Am. Chem. Soc.*, 1982, "Stereocontrolled Total Synthesis of (+)-Saframycin B", vol. 104, pp. 4957; Fukuyama et al., *J. Am. Chem. Soc.*, 1990, "Total Synthesis of (+)—Saframycin A", vol. 112, p. 3712; Saito, et al., *J. Org. Chem.*, 1989, "Synthesis of Saframycins. Preparation of a Key tricyclic Lactam Intermediate to Saframycin A", vol. 54, 5391; Still, et al., *J. Org. Chem.*, 1978, "Rapid Chromatographic Technique for Preparative Separations with Moderate Resolution", vol. 43, p. 2923; Kofron, W. G.; Baclawski, L. M., *J. Org. Chem.*, 1976, vol. 41, 1879; Guan et al., *J. Biomolec. Struc. & Dynam.*, vol. 10, pp. 793-817 (1993); Shamma et al., "Carbon-13 NMR Shift Assignments of Amines and Alkaloids", p. 206 (1979); Lown et al., *Biochemistry*, 21, 419-428 (1982); Zmijewski et al., *Chem. Biol. Interactions*, 52, 361-375 (1985); Ito, *CRC Crit. Rev. Anal. Chem.*, 17, 65-143 (1986); Rinehart et al., "Topics in Pharmaceutical Sciences 1989", pp. 613-626, D. D. Breimer, D. J. A. Cromwelin, K. K. Midha, Eds., Amsterdam Medical Press B. V., Noordwijk, The Netherlands (1989); Rinehart et al., "Biological Mass Spectrometry", 233-258 eds. Burlingame et al., Elsevier Amsterdam (1990); Guan et al., *Jour. Biomolec. Struct. & Dynam.*, vol. 10 pp. 793-817, (1993); Nakagawa et al., *J. Amer. Chem. Soc.*, 111: 2721-2722 (1989); Lichter et al., "Food and Drugs from the Sea Proceedings" (1972), Marine Technology Society, Washington, D.C. 1973, 117-127; Sakai et al., *J. Amer. Chem. Soc.*, 1996, 118, 9017; Garcia-Rocha et al., *Brit. J. Cancer*, 1996, 73: 875-883; and pommier et al., *Biochemistry*, 1996, 35: 13303-13309;

In 2000, a hemisynthetic process for the formation of ecteinascidin compounds and related structures such as phthalascidin starting from natural bis(tetrahydroisoquinoline) alkaloids such as the saframycin and safracin antibiotics available from different culture broths was reported; See Manzanares et al., *Org. Lett.*, 2000, "Synthesis of Ecteinascidin ET-743 and Phthalascidin Pt-650 from Cyanosafracin B", Vol. 2, No 16, pp. 2545-2548; and International Patent Application WO 00 69862.

Ecteinascidin 736 was first discovered by Rinehart and features a tetrahydro-β-carboline unit in place of the tetrahydroisoquinoline unit more usually found in the ecteinascidin compounds isolated from natural sources; See for example Sakai et al., *Proc. Natl. Acad. Sci. USA* 1992, "Additional antitumor ecteinascidins from a Caribbean tunicate: Crystal structures and activities in vivo", vol. 89, 11456-11460.

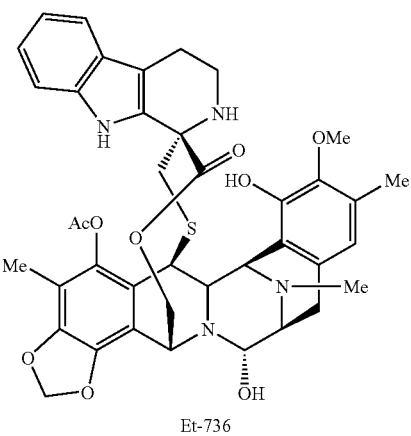

Et-736

WO 9209607 claims ecteinascidin 736, as well as ecteinascidin 722 with hydrogen in place of methyl on the nitrogen common to rings C and D of ecteinascidin 736 and O-methylecteinascidin 736 with methoxy in place of hydroxy on ring C of ecteinascidin 736.

Despite the positive results obtained in clinical applications in chemotherapy, the search in the field of ecteinascidin compounds is still open to the identification of new compounds with optimal features of cytotoxicity and selectivity toward the tumour and with a reduced systemic toxicity and improved pharmacokinetic properties.

SUMMARY OF THE INVENTION

The present invention is directed to compounds of the general formula I:

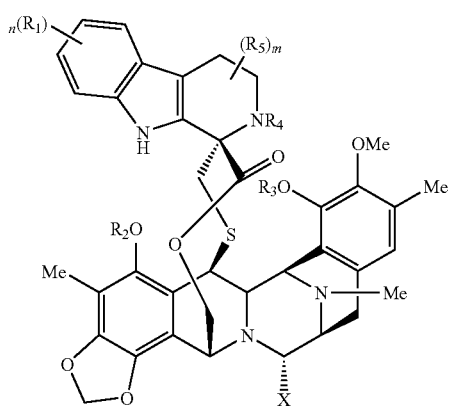

or Ia

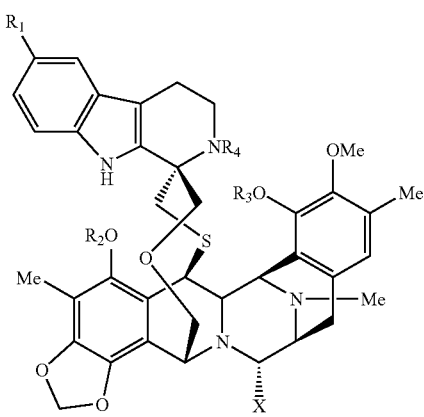

wherein the substituent groups for $R_1$, $R_2$, $R_3$, $R_4$, and $R_5$ are each independently selected from the group consisting of H, OH, OR', SH, SR', SOR', $SO_2R'$, C(=O)R', C(=O)OR', $NO_2$, $NH_2$, NHR', $N(R')_2$, NHC(O)R', CN, halogen, =O, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heterocyclic;

wherein X is independently selected of OR', CN, (=O), or H.

wherein each of the R' groups is independently selected from the group consisting of H, OH, $NO_2$, $NH_2$, SH, CN, halogen, =O, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

wherein m is 0, 1 or 2; and wherein n is 0, 1, 2, 3 or 4.

The present invention also relates to the synthesis of ecteinascidin 736 (where $R_1$, $R_3$, $R_4$, $R_5$=H, $R_2$=CH3CO— and X=OH) and related compounds of the general formula I or Ia.

In another aspect, the invention relates to pharmaceutical compositions comprising a compound of formula I.

In another aspect, the invention relates to the use of compounds of general formula I or Ia in the treatment of cancer.

As one group, the invention provides compounds of formula I or Ia, wherein:

$R_1$ is hydrogen, hydroxy, halogen, alkoxy or aralkyl;

$R_2$ and $R_3$ are independently selected from hydrogen, R', C=OR', or COOR', where R' is optionally substituted alkyl or alkenyl, the optional substituents being chosen from halo, amino including amino derived from amino acid, aryl or heterocyclic;

$R_4$ is hydrogen, alkyl or C(=O)OR', where R' is alkylene.

$R_5$ is hydrogen or alkyl;

X is hydrogen, hydroxy, cyano or keto;

m is 0 or 1; and n is 0 or 1.

Suitable halogen substituents in the compounds of the present invention include F, Cl, Br and I.

Alkyl groups preferably have from 1 to 24 carbon atoms. One more preferred class of alkyl groups has 1 to about 12 carbon atoms, yet more preferably 1 to about 8 carbon atoms, still more preferably 1 to about 6 carbon atoms, and most preferably 1, 2, 3 or 4 carbon atoms. Another more preferred class of alkyl groups has 12 to about 24 carbon atoms, yet more preferably 12 to about 18 carbon atoms, and most preferably 13, 15 or 17 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulphinyl groups in the compounds of the present invention include those groups having one or more sulphoxide (SO) groups and from 1 to about 12 carbon atoms, more preferably from 1 to about 8 carbon atoms, and still more preferably 1 to about 6 carbon atoms. Alkylsulphinyl groups having 1, 2, 3 or 4 carbon atoms are particularly preferred.

Preferred alkylsulphonyl groups in the compounds of the present invention include those groups having one or more sulphonyl ($SO_2$) groups and from 1 to about 12 carbon atoms, more preferably from 1 to about 8 carbon atoms, and still more preferably 1 to about 6 carbon atoms. Alkylsulphonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolidinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2.3-substituted phenyl, 2.5-substituted phenyl, 2.3.5-substituted and 2.4.5-substituted phenyl, including where one or more of the phenyl substituents is an electron-withdrawing group such as halogen, cyano, nitro, alkanoyl, sulphinyl, sulphonyl and the like; naphthyl including 1-naphthyl and 2-naphthyl; biphenyl; phenanthryl; and anthracyl.

References herein to substituted R' groups in the compounds of the present invention refer to the specified moiety, typically alkyl or alkenyl, that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulphinyl groups including those moieties having one or more sulphinyl linkages and from 1 to about 12 carbon atoms or from 1 to about 6 carbon atoms; alkylsulphonyl groups including those moieties having one or more sulphonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms.

Preferred R' groups are present in groups of formula R', COR' or COOR' and include alkyl or alkenyl, that may be substituted at one or more available positions by one or more suitable groups, e.g., halogen such as fluoro, chloro, bromo and iodo, especially ω-chloro or perfluoro; aminoalkyl groups such as groups having one or more N atoms and from 1 to about 12 carbon atoms or from 1 to about 6 carbon atoms, and especially including amino acid, notably glycine, alanine, arginine, asparagine, asparaginic acid, cystein, glutamine, glutamic acid, histidine, isoleucine, leucine, lysine, methionine, phenylalanine, proline, serine, threonine, tryptophan, tyrosine or valine, especially protected forms of such amino acids; carbocylic aryl having 6 or more carbons, particularly phenyl; and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms, the heterocyclic groups optionally being substituted with one or more of the substituents permitted for R' and especially amino such as dimethylamino or with keto.

Without being exhaustive, preferred compounds of this invention have one or more of the following definitions:

$R_1$ is H; hydroxy; halogen, especially F, alkyoxy (alkyl being 1 to 7 carbon atoms), especially $C_1$ to $C_3$ alkyl and benzyloxy, most especially methoxy and benzyloxy. Particularly preferred are H, OH or OMe.

$R_2$ is H; or acetyl; alkyl-CO (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 7) especially $CH_3$—$(CH_2)_n$—CO— where n is for example 1, 2, 4, 6, 12, 14 or 16; haloalkyl-CO—, especially trifluoromethylcarbonyl, heptafluorobutyryl or 3-chloropropionyl; arylalkyl-CO—; arylalkenyl-CO—, especially cinnamoyl; alkyl-O—CO—, especially t-butyl-O—CO— or alkenyl-O—CO—, especially allyl-O—CO— or vinyl-O—CO.

$R_3$ is preferably H; alkenyl, especially allyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—$(CH_2)_n$—CO— where n is for example 1, 2, 4, 6, 12, 14 or 16; alkyl-O—CO—, especially t-butyl-O—CO—; alkenyl-O—CO, especially allyl-O—CO— and vinyl-O—CO.

$R_4$ is preferably H, alkyl (alkyl being 1 to 6 carbon atoms) especially $C_1$ to $C_3$ alkyl; alkenyl especially allyl, alkenyl-O—CO— especially vinyl-O—CO and $R_4$ is most especially H.

$R_5$ is H or alkyl (alkyl being 1 to 6 carbon atoms) and $R_5$ is most especially H or Me.

X is a H, —CN or OH, most especially —OH or —CN.

m is 0 or 1.

n is 0 or 1.

Compounds where R1 is not hydrogen are one class of preferred compounds. See for example compounds 27 to 36. These compounds have higher activity, a wider therapeutic window and improved pharmacokinetic properties. Preferred substituents are methoxy, methyl, hydroxy, benzyloxy, fluoro.

Compounds wherein $R_3$ is an ester or an ether are among the preferred compounds. In general they have improved toxicology properties and thus give a wider therapeutic window. Of those, compounds with an ester or carbonate at this position are most preferred, and in particular carbonates. Esters with bulky groups (long aliphatic or aromatic residues) give better results. Among the carbonates, terButyloxycarbonyl (TBOC) and vinyloxycarbonyl (VOC) are the most preferred substituents for these positions.

Compounds where $R_5$ is not hydrogen are another class of preferred compounds. See for example compounds 37 to 44. These compounds tend to be less active (cytotoxic) but have lower toxicity and improved pharmacokinetic properties. When $R_5$ is not hydrogen a chiral center is generated, and we have found that there is difference in activity between the diastereoisomers.

Compounds wherein $R_2$ is an ester or an ether are also preferred compounds. In general they have improved toxicology properties and thus give a wider therapeutic window. Of those, compounds with an ester or carbonate at this position are most preferred, and in particular carbonates. Esters with bulky groups (long aliphatic or aromatic residues) give better results. Among the carbonates, terButyloxycarbonyl (TBOC) and vinyloxycarbonyl (VOC) are the most preferred substituents for these positions.

There are compounds that have good ADME properties (absorption-distribution-metabolism-excretion) which are good indicative of pharmacokinetics.

As mentioned above, compounds of the present invention, preferably those with bulky substituted groups, have a good therapeutic window and the estherification of the phenols with different acids and carbonates, results in a general enhancement of the pharmaceutical properties: there is a significant decrease in hepatocyte toxicity, and also a good profile on drug-drug interactions since these derivatives do not show cytochrome inhibition having moreover higher metabolic stability.

Several active antitumor compounds have been prepared and it is believed that many more compounds may be formed in accordance with the teachings of the present disclosure.

Antitumoural activities of these compounds include leukaemias, lung cancer, colon cancer, kidney cancer, prostate cancer, ovarian cancer, breast cancer, sarcomas and melanomas.

Another especially preferred embodiment of the present invention is pharmaceutical compositions useful as antitumour agents which contain as active ingredient a compound or compounds of the invention, as well as the processes for their preparation.

Examples of pharmaceutical compositions include any solid (tablets, pills, capsules, granules etc) or liquid (solutions, suspensions or emulsions) with suitable compositions or oral, topical or parenteral administration.

Administration of the compounds or compositions of the present invention may be any suitable method, such as intravenous infusion, oral preparation, intraperitoneal and intravenous preparation.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the didemnins such as aplidine;

m) steroid analogues, in particular dexamethasone;

n) anti-inflammatory drugs, in particular dexamethasone; and o) anti-emetic drugs, in particular dexamethasone.

Yet another especially preferred embodiment of the present invention is the synthetic intermediates of the compounds of the present invention as described in detail below.

Finally, the present invention includes the synthetic processes described herein.

DETAILED DESCRIPTION OF THE PREFERRED EMBODIMENTS

One class of preferred compounds of this invention includes compounds of this invention which have one or more of the following substituents:

$R_1$ is hydrogen, hydroxy, halogen especially flouro, alkoxy especially methoxy, or aralkyl especially benzyl;

$R_2$ is hydrogen;

alkyl, more preferably alkyl of 1 to 6 carbon atoms;

$C(=O)R'$, where R' is alkyl, more preferably alkyl of 1 to 24 carbon atoms, especially 1 to 8 or 12 to 18 carbon atoms; haloalkyl, more preferably ω-chloro- or perfluoro-alkyl of 1 to 4 carbon atoms, especially ω-chloroethyl or perfluoromethyl, ethyl or propyl; heterocyclicalkyl, more preferably an alkyl of 1 to 6 carbon atoms with an ω-heterocyclic substituent suitably having 5 to 10 ring atoms and 1 to 4 heteroatoms, including fused heteroalicyclic with 3 hetero atoms, such as biotin; aminoalkyl, more preferably alkyl of 1 to 6 carbon atoms, especially 2 carbon atoms, with an ω-amino group optionally protected for example with alkoxycarbonyl such as $(CH_3)_3C-O-C=O-$ or other protecting group;

arylalkylene, especially cinnamoyl; alkylene, especially vinyl or allyl; aralkyl, such as benzyl; or $C(=O)OR'$, where R' is alkyl, more preferably alkyl of 1 to 6 carbon atoms, especially branched alkyl; alkenyl, more preferably allyl;

$R_3$ is hydrogen;

alkyl, more preferably alkyl of 1 to 6 carbon atoms;

$(C=O)R'$, where R' is alkoxy, especially with an alkyl group of 1 to 6 carbon atoms; alkyl, more preferably alkyl of 1 to 24 carbon atoms, preferably 1 to 8 or 12 to 18 carbon atoms; haloalkyl, more preferably perfluoroalkyl of 1 to 4 carbon atoms, especially perfluoromethyl, ethyl or propyl; arylalkylene, especially cinnamoyl; heterocyclicalkyl, more preferably an alkyl of 1 to 6 carbon atoms with an ω heterocyclic substituent suitably having 5 to 12 ring atoms and 1 to 4 heteroatoms, including fused heterocyclic with 3 ring atoms, such as biotin; heterocyclicalkyl, with preferably 1 carbon atom in the alkyl group, and more preferably heteroalicyclic-methyl with 5 to 10 ring atoms and 1 to 4 ring atoms, especially fused heterocyclic with 1 to 4 heteroatoms, such as dimethylaminocoumarin or coumarin; alkylene, especially allyl; aralkyl, such as benzyl;

(C=O)OR', where R' is alkyl, more preferably alkyl of 1 to 6 carbon atoms; alkylene, especially vinyl or allyl; aralkyl, such as benzyl.

$R_4$ is hydrogen;

alkyl, more preferably alkyl of 1 to 6 carbon atoms;

(C=O)OR', where R' is alkylene, especially vinyl.

$R_5$ is hydrogen or alkyl.

X is hydrogen, hydroxy, cyano or keto.

m is 0 or 1.

n is 0 or 1.

In a related aspect of this invention, the compounds have one or more of the following features:

$R_2$ is not acetyl. Preferably it has at least 4, 5 or 6 carbon atoms, for example up to 18 or 24 carbon atoms. Suitable substituents include esters COR', where R' is alkyl, alkenyl, often with one or more substituents. Alkyl, substituted alkyl, alkenyl and arylalkenyl are preferred, with suitable substituents including aryl, heterocyclic. Other definitions for $R_2$ include esters of formula COR' derived from an amino acid, optionally a protected amino acid.

$R_3$ is not hydrogen. Preferably it is R', COR' or COOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent $R_3$. Preferably the total number of carbon atoms in $R_3$ is 2 to 24, more preferably 6 to 18 carbon atoms. Typically $R_3$ is an ester, ether or carbonate, being of formula COR', R' or COOR'.

$R_5$ is not hydrogen. Preferably it is R', COR' or COOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent $R_5$. Preferably the total number of carbon atoms in $R_5$ is 2 to 24, more preferably 6 to 18 carbon atoms. Typically $R_4$ is an ester, ether or carbonate, being of formula COR', R' or COOR'.

Examples of protecting groups for amino and other substituents are given in WO 0069862, and we expressly incorporate that disclosure.

This application claims priority of a British patent application. We expressly incorporate by reference any disclosure which is in the specification of that British priority application and which is not in the present application.

Furthermore, we expressly incorporate by reference each of WO 0069862, WO 0177115, WO 0187894 and WO 0187895 for their discussion of substituents which correspond to the substituents of the present invention. Any definitions given in any of these earlier applications for a particular substituent can be adopted for a substituent of a compound of this invention.

Furthermore, we do not claim any of the compounds disclosed in the earlier applications, including WO 9209607, and we expressly disclaim any such compounds. We expressly incorporate by reference each of the earlier applications for the wording of any disclaimer which might be necessary.

Disclosed in international patent application WO 0069862 is compound 36 (an intermediate in the conversion of cyanosafracin B to Ecteinascidin 743).

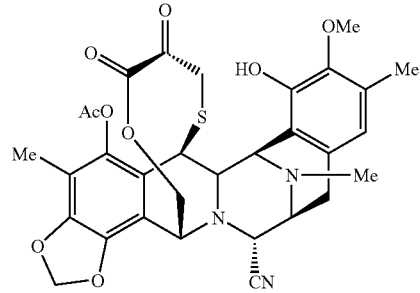

36

This hemi-synthetic intermediate has served as the starting material for the synthesis of ecteinascidin 736, a further member of the naturally occurring ecteinascidin family with potential antitumor therapeutic activity.

The preferred method of producing ecteinascidin 736 and related compounds with different substituents in the tetrahydro-β-carboline unit and in the position 18 (—OR$_4$) are described below in the following reaction scheme.

Scheme 1

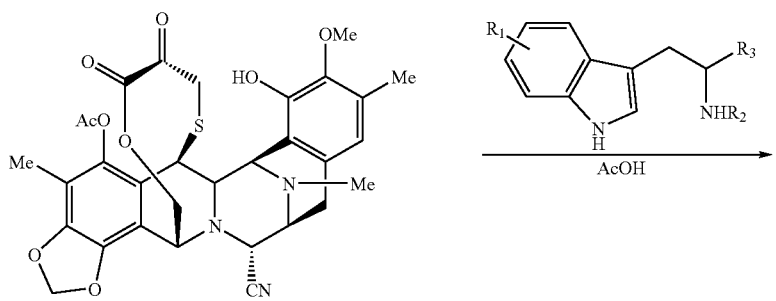

36

-continued

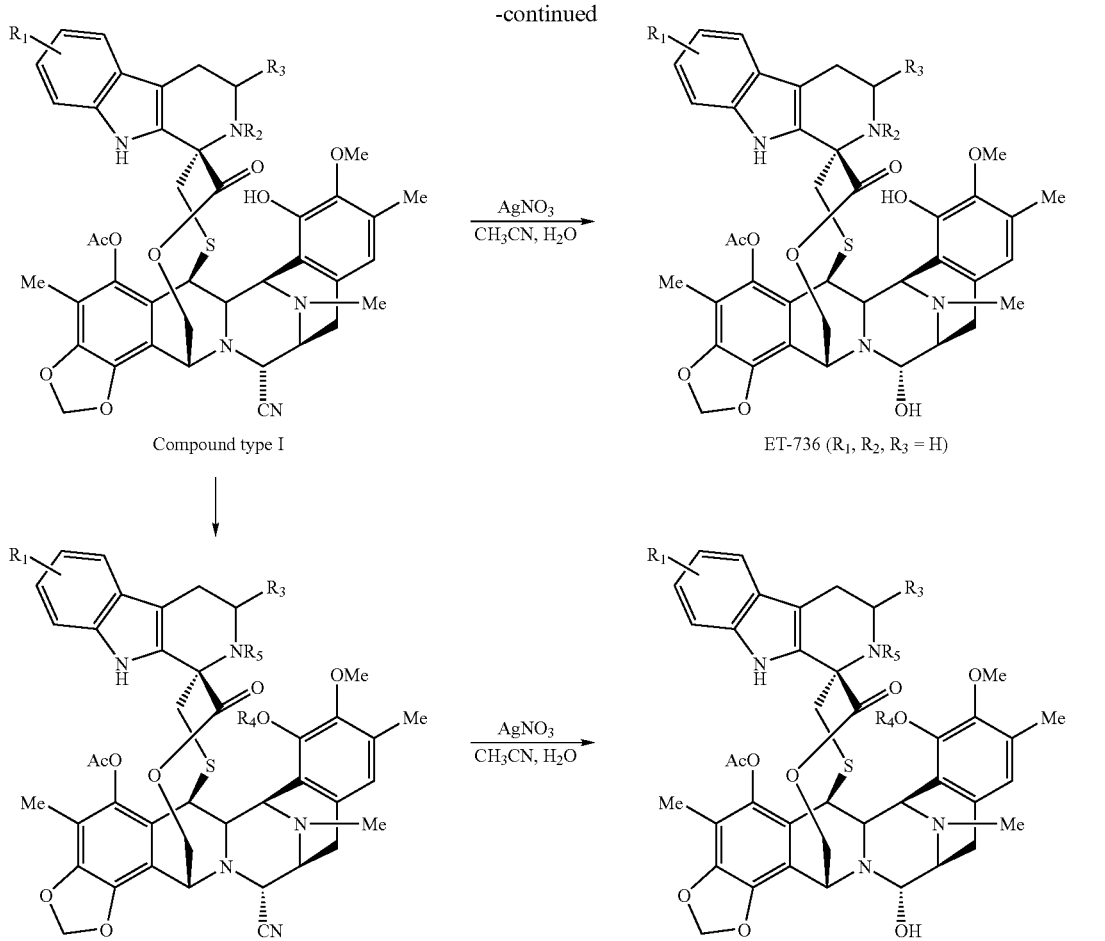

Compound type I

ET-736 (R₁, R₂, R₃ = H)

As illustrated in Scheme 1, intermediate 36 can be converted to ET-736 (or a substituted derivative) in two steps.

The first step for producing the preferred compounds type I of the present invention from compound 36 is the introduction of the tetrahydro-β-carboline unit by reaction with the corresponding primary or secondary amine.

The second step is the transformation of the CN group into an OH group by reaction with silver nitrate in ACN/H₂O.

Also is possible to obtain new derivatives with different substituent groups (—OR₄, position 18 and =NR₅) trough a acylation or alkylation reaction from the preferred compounds I. In all theses cases R₁ and R₂ in the starting material is an hydrogen atom. From the same intermediate and through an alkylation reaction with allyl bromide or an acylation reaction with vinylchloroformiate it can be obtained N and O allylated and N and O vinyl derivatives. All these compounds by reaction with silver nitrate lead to the final products wherein the CN group is transformed into an OH group.

As the skilled artisan will readily appreciate, the reaction scheme described herein may be modified by use of a wide range of substituted primary amines to produce a series of substituted ecteinascidin 736 derivatives and the compounds generated therefore are to be considered as being part of this invention.

In particular the reaction conditions can be varied to suit other combinations of the substituent groups in the tetrahydro-β-carboline unit.

The preferred method of producing ecteinascidin 694 and related compounds with different substituents in the position 5 and 18 (—OR₆ and —OR₇) are described below in the following reaction scheme.

Scheme 2

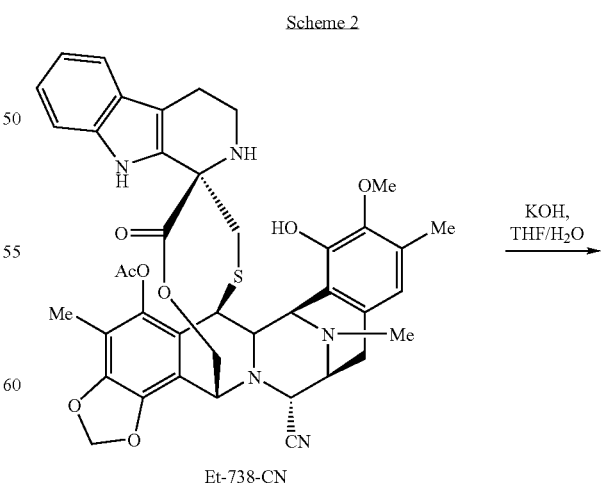

Et-738-CN

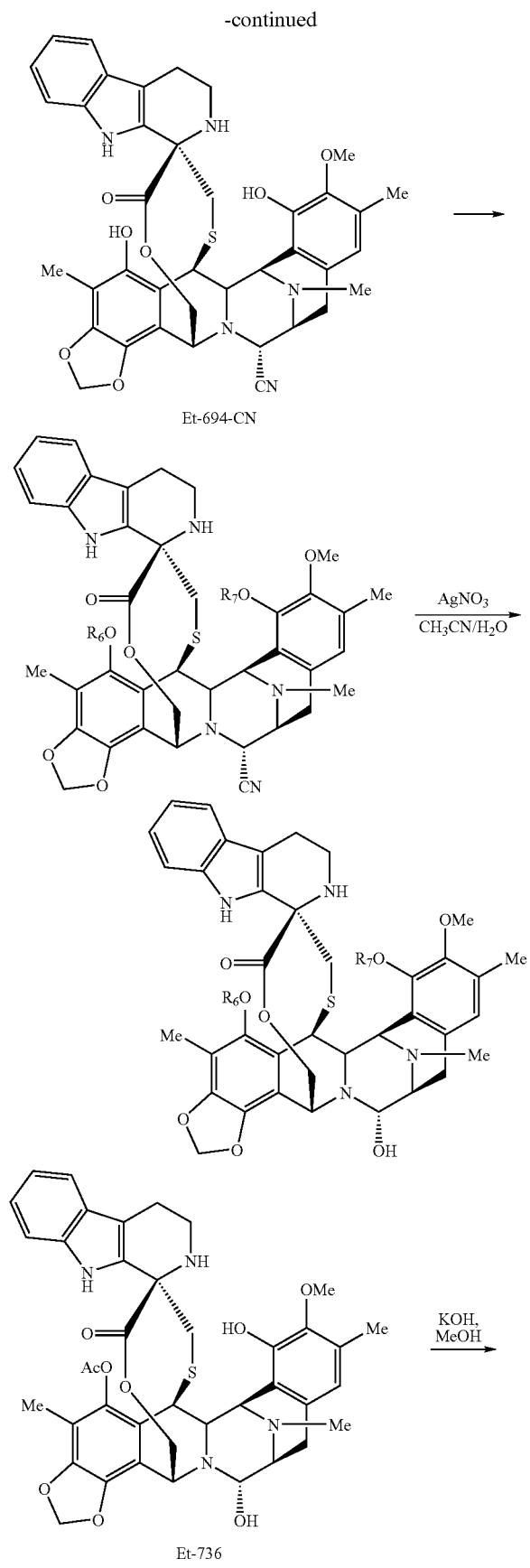

Et-694-CN

Et-736

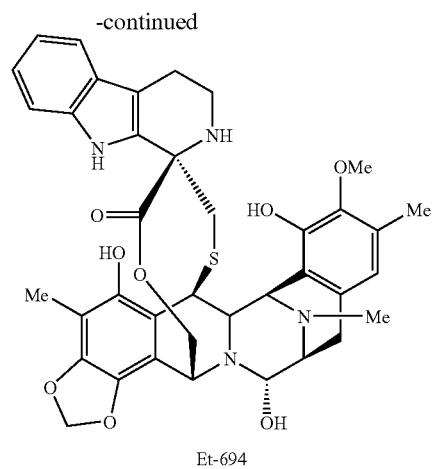

Et-694

In Scheme 2 the hydrolisis of the acetyl group in C-5 in basic conditions allows to prepare the intermediate with the hydroxyl group in this position. From this compound and by an acylation reaction with anhydrides, acid chlorides or carboxylic acids are prepared new derivatives mono-O substituted and mono and di-O substituted (in C-5 and C-18). The reaction to transform the CN group into the OH is performed in the classic conditions (silver nitrate in $CH_3CN/H_2O$). On the other hand Et-694 can be obtained from Et-736 through the hydrolisis of the acetyl group in C-5 with KOH/MeOH.

As the skilled artisan will readily appreciate, the reaction scheme described herein may be modified by use of a wide range of substituted primary amines to produce a series of substituted ecteinascidin 736-CN derivatives and the compounds generated therefore are to be considered as being part of this invention.

In particular the reaction conditions can be varied to suit other combinations of the substituent groups in the tetrahydro-β-carboline unit and in positions C-5 and C-18.

The present invention will be further illustrated with reference to the following examples which aid in the understanding, but which are not to be construed as limitations thereof.

EXPERIMENTAL PART

Scheme 1

Method 1.—To a solution of 1 equiv. of starting material in acetic acid (5.33 E-5M) under argon at room temperature was added 3.5 equiv. of tryptamine. The reaction mixture was stirred during 24 h and then the acetic acid was evaporated. An aqueous saturated solution of $NaHCO_3$ was added and the mixture was extracted with $CH_2Cl_2$ and the organic layers were dried over $Na_2SO_4$. Flash chromatography gives pure compounds.

Method 2.—To a solution of 1 equiv. of compound 1 in $CH_2Cl_2$ (0.032M) under Argon at room temperature were added 2 equiv. of Et3N and 2 equiv. of the butyiyl chloride or Boc anhydride (3 equiv.) or vinylchloroformiate. The reaction was followed by TLC and quenched with an aqueous saturated solution of $NaHCO_3$, extracted with $CH_2Cl_2$ and the organic layers dried over $Na_2SO_4$. Flash chromatography gives pure compound.

Method 3.—To a solution of 1 equiv. of compound 1 in DMF (0.032M) under Argon at room temperature were added 3 equiv. of $CS_2CO_3$ and 3 equiv. of the allyl bromide. The reaction was followed by TLC and quenched with an aqueous saturated solution of NaHCO₃, extracted with CH₂Cl₂ and the organic layers dried over Na₂SO₄. Flash chromatography gives a mixture of two pure compounds: compound 24 (ET-736-CN-All) and compound 25 (ET-736-CN-diAll).

Method 4.—To a solution of 1 equiv. of starting material in CH₃CN/H₂O 3:2 (0.009M) were added 30 equiv. of AgNO₃. After 24 h the reaction was quenched with a mixture 1:1 of saturated solutions of brine and NaHCO₃, stirred for 10 min and diluted and extracted with CH₂Cl₂. The organic layer was dried with Na₂SO₄. Chromatography gives pure compounds.

Method 1:

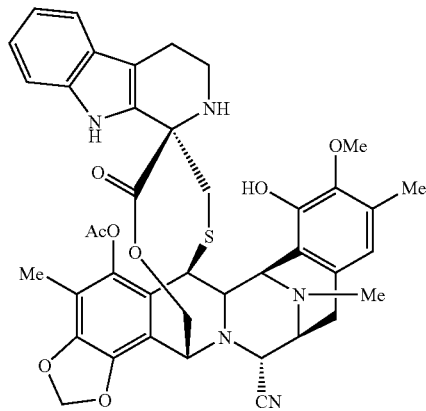

Compound 1: ¹H-NMR (300 MHz, CDCl₃): δ 7.74 (s, 1H); 7.38 (d, 1H); 7.25 (d, 1H); 7.08 (t, 1H); 7.00 (t, 1H); 6.66 (s, 1H); 6.22 (d, 1H); 6.02 (d, 1H); 5.79 (s, 1H); 5.08 (d, 1H); 4.55 (s, 1H); 4.32 (s, 1H); 4.27 (d, 1H); 4.21 (s, 1H); 4.19 (d, 1H); 3.81 (s, 3H); 3.44-3.40 (m, 2H); 3.18-2.78 (m, 4H); 2.71-2.51 (m, 3H); 2.37 (s, 3H); 2.26 (s, 3H); 2.21 (s, 3H); 2.06 (s, 3H).

¹³C-NMR (75 MHz, CDCl₃): δ 171.7, 168.9, 148.2, 145.9, 143.2, 141.3, 140.5, 135.7, 130.8, 130.6, 129.5, 127.0, 122.2, 120.9, 120.8, 119.5, 118.6, 118.4, 113.8, 111.1, 110.5, 102.2, 62.5, 61.5, 60.8, 60.5, 59.7, 55.9, 54.8, 42.1, 41.7, 40.0, 39.5, 29.9, 24.0, 21.7, 20.8, 16.1, 9.9.

ESI-MS m/z: Calcd. for C₄₁H₄₁N₅O₈S: 763.3 Found (M+H⁺): 764.2.

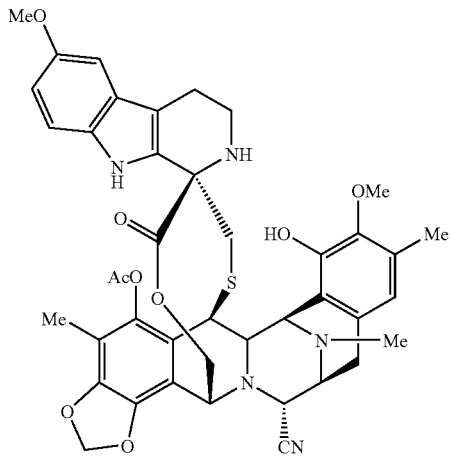

Compound 2: ¹H-NMR (300 MHz, CDCl₃): δ 7.64 (s, 1H); 7.12 (d, 1H); 6.81 (d, 1H); 6.73 (dd, 1H); 6.65 (s, 1H); 6.19 (s, 1H); 6.00 (s, 1H); 5.79 (s, 1H); 5.0 (d, 1H); 4.54 (s, 1H); 4.30 (s, 1H); 4.27 (d, 1H); 4.20 (s, 1H); 4.18 (d, 1H); 3.80 (s, 3H); 3.78 (s, 3H); 3.43-3.40 (m, 2H); 3.18-2.77 (m, 4H); 2.66-2.49 (m, 3H); 2.37 (s, 3H); 2.34-2.20 (m, 1H); 2.26 (s, 3H); 2.21 (s, 3H); 2.05 (s, 3H).

¹³C-NMR (75 MHz, CDCl₃): δ 171.4, 168.6, 153.7, 148.0, 145.6, 142.9, 141.0, 140.2, 131.1, 130.6, 130.5, 129.2, 127.0, 120.6, 120.5, 118.2, 113.6, 111.9, 111.6, 110.0, 102.0, 100.3, 62.3, 61.2, 60.5, 60.2, 59.4, 55.7, 54.6, 54.5, 41.8, 41.4, 39.7, 39.2, 31.5, 29.6, 23.8, 22.6, 21.5, 20.5, 15.8, 14.4, 9.7. ESI-MS m/z: Calcd. for C₄₂H₄₃N₅O₉S: 793.3 Found (M+H⁺): 794.7.

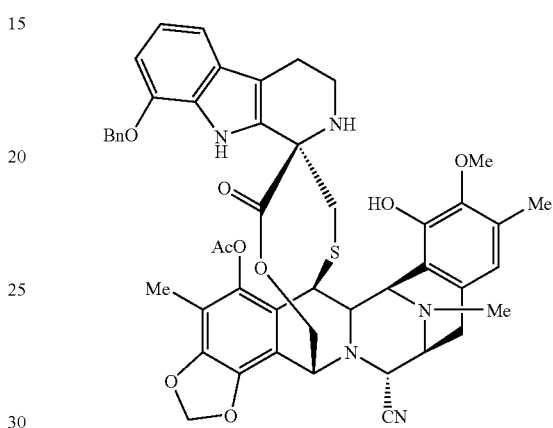

Compound 3: ¹H-NMR (300 MHz, CDCl₃): δ 7.85 (s, 1H); 7.45-7.36 (m, 5H); 7.01 (t, 1H); 6.91 (t, 1H); 6.65-6.63 (m, 2H); 5.87 (s, 1H); 5.77 (s, 1H); 5.63 (s, 1H); 5.13 (s, 2H); 5.05 (d, 1H); 4.53 (s, 1H); 4.27-4.19 (m, 4H); 3.80 (s, 3H); 3.46-3.39 (m 2H); 3.06-2.79 (m, 4H); 2.68-2.50 (m 2H); 2.42-2.20 (m, 1H); 2.36 (s, 3H); 2.27 (s, 3H); 2.20 (s, 3H); 2.03 (s, 3H).

ESI-MS m/z: Calcd. for C₄₈H₄₇N₅O₉S: 869.3 Found (M+H⁺): 870.3.

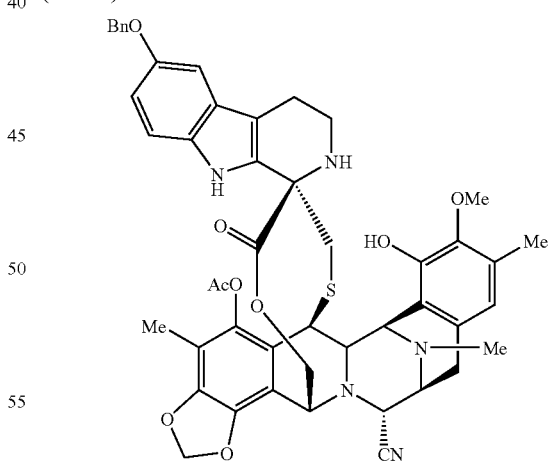

Compound 4: ¹H-NMR (300 MHz, CDCl₃): δ 7.36 (s, 1H); 7.44-7.25 (m 5H); 7.13 (d, 1H); 6.91 (d, 1H); 6.82 (dd, 1H); 6.65 (s, 1H); 6.21 (d, 1H); 6.01 (d, 1H); 5.80 (s, 1H); 5.08 (d, 1H); 5.03 (s, 2H); 4.55 (s, 1H); 4.31 (s, 1H); 4.27 (d, 1H); 4.20-4.10 (m, 3H); 3.81 (s, 3H); 3.44-3.40 (m 2H); 3.18-2.77 (m, 4H); 2.60-2.46 (m, 2H); 2.37 (s, 3H); 2.35-2.19 (m, 1H); 2.26 (s, 3H); 2.21 (s, 3H); 2.06 (s, 3H).

ESI-MS m/z: Calcd. for C₄₈H₄₇N₅O₉S: 869.3 Found (M+H⁺): 870.3.

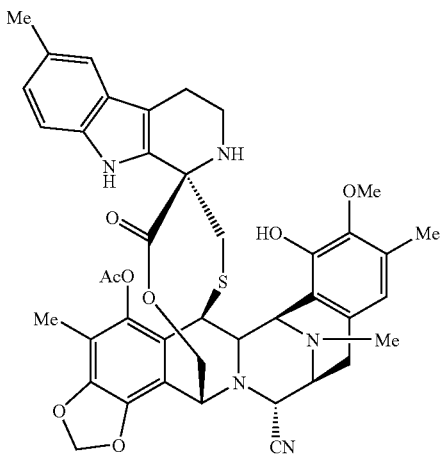

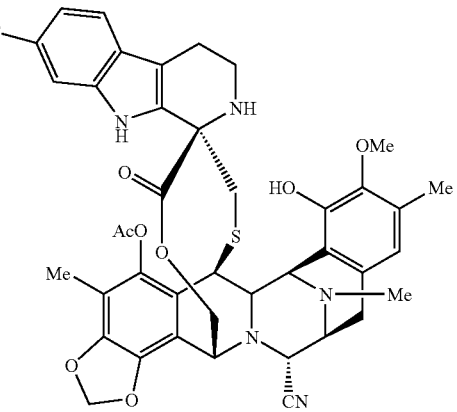

Compound 5: ¹H-NMR (300 MHz, CDCl₃): δ 7.63 (s, 1H); 7.15-7.11 (m, 2H); 6.91 (dd, 1H); 6.65 (s, 1H); 6.21 (d, 1H); 6.01 (s, 1H); 5.78 (s, 1H); 5.07 (d, 1H); 4.54 (s, 1H); 4.31 (s, 1H); 4.27 (d, 1H); 4.21-4.16 (m, 2H); 3.81 (s, 3H); 3.44-3.40 (m, 2H); 3.17-2.77 (m, 4H); 2.66-2.46 (m, 3H); 2.31 (s, 6H); 2.26 (s, 3H); 2.21 (s, 3H); 2.06 (s, 3H).

ESI-MS m/z: Calcd. for $C_{42}H_{43}N_5O_8S$: 777.3 Found (M+Na⁺): 800.7.

Compound 7: ¹H-NMR (300 MHz, CDCl₃): δ 7.75 (s, 1H); 7.26 (dd, 1H); 6.93 (dd, 1H); 6.76 (ddd, 1H); 6.65 (s, 1H); 6.22 (d, 1H); 6.01 (d, 1H); 5.79 (s, 1H); 5.08 (d, 1H); 4.55 (s, 1H); 4.31 (s, 1H); 4.25 (d, 1H); 4.20 (s, 1H); 4.18 (dd, 1H); 3.80 (s, 3H); 3.43-3.40 (m, 2H); 3.18-2.77 (m, 4H); 2.64-2.50 (m, 3H); 2.36 (s, 3H); 2.26 (s, 3H); 2.21 (s, 3H); 2.06 (s, 3H).

ESI-MS m/z: Calcd. for $C_{41}H_{40}FN_5O_8S$: 781.3 Found (M+H⁺): 782.3.

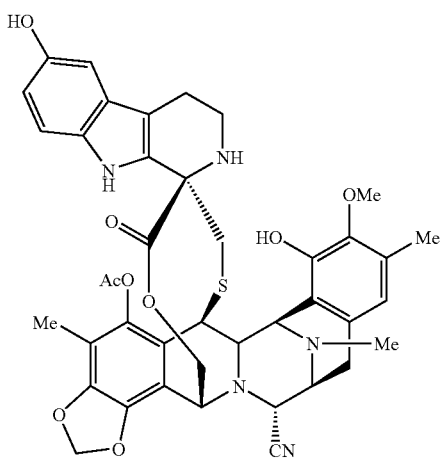

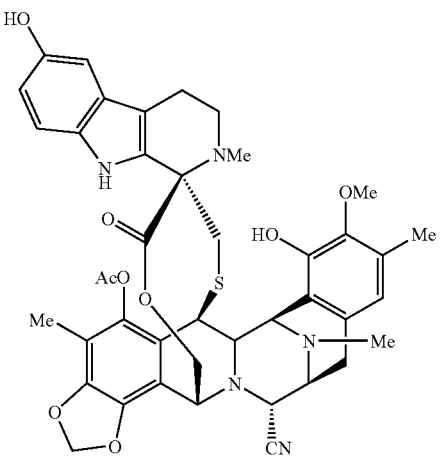

Compound 6: ¹H-NMR (300 MHz, CDCl₃): δ 7.66 (s, 1H); 6.95 (d, 1H); 6.64 (s, 2H); 6.56 (dd, 1H); 6.15 (s, 1H); 5.97 (s, 1H); 5.81 (s, 1H); 5.06 (d, 1H); 4.53 (s, 1H); 4.29 (s, 1H); 4.26 (d, 1H); 4.19 (s, 1H); 4.17 (d, 1H); 3.80 (s, 3H); 4.41-3.39 (m, 2H); 3.12-2.73 (m, 4H); 2.55-2.27 (m, 3H); 2.36 (s, 3H); 2.25 (s, 3H); 2.20 (s, 3H); 2.04 (s, 3H).

ESI-MS m/z: Calcd. for $C_{41}H_{41}N_5O_9S$: 779.3 Found (M+H⁺): 780.3.

Compound 8: ¹H-NMR (300 MHz, CDCl₃): δ 6.93 (d, 1H); 6.80 (s, 1H); 6.73 (s, 1H); 6.67 (dd, 1H); 6.46 (s, 1H); 6.20 (s, 1H); 6.06 (s, 1H); 5.72 (s, 1H); 4.96 (d, 1H); 4.45 (s, 1H); 4.37 (d, 1H); 4.25 (d, 1H); 4.05-4.01 (m, 2H); 3.79 (s, 3H); 3.63 (d, 1H); 3.39 (d, 1H); 3.03-3.91 (m, 2H); 2.76-2.34 (m, 5H); 3.30 (s, 3H); 2.28 (s, 3H); 2.21 (s, 3H); 2.18 (s, 3H); 2.04 (s, 3H).

ESI-MS m/z: Calcd. for $C_{42}H_{43}N_5O_9S$: 793.3 Found (M+H⁺): 794.3.

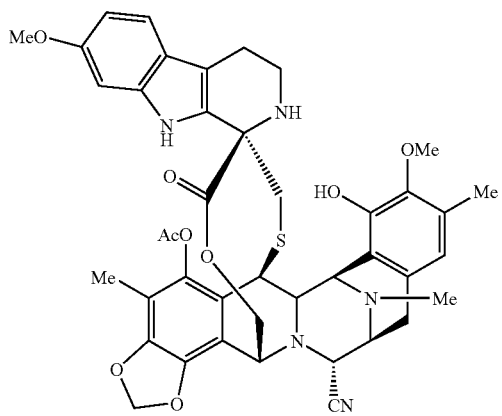

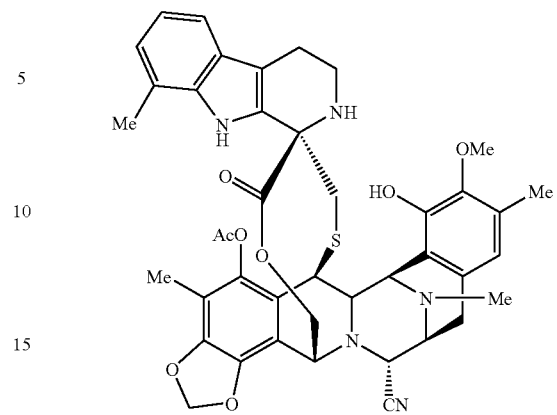

Compound 9: $^1$H-NMR (300 MHz, CDCl$_3$): δ 7.63 (s, 1H); 7.24 (d, 1H); 6.75 (d, 1H); 6.66 (dd, 1H); 6.65 (s, 1H); 6.20 (s, 1H); 6.00 (s, 1H); 5.79 (s, 1H); 5.07 (d, 1H); 4.54 (s, 1H); 4.31 (s, 1H); 4.27 (d, 1H); 4.20 (d, 1H); 4.17 (dd, 1H); 3.80 (s, 3H); 3.71 (s, 3H); 3.43-3.40 (m, 2H); 3.16-2.78 (m, 4H); 2.64-2.49 (m, 3H); 2.36 (s, 3H); 2.25 (s, 3H); 2.21 (s, 3H); 2.06 (s, 3H).

ESI-MS m/z: Calcd. for C$_{42}$H$_{43}$N$_5$O$_9$S: 793.3 Found (M+H$^+$): 794.3.

Compound 11: $^1$H-NMR (300 MHz, CDCl$_3$): δ 7.48 (s, 1H); 7.22 (d, 1H); 6.96-6.88 (m, 2H); 6.65 (s, 1H); 6.15 (d, 1H); 6.04 (d, 1H); 5.78 (s, 1H); 5.09 (d, 1H); 4.55 (s, 1H); 4.34 (s, 1H); 4.28-4.20 (m, 3H); 3.81 (s, 3H); 3.48 (d, 1H); 3.42 (d, 1H); 3.12-2.78 (m, 4H); 2.69-2.43 (m, 3H); 2.37 (s, 3H); 2.36 (s, 3H); 2.28 (s, 3H); 2.21 (s, 3H); 2.06 (s, 3H).

ESI-MS m/z: Calcd. for C$_{42}$H$_{43}$N$_5$O$_8$S: 777.3 Found (M+H$^+$): 778.3

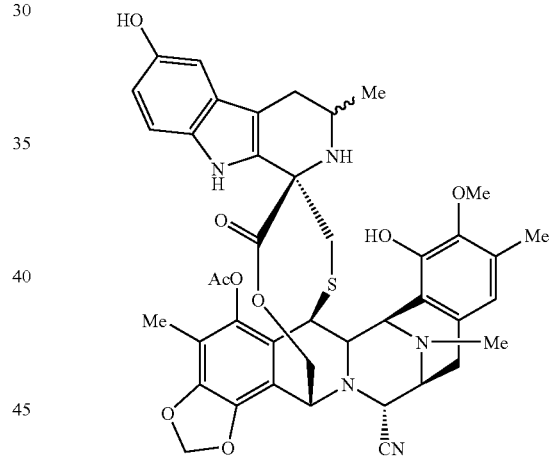

Compound 12 (first isomer): $^1$H-NMR (300 MHz, CDCl$_3$): δ 7.68 (s, 1H); 7.05 (d, 1H); 6.63-6.57 (m, 3H); 6.22 (d, 1H); 6.02 (d, 1H); 5.73 (s, 1H); 5.12 (d, 1H); 4.58 (s, 1H); 4.36 (s, 1H); 4.34-4.22 (m, 3H); 3.80 (s, 3H); 3.47-3.42 (m, 2H); 3.05-2.86 (m, 2H); 2.67-2.35 (m, 2H); 2.32-2.05 (m, 3H); 2.31 (s, 3H); 2.28 (s, 3H); 2.15 (s, 3H); 2.03 (s, 3H); 1.07 (d, 3H).

ESI-MS m/z: Calcd. for C$_{42}$H$_{43}$N$_5$O$_9$S: 793.2 Found (M+H$^+$): 794.2.

Compound 13 (second isomer): $^1$H-NMR (300 MHz, CDCl$_3$): δ 7.54 (s, 1H); 7.08 (d, 1H); 6.73 (d, 1H); 6.63 (dd, 1H); 6.57 (s, 1H); 6.20 (d, 1H); 6.00 (d, 1H); 5.74 (s, 1H); 5.02 (d, 1H); 4.60 (s, 1H); 4.33 (s, 1H); 4.27 (d, 1H); 4.22 (d, 1H); 4.12 (dd, 1H); 3.80 (s, 3H); 3.44-3.32 (m, 3H); 3.05-2.89 (m, 2H); 2.49-2.03 (m, 4H); 2.32 (s, 3H); 2.24 (s, 3H); 2.18 (s, 3H); 2.07 (s, 3H); 1.21 (d, 3H).

ESI-MS m/z: Calcd. for C$_{42}$H$_{43}$N$_5$O$_9$S: 793.2 Found (M+H$^+$): 794.2.

Compound 10: $^1$H-NMR (300 MHz, CDCl$_3$): δ 7.76 (s, 1H); 7.14 (dd, 1H); 7.00 (dd, 1H); 6.81 (ddd, 1H); 6.65 (s, 1H); 6.21 (d, 1H); 6.00 (d, 1H); 5.79 (s, 1H); 5.07 (d, 1H); 4.55 (s, 1H); 4.31 (s, 1H); 4.27 (dd, 1H); 4.20 (d, 1H); 4.18 (dd, 1H); 3.80 (s, 3H); 3.44-3.40 (m, 2H); 3.16-2.77 (m, 4H); 2.64-2.44 (m, 3H); 2.37 (s, 3H); 2.26 (s, 3H); 2.21 (s, 3H); 2.05 (s, 3H).

ESI-MS m/z: Calcd. for C$_{41}$H$_{40}$FN$_5$O$_8$S: 781.3 Found (M+H$^+$): 782.1.

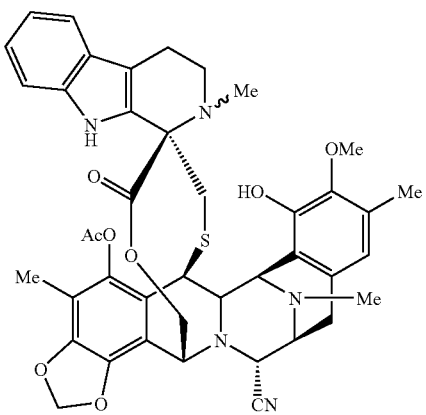

Compound 14 (first isomer): ¹H-NMR (300 MHz, CDCl₃): δ 7.98 (s, 1H); 7.40 (dd, 1H); 6.18 (t, 1H); 7.04 (t, 1H); 6.82 (s, 1H); 6.16 (d, 1H); 6.01 (d, 1H); 5.74 (s, 1H); 4.95 (d, 1H); 4.64 (s, 1H); 4.40 (s, 1H); 4.30-4.24 (m, 3H); 3.62 (s, 3H); 3.56 (d, 1H); 3.50 (d, 1H); 3.12-2.89 (m, 4H); 2.75-2.51 (m, 3H); 2.43 (s, 3H); 2.38-2.30 (m, 2H); 2.26 (s, 3H); 2.19 (s, 3H); 2.08 (s, 3H); 2.00 (s, 3H).

ESI-MS m/z: Calcd. for $C_{42}H_{43}N_5O_8S$: 777.2 Found (M+H⁺): 778.2.

Compound 15 (second isomer): ¹H-NMR (300 MHz, CDCl₃): δ 7.36 (d, 1H); 7.15-7.06 (m, 2H); 7.01 (ddd, 1H); 6.93 (s, 1H); 6.47 (s, 1H); 6.22 (d, 1H); 6.09 (d, 1H); 5.72 (s, 1H); 4.97 (d, 1H); 4.46 (s, 1H); 4.40 (d, 1H); 4.26 (dd, 1H); 4.03 (dd, 1H); 4.02 (s, 1H); 3.80 (s, 3H); 3.63 (d, 1H); 3.39 (d, 1H); 3.00-2.92 (m, 2H); 2.77-2.54 (m, 4H); 2.30 (s, 3H); 2.26-2.25 (m, 2H); 2.23 (s, 6H); 2.19 (s, 3H); 2.05 (s, 3H).

ESI-MS m/z: Calcd. for $C_{42}H_{43}N_5O_8S$: 777.2 Found (M+H⁺): 778.2.

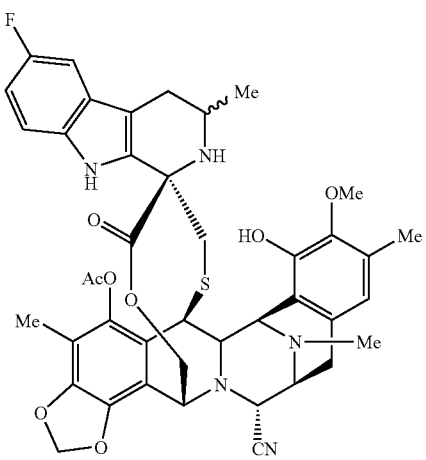

Compound 16 (first isomer): ¹H-NMR (300 MHz, CDCl₃): δ 7.82 (s, 1H); 7.14 (dd, 1H); 6.96 (dd, 1H); 6.82 (ddd, 1H); 6.61 (s, 1H); 6.23 (d, 1H); 6.02 (d, 1H); 5.72 (s, 1H); 5.12 (d, 1H); 4.59 (s, 1H); 4.37 (s, 1H); 4.32-4.25 (m, 3H); 3.80 (s, 3H); 3.48-3.43 (m, 2H); 3.05-2.86 (m, 4H); 2.78-2.70 (m, 1H); 2.60-2.34 (m, 3H); 2.31 (s, 3H); 2.27 (s, 3H); 2.16 (s, 3H); 2.03 (s, 3H); 1.12 (d, 3H).

ESI-MS m/z: Calcd. for $C_{42}H_{42}FN_5O_8S$: 795.3 Found (M+H⁺): 796.2.

Compound 17 (second isomer): ¹H-NMR (300 MHz, CDCl₃): δ 7.65 (s, 1H); 7.18 (dd, 1H); 6.99 (dd, 1H); 6.83 (ddd, 1H); 6.58 (s, 1H); 6.22 (d, 1H); 6.01 (d, 1H); 5.74 (s, 1H); 5.03 (d, 1H); 4.61 (s, 1H); 4.34 (s, 1H); 4.27 (d, 1H); 4.22 (d, 1H); 4.14-4.10 (m, 1H); 3.80 (s, 3H); 3.44 (d, 2H); 3.38-3.30 (m, 1H); 3.06-2.99 (m, 2H); 2.50 (dd, 1H); 2.43 (d, 1H); 2.32 (s, 3H); 2.24 (s, 3H); 2.18 (s, 3H); 2.16-2.11 (m, 2H); 2.08 (s, 3H); 1.20 (d, 3H).

ESI-MS m/z: Calcd. for $C_{42}H_{42}FN_5O_8S$: 795.3 Found (M+H⁺): 796.2.

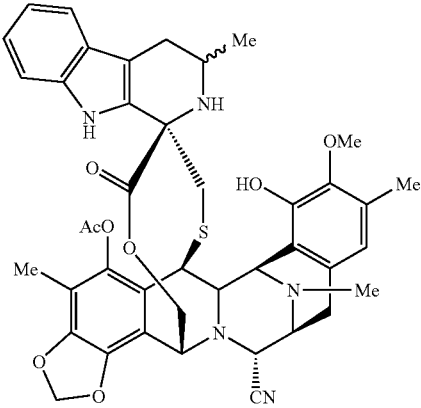

Compound 18 (first isomer): ¹H-NMR (300 MHz, CDCl₃): δ 7.83 (s, 1H); 7.34 (d, 1H); 7.24 (d, 1H); 7.09 (ddd, 1H); 7.00 (ddd, 1H); 6.62 (s, 1H); 6.24 (d, 1H); 6.03 (d, 1H); 5.73 (s, 1H); 5.13 (d, 1H); 4.59 (s, 1H); 4.38 (s, 1H); 4.33-4.27 (m, 3H); 3.80 (s, 3H); 3.48-3.43 (m, 2H); 3.06-2.87 (m, 2H); 2.78-2.72 (m, 1H); 2.61-2.24 (m, 4H); 2.32 (s, 3H); 2.27 (s, 3H); 2.16 (s, 3H); 2.03 (s, 3H); 1.13 (d, 3H).

ESI-MS m/z: Calcd. for $C_{42}H_{43}N_5O_8S$: 777.2 Found (M+H⁺): 778.2.

Compound 19 (second isomer): ¹H-NMR (300 MHz, CDCl₃): δ 7.66 (s, 1H); 7.37 (d, 1H); 7.28 (d, 1H); 7.10 (ddd, 1H); 7.00 (ddd, 1H); 6.58 (s, 1H); 6.24 (d, 1H); 6.02 (d, 1H); 5.75 (s, 1H); 5.03 (d, 1H); 4.61 (s, 1H); 4.35 (s, 1H); 4.28 (dd, 1H); 4.23 (d, 1H); 4.15-4.08 (m, 1H); 3.81 (s, 3H); 3.44 (d, 2H); 3.38-3.32 (m, 1H); 3.07-2.90 (m, 2H); 2.58 (dd, 1H); 2.45 (d, 1H); 2.33 (s, 3H); 2.27-2.12 (m, 2H); 2.24 (s, 3H); 2.19 (s, 3H); 2.08 (s, 3H); 1.20 (d, 3H).

ESI-MS m/z: Calcd. for $C_{42}H_{43}N_5O_8S$: 777.2 Found (M+H⁺): 778.2.

Method 2:

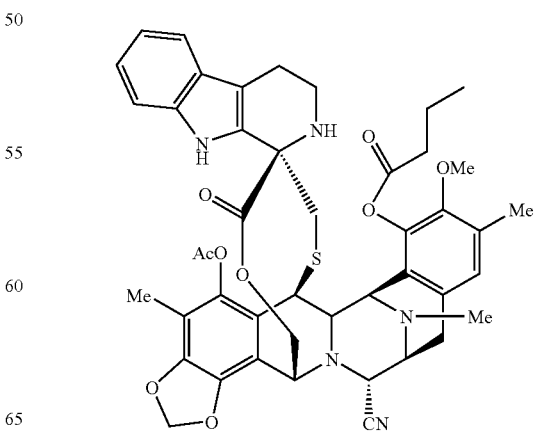

Compound 20: ¹H-NMR (300 MHz, CDCl₃): δ 7.70 (s, 1H); 7.38 (d, 1H); 7.25 (d, 1H); 7.10 (ddd, 1H); 7.02 (ddd, 1H); 7.01 (s, 1H); 6.24 (d, 1H); 1H); 6.03 (d, 1H); 5.09 (d, 1H); 4.44 (s, 1H); 4.33 (s, 1H); 4.22-4.18 (m, 2H); 3.81 (d, 1H); 3.77 (s, 3H); 3.48-3.44 (m, 2H); 3.19-2.81 (m, 4H); 2.70-2.48 (m, 3H); 2.62 (t, 2H); 2.37 (s, 3H); 2.34-2.15 (m, 2H); 2.29 (s, 3H); 2.18 (s, 3H); 2.04 (s, 3H); 1.95-1.82 (m, 2H); 1.10 (t, 3H).

ESI-MS m/z: Calcd. for $C_{45}H_{47}N_5O_9S$: 833.3 Found (M+H⁺): 834.2.

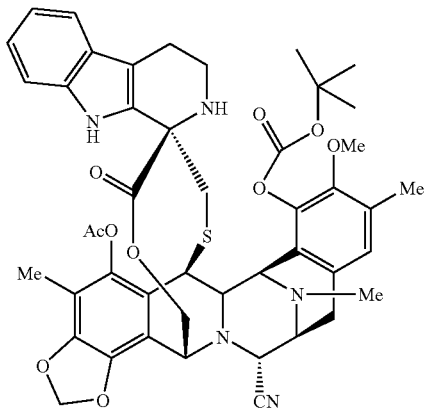

Compound 21: ¹H-NMR (300 MHz, CDCl₃): δ 7.70 (s, 1H); 7.38 (d, 1H); 7.24 (d, 1H); 7.09 (ddd, 1H); 7.00 (ddd, 1H); 6.99 (s, 1H); 6.22 (d, 1H); 6.02 (d, 1H); 5.08 (d, 1H); 4.48 (s, 1H); 4.32 (s, 1H); 4.25-4.21 (m, 2H); 3.81 (s, 3H); 3.46-3.44 (m, 2H); 3.18-2.79 (m, 4H); 2.72-2.43 (m, 3H); 2.36 (s, 3H); 2.31 (s, 3H); 2.20 (s, 3H); 2.08 (s, 3H); 1.54 (s, 9H).

ESI-MS m/z: Calcd. for $C_{46}H_{49}N_5O_{10}S$: 863.3 Found (M+H⁺): 864.2.

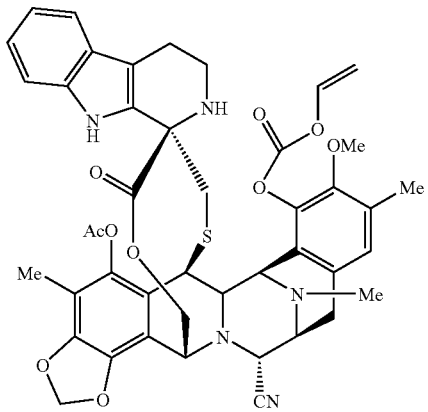

Compound 22: ¹H-NMR (300 MHz, CDCl₃): δ 7.70 (s, 1H); 7.26-6.99 (m, 5H); 6.24 (d, 1H); 6.03 (d, 1H); 5.09 (d, 1H); 5.00 (dd, 1H); 4.71 (dd, 1H); 4.48 (s, 1H); 4.33 (s, 1H); 4.24-4.21 (m, 2H); 3.95 (d, 1H); 3.81 (s, 3H); 3.48-3.45 (m, 2H); 3.18-2.81 (m, 4H); 2.72-2.45 (m, 3H); 2.38 (s, 3H); 2.34 (s, 3H); 2.30-2.11 (m, 2H); 2.20 (s, 3H); 2.08 (s, 3H).

ESI-MS m/z: Calcd. for $C_{44}H_{43}N_5O_{10}S$: 833.3 Found (M+H⁺): 834.2.

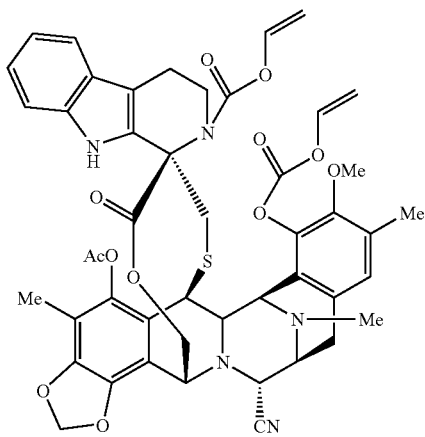

Compound 23: ¹H-NMR (300 MHz, CDCl₃): δ 7.38 (d, 1H); 7.20-7.13 (m, 3H); 7.07-6.98 (m, 2H); 6.88 (s, 1H); 6.66 (s, 1H); 6.18 (d, 1H); 6.12 (d, 1H); 4.95 (dd, 1H); 4.79 (d, 1H); 4.78 (dd, 1H); 4.68 (dd, 1H); 4.46 (dd, 1H); 4.40 (d, 1H); 4.34-4.18 (m, 3H); 3.97 (d, 1H); 3.89 (d, 1H); 3.85 (s, 3H); 3.61 (d, 1H); 3.41 (d, 1H); 3.17-2.98 (m, 3H); 2.76-2.42 (m, 4H); 2.37 (s, 3H); 2.32 (s, 3H); 2.18 (s, 3H); 2.13 (s, 3H).

ESI-MS m/z: Calcd. for $C_{47}H_{45}N_5O_{12}S$: 903.2 Found (M+Na⁺): 926.1

Method 3:

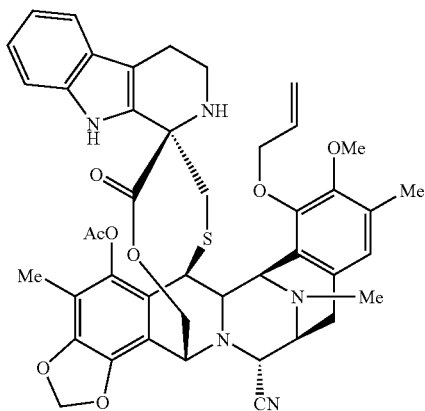

Compound 24: ¹H-NMR (300 MHz, CDCl₃): δ 7.71 (s, 1H); 7.38 (d, 1H); 7.24 (d, 1H); 7.09 (ddd, 1H); 7.00 (ddd, 1H); 6.86 (s, 1H); 6.22 (d, 1H); 6.16-6.04 (m, 1H); 6.02 (d, 1H); 5.47 (dd, 1H); 5.26 (dd, 1H); 5.09 (d, 1H); 4.83 (dd, 1H); 4.52 (s, 1H); 4.36 (dd, 1H); 4.32 (s, 1H); 4.24-4.19 (m, 3H); 3.84 (s, 3H); 3.45-3.41 (m, 2H); 3.18-2.79 (m, 4H); 2.73-2.47 (m, 3H); 2.33 (s, 3H); 2.31-2.26 (m, 1H); 2.24 (s, 3H); 2.21 (s, 3H); 2.06 (s, 3H); 2.03 (d, 1H).

ESI-MS m/z: Calcd. for $C_{44}H_{45}N_5O_8S$: 803.3 Found (M+H⁺): 804.3

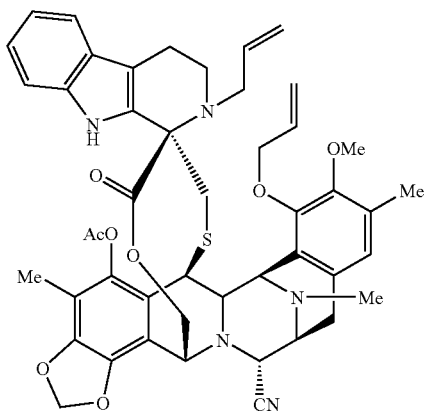

Compound 25: ¹H-NMR (300 MHz, CDCl₃): δ 7.39 (d, 1H); 7.25-7.23 (m, 1H); 7.09-6.98 (m, 3H); 6.80 (s, 1H); 6.14-6.00 (m, 1H); 6.10 (d, 1H); 6.02 (d, 1H); 5.60-5.40 (m, 1H); 5.45 (dd, 1H); 5.25 (dd, 1H); 5.02-4.95 (m, 2H); 4.81 (dd, 1H); 4.73-4.62 (m, 1H); 4.55 (s, 1H); 4.37-4.16 (m, 6H); 3.84 (s, 3H); 3.51 (d, 1H); 3.45-3.38 (m, 2H); 3.05-2.89 (m, 3H); 2.70-2.50 (m, 3H); 2.33-2.16 (m, 2H); 2.31 (s, 3H); 2.23 (s, 3H); 2.21 (s, 3H); 2.03 (s, 3H).

ESI-MS m/z: Calcd. for $C_{47}H_{49}N_5O_8S$: 843.3 Found (M+H⁺): 844.2.

Method 4:

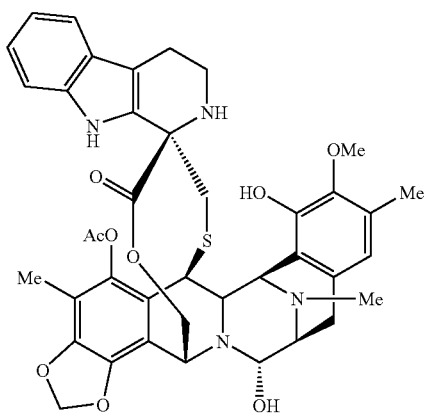

Compound 26: ¹H-NMR (300 MHz, CDCl₃): δ 7.70 (s, 1H); 7.38 (d, 1H); 7.24 (d, 1H); 7.08 (t, 1H); 7.00 (t, 1H); 6.67 (s, 1H); 6.20 (d, 1H); 5.99 (d, 1H); 5.74 (s, 1H); 5.20 (d, 1H); 4.82 (s, 1H); 4.347-4.38 (m, 3H); 4.16-4.10 (m, 2H); 3.81 (s, 3H); 3.49 (d, 1H); 3.22-3.13 (m, 2H); 3.00 (d, 1H); 2.88-2.79 (m, 2H); 2.71-2.52 (m, 3H); 2.37 (s, 3H); 2.28-2.24 (m, 1H); 2.25 (s, 3H); 2.19 (s, 3H); 2.05 (s, 3H).

¹³C-NMR (75 MHz, CDCl₃): δ 171.4, 168.7, 147.8, 145.4, 142.8, 141.0, 140.6, 135.4, 131.2, 130.9, 129.0, 126.8, 121.8, 121.3, 120.9, 119.1, 118.3, 118.1, 115.5, 112.8, 110.8, 110.1, 101.7, 81.9, 62.3, 61.8, 60.2, 57.6, 57.4, 55.8, 54.9, 42.1, 41.2, 39.7, 39.2, 31.5, 23.5, 22.6, 21.5, 20.5, 15.8, 14.0, 9.6.

ESI-MS m/z: Calcd. for $C_{40}H_{42}N_4O_9S$: 754.3 Found (M-H₂O+H⁺): 737.2.

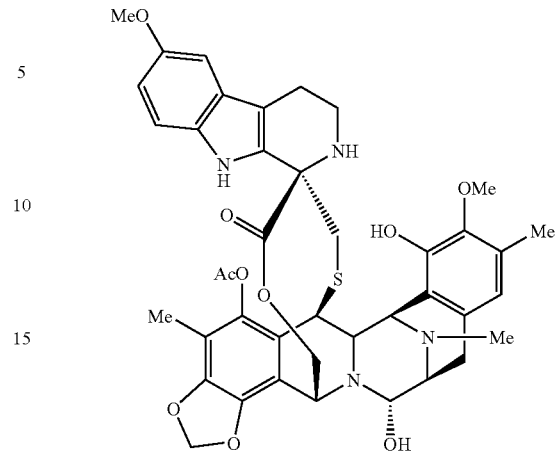

Compound 27: ¹H-NMR (300 MHz, CDCl₃): δ 7.59 (s, 1H); 7.13 (d, 1H); 6.81 (s, 1H); 6.73 (dd, 1H); 6.67 (s, 1H); 6.19 (d, 1H); 5.99 (d, 1H); 5.74 (s, 1H); 5.19 (d, 1H); 4.82 (s, 1H); 4.49-4.47 (m, 2H); 4.16-4.09 (m, 2H); 3.81 (s, 3H); 3.79 (s, 3H); 3.50-3.45 (m, 2H); 3.24-3.13 (m, 2H); 3.02 (d, 1H); 2.88-2.79 (m, 2H); 2.67-2.48 (m, 3H); 2.37 (s, 3H); 2.30-2.24 (m, 1H); 2.25 (s, 3H); 2.19 (s, 3H); 2.04 (s, 3H).

¹³C-NMR (75 MHz, CDCl₃): δ 171.6, 154.0, 148.1, 145.6, 143.1, 141.3, 140.9, 131.9, 131.4, 130.8, 129.3, 127.4, 121.5, 121.2, 115.7, 113.1, 112.1, 111.8, 110.1, 102.0, 100.6, 82.1, 62.6, 62.0, 60.5, 57.9, 57.6, 56.1, 56.0, 55.2, 42.4, 41.5, 40.0, 39.4, 31.8, 29.9, 23.8, 22.8, 21.8, 20.8, 16.0, 14.6, 9.9.

ESI-MS m/z: Calcd. for $C_{40}H_{42}N_4O_9S$: 784.4 Found (M-H₂O+H⁺): 767.2.

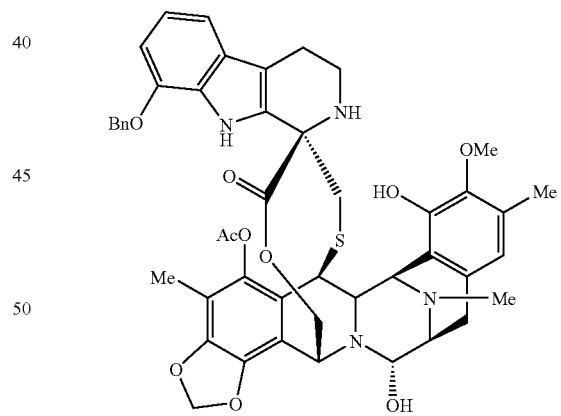

Compound 28: ¹H-NMR (300 MHz, CDCl₃): δ 7.81 (s, 1H); 7.43-7.36 (m, 5H); 7.01 (d, 1H); 6.91 (t, 1H); 6.66 (s, 1H); 6.63 (d, 1H); 5.84 (s, 1H); 5.75 (s, 1H); 5.60 (s, 1H); 5.20-5.09 (m, 3H); 4.78 (s, 1H); 4.49 (d, 1H); 4.44 (s, 1H); 4.16 (s, 1H); 4.14-4.12 (m, 1H); 3.81 (s, 3H); 3.52 (d, 1H); 3.47 (s, 2H); 3.22-2.80 (m, 5H); 2.68-2.51 (m, 2H); 2.36 (s, 3H); 2.39-2.21 (m, 1H); 2.27 (s, 3H); 2.18 (s, 3H); 2.02 (s, 3H).

¹³C-NMR (75 MHz, CDCl₃): δ 171.4, 148.0, 145.6, 145.2, 143.1, 141.1, 140.8, 137.3, 131.6, 130.7, 129.3, 128.8, 128.5, 128.2, 128.0, 126.2, 121.4, 121.3, 119.8, 118.1, 115.5, 113.0, 111.8, 111.0, 103.8, 101.8, 82.1, 70.6, 62.9, 61.9, 60.5, 58.0, 57.7, 56.1, 55.1, 42.3, 41.5, 40.0, 39.5, 29.9, 23.9, 22.0, 20.7, 16.0, 9.8.

ESI-MS m/z: Calcd. for $C_{47}H_{48}N_4O_{10}S$: 860.3 Found (M–H$_2$O+H$^+$): 843.3

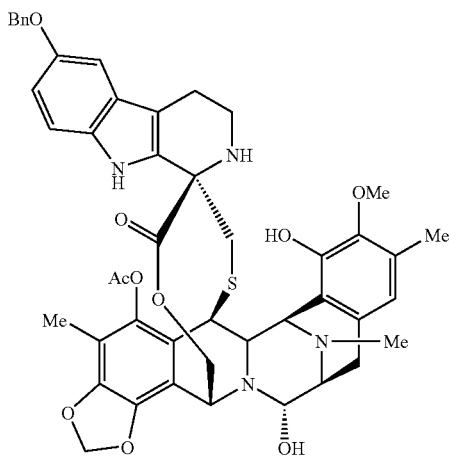

Compound 29: $^1$H-NMR (300 MHz, CDCl$_3$): δ 7.59 (s, 1H); 7.44-7.25 (m, 5H); 7.13 (d, 1H); 6.91 (s, 1H); 6.82 (d, 1H); 6.66 (s, 1H); 6.19 (s, 1H); 5.98 (s, 1H); 5.75 (s, 1H); 5.19 (d, 1H); 5.03 (s, 2H); 4.82 (s, 1H); 4.49-4.47 (m, 2H); 4.17-4.09 (m, 2H); 3.81 (s, 3H); 3.49-3.47 (m, 2H); 3.24-2.80 (m, 5H); 2.64-2.50 (m, 3H); 2.37 (s, 3H); 2.25 (s, 3H); 2.19 (s, 3H); 2.05 (s, 3H).

$^{13}$C-NMR (75 MHz, CDCl$_3$): δ 171.4, 168.6, 153.2, 148.1, 145.7, 143.1, 141.3, 140.9, 137.9, 131.0, 129.7, 128.6, 127.9, 127.8, 127.4, 121.2, 115.7, 112.8, 111.8, 110.2, 102.3, 102.0, 82.1, 71.1, 62.5, 62.0, 60.5, 58.0, 57.6, 56.1, 55.2, 42.4, 41.5, 40.0, 39.4, 32.1, 29.9, 29.5, 23.8, 22.9, 21.8, 20.8, 16.0, 14.6, 9.9.

ESI-MS m/z: Calcd. for $C_{47}H_{48}N_4O_{10}S$: 860.3 Found (M–H$_2$O+H$^+$): 843.3

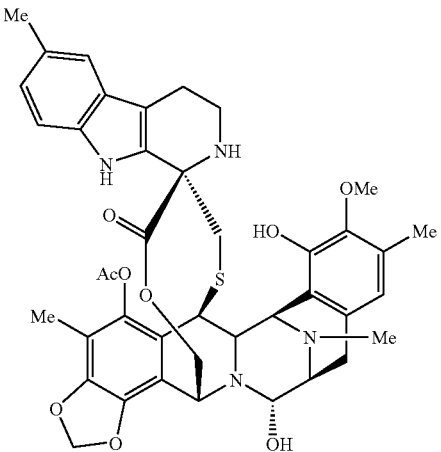

Compound 30: $^1$H-NMR (300 MHz, CDCl$_3$): δ 7.61 (s, 1H); 7.16-7.11 (m, 2H); 6.91 (d, 1H); 6.67 (s, 1H); 6.20 (d, 1H); 5.99 (d, 1H); 5.75 (s, 1H); 5.20 (d, 1H); 4.82 (s, 1H); 4.49 (d, 1H); 4.35 (s, 1H); 4.16 (d, 2H); 4.11 (dd, 1H); 3.81 (s, 3H); 3.48 (s, 1H); 3.23-2.79 (m, 5H); 2.67-2.47 (m, 3H); 2.37 (s, 6H); 2.25 (s, 3H); 2.19 (s, 3H); 2.05 (s, 3H).

$^{13}$C-NMR (75 MHz, CDCl$_3$): δ 174.5, 171.6, 168.9, 148.1, 145.6, 143.1, 141.3, 140.9, 134.0, 131.2, 128.6, 127.3, 123.6, 121.5, 121.2, 118.3, 115.7, 109.9, 102.0, 82.1, 62.6, 62.0, 60.5, 57.9, 57.7, 56.2, 56.1, 42.4, 41.5, 40.0, 39.4, 29.9, 23.8, 21.7, 21.6, 20.8, 16.0, 9.9.

ESI-MS m/z: Calcd. for $C_{41}H_{44}N_4O_9S$: 768.3 Found (M–H$_2$O+H$^+$): 751.3.

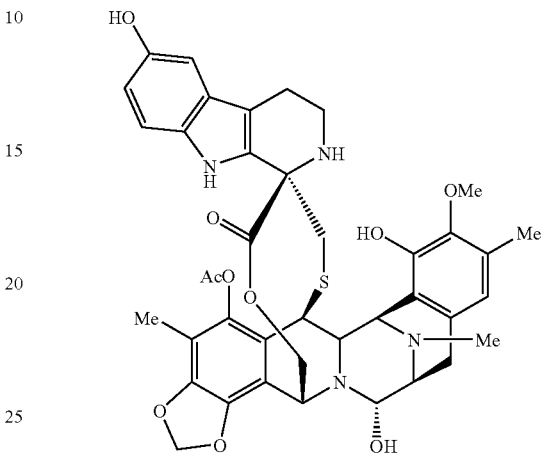

Compound 31: $^1$H-NMR (300 MHz, CDCl$_3$): δ 7.60 (s, 1H); 7.00 (d, 1H); 6.69 (d, 1H); 6.66 (s, 1H); 6.69 (dd, 1H); 6.16 (s, 1H); 5.96 (s, 1H); 5.78 (s, 1H); 5.19 (d, 1H); 4.82 (s, 1H); 4.49 (d, 1H); 4.46 (s, 1H); 4.17 (d, 1H); 4.10 (d, 1H); 3.81 (s, 3H); 3.72-3.59 (m, 2H); 3.64 (d, 2H); 3.50 (d, 1H); 3.23-2.76 (m, 4H); 2.55-2.29 (m, 3H); 2.37 (s, 3H); 2.25 (s, 3H); 2.19 (s, 3H); 2.03 (s, 3H).

$^{13}$C-NMR (75 MHz, CDCl$_3$): δ 171.3, 166.9, 149.2, 147.9, 145.4, 142.9, 141.0, 140.7, 131.2, 130.7, 127.5, 121.2, 120.9, 115.5, 111.5, 103.1, 101.8, 81.9, 62.3, 61.8, 60.3, 57.7, 57.4, 55.8, 54.9, 42.1, 41.2, 39.6, 39.1, 29.6, 23.5, 22.6, 21.4, 20.5, 15.8, 14.1, 9.6.

ESI-MS m/z: Calcd. for $C_{40}H_{42}N_4O_{10}S$: 770.3 Found (M–H$_2$O+H$^+$): 753.3.

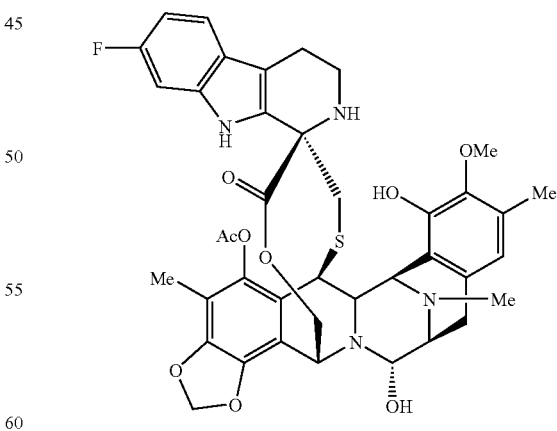

Compound 32: $^1$H-NMR (300 MHz, CDCl$_3$): δ 7.72 (s, 1H); 7.27 (dd, 1H); 6.94 (dd, 1H); 6.76 (ddd, 1H); 6.66 (s, 1H); 6.20 (s, 1H); 5.99 (s, 1H); 5.75 (s, 1H); 5.19 (d, 1H); 4.83 (s, 1H); 4.49 (d, 1H); 4.16-4.09 (m, 2H); 3.81 (s, 3H); 3.50-3.48 (m, 1H); 3.48 (s, 1H); 3.22-2.79 (m, 5H); 2.65-2.51 (m, 3H); 2.37 (s, 3H); 2.25 (s, 3H); 2.19 (s, 3H); 2.05 (s, 3H).

$^{13}$C-NMR (75 MHz, CDCl$_3$): δ 171.5, 169.0, 148.1, 145.7, 143.1, 141.3, 140.9, 131.5, 129.3, 123.7, 121.5, 121.1, 119.3, 119.1, 118.3, 115.7, 110.4, 108.2, 107.8, 102.0, 97.8, 97.5, 82.1, 62.4, 62.1, 60.5, 57.9, 57.6, 56.1, 55.1, 42.4, 41.5, 39.9, 39.4, 29.9, 23.8, 21.7, 20.8, 16.0, 9.9.

ESI-MS m/z: Calcd. for C$_{40}$H$_{41}$FN$_4$O$_9$S: 772.3 Found (M–H$_2$O+H$^+$): 755.3.

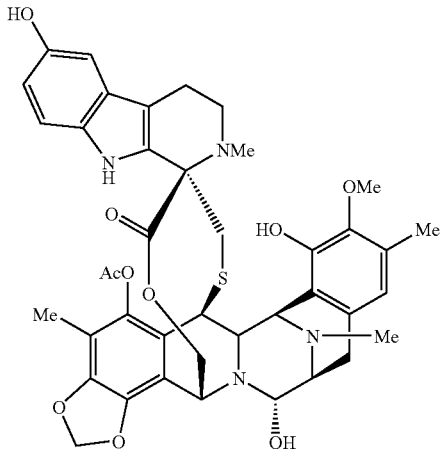

Compound 33: $^1$H-NMR (300 MHz, CDCl$_3$): δ 6.85 (d, 1H); 6.80 (s, 1H); 6.71-6.64 (m, 2H); 6.48 (s, 1H); 6.18 (s, 1H); 6.02 (s, 1H); 5.74 (s, 1H); 5.03 (d, 1H); 4.88 (d, 1H); 4.39 (d, 1H); 4.36 (s, 1H); 4.16 (d, 1H); 3.98 (dd, 1H); 3.80 (s, 3H); 3.71 (d, 1H); 3.48 (s, 1H); 3.22 (d, 1H); 2.93-2.83 (m, 2H); 2.73-2.39 (m, 4H); 2.29 (s, 3H); 2.28-2.05 (m, 1H); 2.26 (s, 3H); 2.22 (s, 3H); 2.18 (s, 3H); 2.03 (s, 3H).

$^{13}$C-NMR (75 MHz, CDCl$_3$): δ 168.9, 149.3, 147.6, 145.5, 142.7, 141.6, 140.7, 131.3, 131.1, 129.3, 126.9, 121.2, 115.7, 111.9, 111.0, 110.7, 103.1, 102.0, 83.4, 69.8, 63.7, 60.2, 58.5, 57.7, 55.1, 54.7, 59.5, 43.1, 41.4, 40.6, 35.0, 29.6, 24.6, 22.6, 21.1, 20.2, 15.5, 9.7.

ESI-MS m/z: Calcd. for C$_{41}$H$_{44}$N$_4$O$_{10}$S: 784.3 Found (M–H$_2$O+H$^+$): 767.3.

Compound 34: $^1$H-NMR (300 MHz, CDCl$_3$): δ 7.58 (s, 1H); 7.23 (d, 1H); 6.76 (d, 1H); 6.67 (dd, 1H); 6.66 (s, 1H); 6.19 (d, 1H); 5.98 (s, 1H); 5.74 (s, 1H); 5.20 (d, 1H); 4.82 (s, 1H); 4.49 (d, 1H); 4.47 (s, 1H); 4.16 (d, 1H); 4.10 (dd, 1H); 3.81 (s, 3H); 3.78 (s, 3H); 3.51-3.47 (m, 1H); 3.22-2.80 (m, 5H); 2.65-2.50 (m, 3H); 2.36 (s, 3H); 2.25 (s, 3H); 2.19 (s, 3H); 2.05 (s, 3H).

$^{13}$C-NMR (75 MHz, CDCl$_3$): δ 171.7, 168.9, 156.5, 148.1, 145.6, 143.1, 141.3, 140.9, 136.5, 131.5, 129.8, 129.3, 121.6, 121.5, 121.2, 119.2, 115.8, 113.1, 110.3, 109.3, 102.2, 94.9, 82.2, 62.5, 62.0, 60.5, 57.9, 57.7, 56.1, 55.8, 55.2, 42.3, 41.5, 40.0, 39.5, 29.9, 23.8, 21.8, 20.8, 16.0, 9.9.

ESI-MS m/z: Calcd. for C$_{41}$H$_{44}$N$_4$O$_{10}$S: 784.3 Found (M–H$_2$O+H$^+$): 767.3.

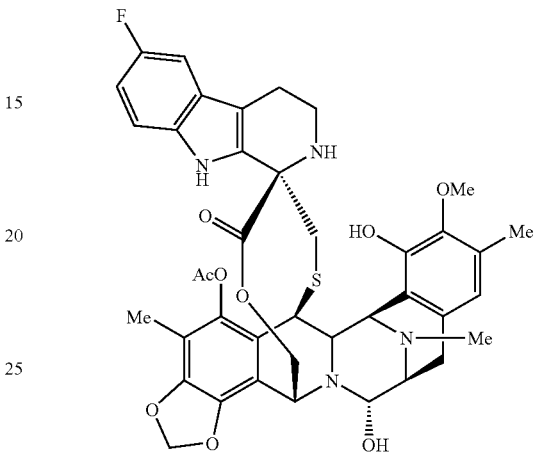

Compound 35: $^1$H-NMR (300 MHz, CDCl$_3$): δ 7.73 (s, 1H); 7.15 (dd, 1H); 7.00 (dd, 1H); 6.81 (ddd, 1H); 6.67 (s, 1H); 6.20 (d, 1H); 5.99 (d, 1H); 5.76 (s, 1H); 5.19 (d, 1H); 4.83 (s, 1H); 4.49 (d, 2H); 4.17 (d, 1H); 4.12 (dd, 1H); 3.81 (s, 3H); 3.65-3.64 (m, 1H); 3.50 (d, 1H); 3.24-2.12 (m, 2H); 3.00 (d, 1H); 2.89-2.80 (m, 2H); 2.66-2.45 (m, 3H); 2.37 (s, 3H); 2.25 (s, 3H); 2.20 (s, 3H); 2.05 (s, 3H).

$^{13}$C-NMR (75 MHz, CDCl$_3$): δ 171.4, 169.0, 159.4, 156.3, 148.1, 145.7, 143.1, 141.3, 140.9, 138.0, 132.2, 129.4, 127.4, 127.3, 121.4, 121.2, 118.2, 115.7, 113.1, 111.8, 111.7, 110.4, 110.1, 103.7, 103.4, 102.0, 82.1, 62.5, 62.1, 60.5, 57.9, 57.6, 56.1, 55.1, 42.3, 41.4, 39.9, 39.4, 29.9, 23.8, 21.7, 20.8, 16.0, 9.9.

ESI-MS m/z: Calcd. for C$_{40}$H$_{41}$FN$_4$O$_9$S: 772.2 Found (M–H$_2$O+H$^+$): 755.2.

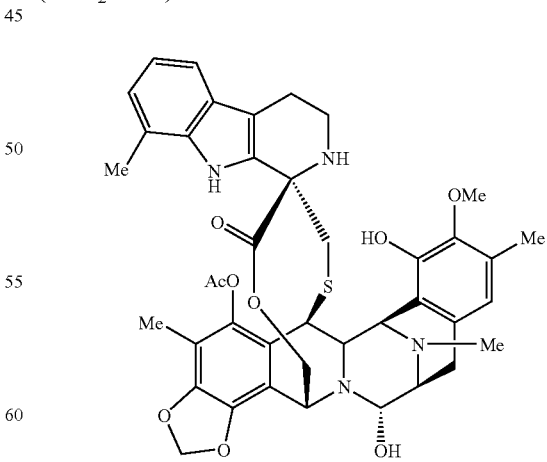

Compound 36: $^1$H-NMR (300 MHz, CDCl$_3$): δ 7.47 (s, 1H); 7.22 (d, 1H); 6.95-6.87 (m, 2H); 6.66 (s, 1H); 6.13 (d, 1H); 6.01 (d, 1H); 5.76 (s, 1H); 5.20 (d, 1H); 4.84 (s, 1H); 4.49 (d, 1H); 4.46 (s, 1H); 4.18-4.14 (m, 2H); 3.81 (s, 3H); 3.54 (d, 1H); 3.48 (s, 1H); 3.22 (d, 1H); 3.20-2.80 (m, 4H); 2.70-2.42 (m, 3H); 2.36 (s, 6H); 2.27 (s, 3H); 2.18 (s, 3H); 2.05 (s, 3H).

$^{13}$C-NMR (75 MHz, CDCl$_3$): δ 171.3, 169.0, 148.0, 145.6, 143.1, 141.4, 140.9, 135.3, 131.5, 131.1, 130.7, 129.4, 126.6, 122.8, 121.8, 121.3, 119.9, 119.6, 118.1, 116.3, 115.8, 102.0, 82.1, 62.1, 60.5, 58.0, 57.8, 56.1, 55.1, 42.4, 41.5, 40.1, 39.6, 29.9, 23.9, 21.9, 20.7, 16.6, 16.0, 9.9.

ESI-MS m/z: Calcd. for C$_{41}$H$_{44}$N$_4$O$_9$S: 768.2 Found (M−H$_2$O+H$^+$): 751.2.

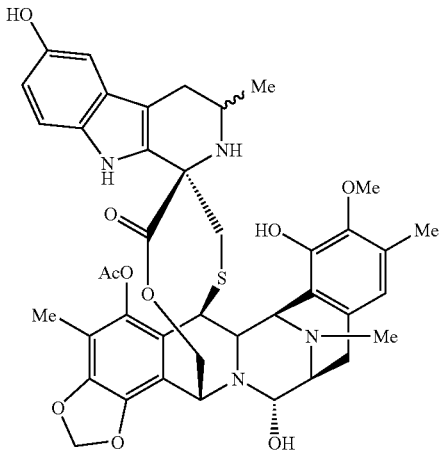

Compound 37 (first isomer): $^1$H-NMR (300 MHz, CDCl$_3$): δ 7.70 (s, 1H); 7.06 (d, 1H); 6.67-6.61 (m, 3H); 6.20 (d, 1H); 5.98 (d, 1H); 5.70 (s, 1H); 5.20 (d, 1H); 4.86 (s, 1H); 4.53 (d, 1H); 4.48 (s, 1H); 4.18 (s, 1H); 3.80 (s, 3H); 3.72-3.54 (m, 4H); 3.24-3.22 (m, 1H); 3.01-2.56 (m, 5H); 2.31 (s, 3H); 2.27 (s, 3H); 2.15 (s, 3H); 2.02 (s, 3H); 1.10 (d, 3H).

ESI-MS m/z: Calcd. for C$_{41}$H$_{44}$N$_4$O$_{10}$S: 784.3 Found (M−H$_2$O+H$^+$): 767.3.

Compound 38 (second isomer): $^1$H-NMR (300 MHz, CDCl$_3$): δ 7.51 (s, 1H); 7.10 (d, 1H); 6.75 (d, 1H); 6.64 (dd, 1H); 6.59 (s, 1H); 6.19 (d, 1H); 5.97 (d, 1H); 5.71 (s, 1H); 5.15 (d, 1H); 4.84 (s, 1H); 4.53-4.50 (m, 2H); 4.16 (s, 1H); 4.04 (dd, 1H); 3.80 (s, 3H); 3.65-3.63 (m, 1H); 3.51-3.49 (m, 1H); 3.40-2.36 (m, 1H); 3.24-3.21 (m, 1H); 3.03-2.84 (m, 2H); 2.50-2.41 (m, 2H); 2.32 (s, 3H); 2.23 (s, 3H); 2.16 (s, 3H); 2.06 (s, 3H); 1.20 (d, 3H).

ESI-MS m/z: Calcd. for C$_{41}$H$_{44}$N$_4$O$_{10}$S: 784.3 Found (M−H$_2$O+H$^+$): 767.3.

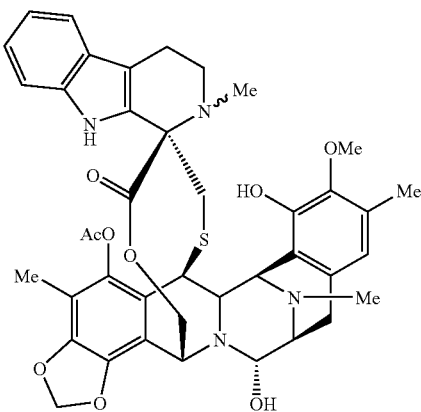

Compound 39 (first isomer): $^1$H-NMR (300 MHz, CDCl$_3$): δ 8.09 (s, 1H); 7.41 (d, 1H); 7.17 (t, 1H); 7.03 (t, 1H); 6.87 (d, 1H); 6.83 (s, 1H); 6.13 (d, 1H); 5.98 (d, 1H); 5.69 (s, 1H); 5.02 (d, 1H); 4.88 (s, 1H); 4.55-4.16 (m, 4H); 3.64-3.56 (m, 1H); 3.61 (s, 3H); 3.31-3.29 (m, 1H); 3.22-2.80 (m, 3H); 2.68-2.46 (m, 3H); 2.41 (s, 3H); 2.27 (s, 3H); 2.20 (s, 3H); 2.07 (s, 3H); 1.99 (s, 3H).

ESI-MS m/z: Calcd. for C$_{41}$H$_{44}$N$_4$O$_9$S: 768.2 Found (M−H$_2$O+H$^+$): 751.2.

Compound 40 (second isomer): $^1$H-NMR (300 MHz, CDCl$_3$): δ7.36 (d, 1H); 7.12-7.05 (m, 2H); 7.00 (ddd, 1H); 6.92 (s, 1H); 6.48 (s, 1H); 6.20 (d, 1H); 6.06 (d, 1H); 5.70 (s, 1H); 5.04 (d, 1H); 4.88 (s, 1H); 4.39-4.36 (m, 1H); 4.15 (d, 1H); 3.98 (dd, 1H); 3.80 (s, 3H); 3.72-3.64 (m, 2H); 3.21 (d, 1H); 2.95-2.84 (m, 2H); 2.73-2.55 (m, 4H); 2.29 (s, 3H); 2.26 (s, 3H); 2.23 (s, 3H); 2.18 (s, 3H); 2.03 (s, 3H).

$^{13}$C-NMR (75 MHz, CDCl$_3$): δ 169.1, 167.5, 147.9, 145.7, 142.9, 141.9, 140.9, 136.0, 131.6, 129.4, 126.5, 122.5, 122.1, 121.5, 119.5, 118.7, 116.0, 111.5, 110.6, 102.2, 83.7, 63.9, 60.4, 58.8, 57.9, 55.4, 54.9, 49.7, 43.4, 41.7, 40.8, 32.1, 29.5, 24.9, 22.9, 21.5, 20.5, 15.8, 14.3, 9.9.

ESI-MS m/z: Calcd. for C$_{41}$H$_{44}$N$_4$O$_9$S: 768.2 Found (M−H$_2$O+H$^+$): 751.2.

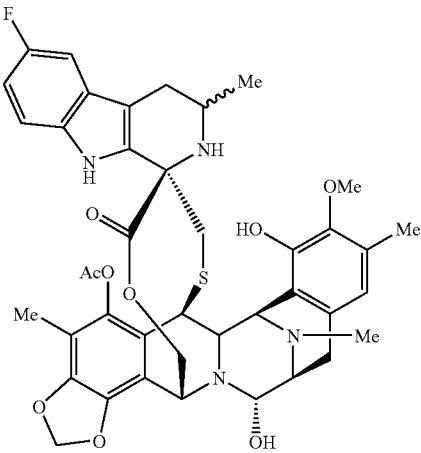

Compound 41 (first isomer): $^1$H-NMR (300 MHz, CDCl$_3$): δ 7.84 (s, 1H); 7.13 (dd, 1H); 6.96 (dd, 1H); 6.81 (ddd, 1H); 6.62 (s, 1H); 6.20 (d, 1H); 5.99 (d, 1H); 5.70 (s, 1H); 5.19 (d, 1H); 4.86 (s, 1H); 4.52 (d, 1H); 4.50 (s, 1H); 4.16 (d, 1H); 3.80 (s, 3H); 3.53 (d, 1H); 3.49-3.48 (m, 1H); 3.23 (d, 1H); 3.00-2.71 (m, 3H); 2.62-2.41 (m, 2H); 2.31 (s, 3H); 2.27 (s, 3H); 2.14 (s, 3H); 2.02 (s, 3H); 1.13 (d, 3H).

$^{13}$C-NMR (75 MHz, CDCl$_3$): δ 170.5, 168.9, 159.4, 156.2, 147.6, 145.8, 143.0, 141.2, 133.2, 132.2, 131.7, 131.1, 129.2, 129.0, 127.3, 121.7, 115.6, 111.7, 111.6, 110.3, 109.9, 103.7, 103.4, 102.0, 81.8, 64.0, 62.0, 60.5, 58.0, 56.1, 55.3, 44.0, 42.4, 41.5, 38.1, 32.1, 29.5, 24.0, 22.9, 21.7, 20.7, 16.2, 14.3, 9.9.

ESI-MS m/z: Calcd. for C$_{41}$H$_{43}$FN$_4$O$_9$S: 786.2 Found (M−H$_2$O+H$^+$): 769.3.

Compound 42 (second isomer): $^1$H-NMR (300 MHz, CDCl$_3$): δ 7.62 (s, 1H); 7.18 (dd, 1H); 6.99 (dd, 1H); 6.82 (ddd, 1H); 6.59 (s, 1H); 6.20 (d, 1H); 5.98 (d, 1H); 5.71 (s, 1H); 5.15 (d, 1H); 4.85 (s, 1H); 4.52 (s, 1H); 4.50 (d, 1H); 4.16 (d, 1H); 4.05 (dd, 1H); 3.80 (s, 3H); 3.50-3.48 (m, 1H); 3.42-3.36 (m, 1H); 3.23 (d, 1H); 3.00-2.81 (m, 2H); 2.50 (dd, 1H); 2.44 (d, 1H); 2.32 (s, 3H); 2.24 (s, 3H); 2.16 (s, 3H); 2.07 (s, 3H); 1.23 (d, 3H).

$^{13}$C-NMR (75 MHz, CDCl$_3$): δ 171.9, 168.7, 156.2, 147.8, 145.6, 143.3, 141.8, 140.9, 132.7, 131.4, 131.1, 129.4, 129.0, 121.8, 121.4, 115.8, 113.1, 111.9, 111.8, 110.4, 110.0, 103.7, 103.4, 102.0, 81.9, 63.4, 61.8, 60.6, 58.0, 56.2, 55.2, 46.6, 42.3, 41.5, 41.0, 32.1, 29.5, 23.9, 22.9, 21.9, 20.7, 16.1, 14.3, 9.9.

ESI-MS m/z: Calcd. for C$_{41}$H$_{43}$FN$_4$O$_9$S: 786.2 Found (M−H$_2$O+H$^+$): 769.3.

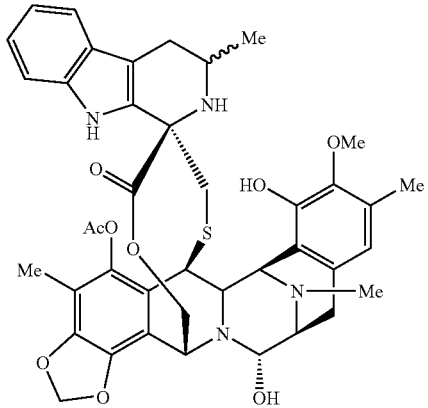

Compound 43 (first isomer): $^1$H-NMR (300 MHz, CDCl$_3$): δ 7.85 (s, 1H); 7.33 (d, 1H); 7.23 (d, 1H); 7.07 (t, 1H); 6.99 (t, 1H); 6.63 (s, 1H); 6.22 (d, 1H); 6.00 (d, 1H); 5.70 (s, 1H); 5.20 (d, 1H); 4.86 (s, 1H); 4.52 (d, 1H); 4.48 (s, 1H); 4.16 (d, 1H); 3.80 (s, 3H); 3.53 (d, 1H); 3.22 (d, 1H); 3.01-2.73 (m, 3H); 2.62-2.48 (m, 2H); 2.39-2.17 (m, 1H); 2.31 (s, 3H); 2.27 (s, 3H); 2.14 (s, 3H); 2.02 (s, 3H); 1.14 (d, 3H).

$^{13}$C-NMR (75 MHz, CDCl$_3$): δ 170.6, 168.8, 147.6, 145.7, 143.0, 141.2, 135.7, 131.8, 131.3, 129.2, 127.0, 122.0, 121.8, 121.7, 119.3, 118.5, 115.6, 111.0, 110.2, 102.0, 81.8, 64.0, 61.9, 60.5, 58.1, 58.0, 56.1, 55.3, 44.0, 42.4, 41.5, 38.1, 32.1, 29.5, 24.0, 22.9, 21.8, 20.7, 16.2, 14.3, 9.9.

ESI-MS m/z: Calcd. for C$_{41}$H$_{44}$N$_4$O$_9$S: 768.2 Found (M−H$_2$O+H$^+$): 751.3.

Compound 44 (second isomer): $^1$H-NMR (300 MHz, CDCl$_3$): δ 7.62 (s, 1H); 7.36 (d, 1H); 7.27 (d, 1H); 7.09 (t, 1H); 7.00 (t, 1H); 6.59 (s, 1H); 6.21 (d, 1H); 5.98 (d, 1H); 5.71 (s, 1H); 5.15 (d, 1H); 4.84 (s, 1H); 4.51 (d, 2H); 4.17-4.16 (m, 1H); 4.05 (dd, 1H); 3.80 (s, 3H); 3.49-3.48 (m, 1H); 3.42-3.38 (m, 1H); 3.24-3.22 (m, 1H); 3.03-2.81 (m, 2H); 2.57 (dd, 1H); 2.46 (d, 1H); 2.32 (s, 3H); 2.24 (s, 3H); 2.17-2.12 (m, 1H); 2.16 (s, 3H); 2.07 (s, 3H); 1.23 (d, 3H).

ESI-MS m/z: Calcd. for C$_{41}$H$_{44}$N$_4$O$_9$S: 768.2 Found (M−H20+H$^+$): 751.3.

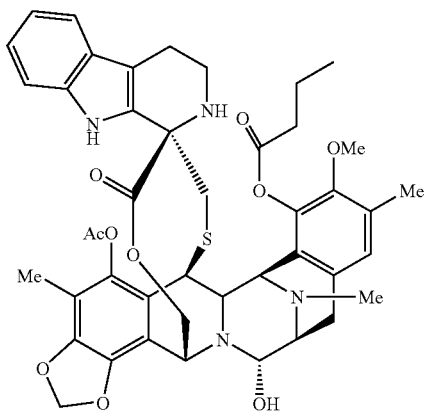

Compound 45: $^1$H-NMR (300 MHz, CDCl$_3$): δ 7.69 (s, 1H); 7.38 (d, 1H); 7.24 (d, 1H); 7.09 (ddd, 1H); 7.03 (s, 1H); 7.00 (ddd, 1H); 6.22 (d, 1H); 6.00 (d, 1H); 5.20 (d, 1H); 4.83 (s, 1H); 4.50 (s, 1H); 4.38 (s, 1H); 4.33 (s, 1H); 4.12 (dd, 1H); 3.77 (s, 3H); 3.68-3.66 (m, 1H); 3.51-3.49 (m, 1H); 3.24-2.85 (m, 4H); 2.70-2.49 (m, 2H); 2.62 (t, 2H); 2.37 (s, 3H); 2.28 (s, 3H); 2.15 (s, 3H); 2.06 (s, 3H); 1.94-1.83 (m, 2H); 1.10 (t, 3H).

ESI-MS m/z: Calcd. for C$_{44}$H$_{48}$N$_4$O$_{10}$S: 824.3 Found (M−H$_2$O+H$^+$): 807.2.

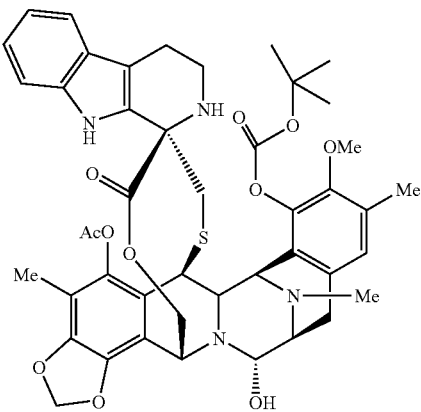

Compound 46: $^1$H-NMR (300 MHz, CDCl$_3$): 7.67 (s, 1H); 7.38 (d, 1H); 7.24 (d, 1H); 7.09 (ddd, 1H); 7.00 (ddd, 1H); 7.00 (s, 1H); 6.21 (d, 1H); 6.00 (d, 1H); 5.20 (d, 1H); 4.83 (s, 1H); 4.51 (d, 1H); 4.39 (s, 1H); 4.15 (d, 1H); 3.81 (s, 3H); 3.52 (d, 1H); 3.26 (d, 1H); 3.19-3.11 (m, 1H); 3.06-2.81 (m, 3H); 2.72-2.44 (m, 3H); 2.36 (s, 3H); 2.31 (s, 3H); 2.17 (s, 3H); 2.03 (s, 3H); 1.54 (s, 9H).

$^{13}$C-NMR (75 MHz, CDCl$_3$): δ 171.5, 169.2, 151.4, 148.2, 145.7, 144.4, 141.3, 140.9, 135.7, 131.4, 131.1, 130.9, 127.4, 127.1, 124.4, 122.1, 121.5, 119.4, 118.7, 115.6, 111.1, 102.0, 83.3, 81.8, 62.8, 61.9, 60.2, 57.8, 56.3, 56.1, 42.3, 41.5, 39.8, 39.4, 29.9, 27.8, 23.6, 21.7, 20.5, 16.0, 14.3, 9.9.

ESI-MS m/z: Calcd. for C$_{45}$H$_{50}$N$_4$O$_{11}$S: 854.3 Found (M−H$_2$O+H$^+$): 837.2.

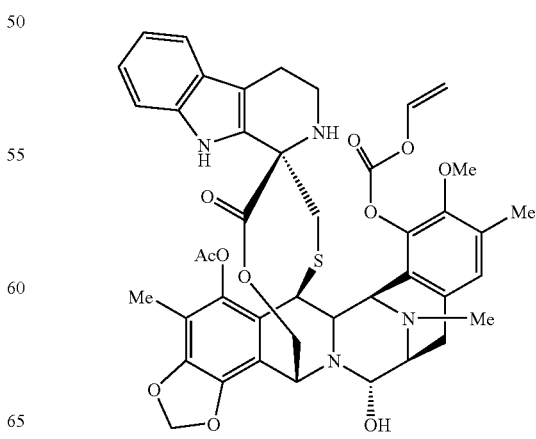

Compound 47: ¹H-NMR (300 MHz, CDCl₃): δ 7.68 (s, 1H); 7.38 (d, 1H); 7.24 (d, 1H); 7.19 (dd, 1H); 7.10 (ddd, 1H); 7.06 (s, 1H); 7.00 (ddd, 1H); 6.21 (d, 1H); 6.01 (d, 1H); 5.20 (d, 1H); 5.00 (dd, 1H); 4.83 (s, 1H); 4.70 (d, 1H); 4.51 (s, 1H); 4.40 (d, 1H); 4.15 (dd, 1H); 3.83 (dd, 1H); 3.82 (s, 3H); 3.53 (d, 1H); 3.28-3.03 (m, 3H); 2.94-2.83 (m, 2H); 2.72-2.46 (m, 3H); 2.38 (s, 3H); 2.33 (s, 3H); 2.17 (s, 3H); 2.07 (s, 3H).

¹³C-NMR (75 MHz, CDCl₃): δ 171.5, 169.0, 150.8, 148.0, 145.8, 144.0, 143.1, 141.3, 140.9, 135.7, 130.8, 128.2, 127.1, 122.2, 120.0, 119.5, 118.7, 115.5, 113.3, 111.1, 110.5, 102.1, 98.7, 81.9, 62.8, 62.0, 60.5, 57.7, 56.2, 56.0, 42.3, 41.8, 39.9, 39.5, 32.1, 29.5, 23.7, 21.8, 20.5, 16.0, 14.3, 9.9.

ESI-MS m/z: Calcd. for $C_{43}H_{44}N_4O_{11}S$: 824.2 Found (M−H₂O+H⁺): 807.2.

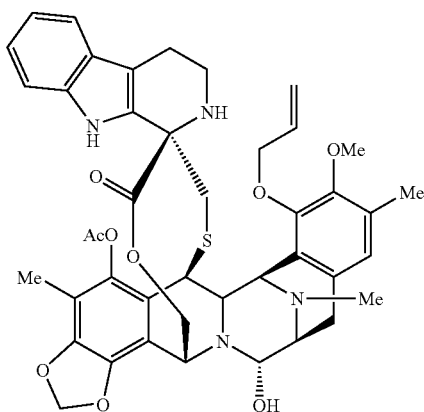

Compound 48: ¹H-NMR (300 MHz, CDCl₃): δ 7.70 (s, 1H); 7.37 (d, 1H); 7.24 (d, 1H); 7.08 (ddd, 1H); 7.00 (ddd, 1H); 6.87 (s, 1H); 6.20 (d, 1H); 6.17-6.05 (m, 1H); 5.99 (d, 1H); 5.47 (dd, 1H); 5.25 (dd, 1H); 5.21 (d, 1H); 4.82 (s, 1H); 4.81 (dd, 1H); 4.50 (d, 1H); 4.44 (s, 1H); 4.36 (dd, 1H); 4.13 (dd, 1H); 4.11 (s, 1H); 3.84 (s, 3H); 3.51 (d, 1H); 3.24-3.00 (m, 3H); 2.89-2.80 (m, 2H); 2.73-2.48 (m, 3H); 2.33 (s, 3H); 2.31-2.26 (m, 1H); 2.23 (s, 3H); 2.19 (s, 3H); 2.05 (s, 3H).

¹³C-NMR (75 MHz, CDCl₃): δ 171.3, 168.6, 150.5, 148.6, 145.3, 140.9, 140.6, 135.5, 134.6, 131.0, 130.7, 126.7, 124.7, 121.7, 121.3, 119.0, 118.3, 116.2, 118.4, 110.8, 109.9, 101.7, 81.6, 72.6, 62.4, 61.6, 59.3, 57.6, 57.5, 55.9, 55.1, 42.0, 41.3, 39.4, 39.0, 29.2, 23.5, 22.5, 21.4, 20.3, 15.7, 14.0, 9.9.

ESI-MS m/z: Calcd. for $C_{43}H_{46}N_4O_9S$: 794.3 Found (M−H₂O+H⁺): 777.2.

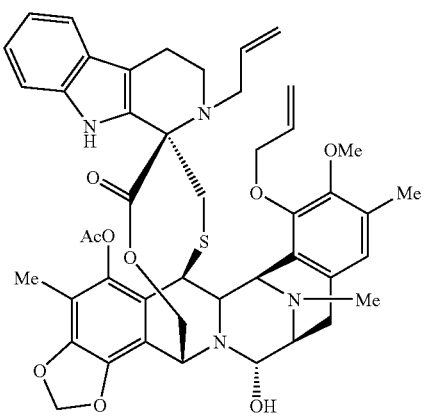

Compound 49: ¹H-NMR (300 MHz, CDCl₃): δ 7.60 (s, 1H); 7.42-7.39 (m, 2H); 7.09-7.00 (m, 2H); 6.81 (s, 1H); 6.16-6.04 (m, 2H); 6.07 (s, 1H); 5.99 (s, 1H); 5.52-5.43 (m, 2H); 5.24 (d, 1H); 5.11 (d, 1H); 4.96 (d, 1H); 4.80-4.32 (m, 6H); 4.13-4.10 (m, 2H); 3.81 (s, 3H); 3.58-3.56 (m, 1H); 3.46-3.40 (m, 1H); 3.24-3.20 (m, 1H); 2.99-2.87 (m, 2H); 2.67-2.53 (m, 2H); 2.31 (s, 3H); 2.23 (s; 3H); 2.19 (s, 3H); 2.02 (s, 3H).

ESI-MS m/z: Calcd. for $C_{46}H_{50}N_4O_9S$: 834.3 Found (M−H₂O+H⁺): 817.2.

Scheme 2

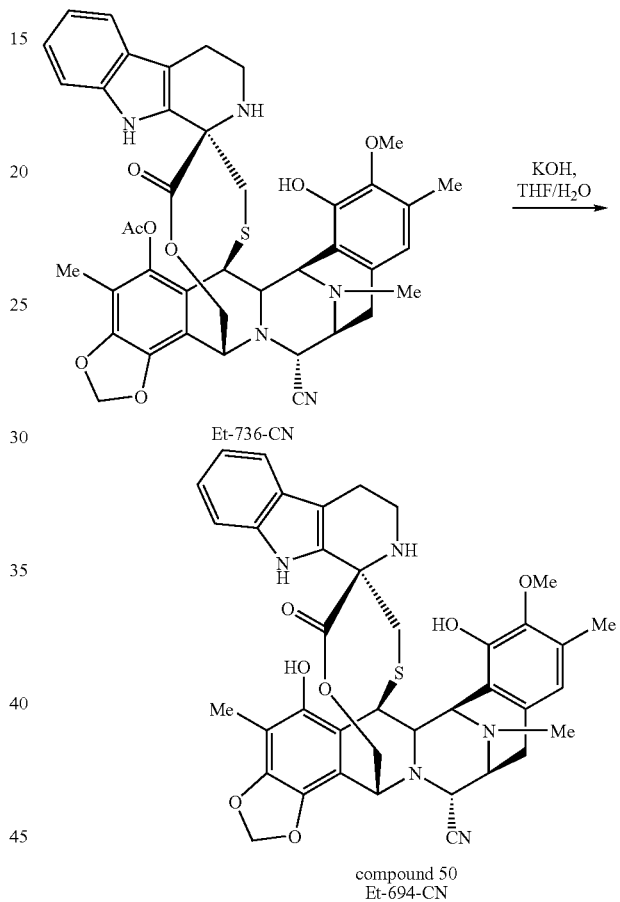

To a solution of ET-736-CN in THF/H₂O 3:1 (0.027M) were added 15 equiv. of KOH. The reaction mixture was stirred at room temperature for 5 h. After this time the reaction was quenched with an aqueous saturated solution of NaCl, extracted with CH₂Cl₂. The organic layer was dried over Na₂SO₄. Chromatography gives pure compound 50.

¹H-NMR (300 MHz, CDCl₃): δ 7.59 (s, 1H); 7.40 (d, 1H); 7.25 (d, 1H); 7.11 (ddd, 1H); 7.02 (ddd, 1H); 6.67 (s, 1H); 6.16 (d, 1H); 5.93 (d, 1H); 5.90 (s, 1H); 5.62 (s, 1H); 5.06 (d, 1H); 4.46 (d, 1H); 4.36 (s, 1H); 4.31 (dd, 1H); 4.19 (d, 1H); 4.12 (dd, 1H); 3.82 (s, 3H); 3.55 (d, 1H); 3.42 (d, 1H); 3.20-2.80 (m, 4H); 2.69-2.53 (m, 3H); 2.38 (s, 3H); 2.21 (s, 3H); 2.18 (s, 3H).

ESI-MS m/z: Calcd. for $C_{39}H_{39}N_5O_7S$: 721.3 Found (M+H⁺): 722.2.

Derivatives of Et-694:

Method 5: To a solution of 1 equiv. of ET-694-CN, compound 50 in CH₂Cl₂ (0.032M) under argon at room temperature were added 2 equiv. of pyridine and 2 equiv. of acid chloride, chlorofomiate or anhydride. The reaction was followed by TLC and quenched with an aqueous saturated solution of NaHCO$_3$, extracted with CH$_2$Cl$_2$ and the organic layers dried over Na$_2$SO$_4$. Flash chromatography gives pure compounds.

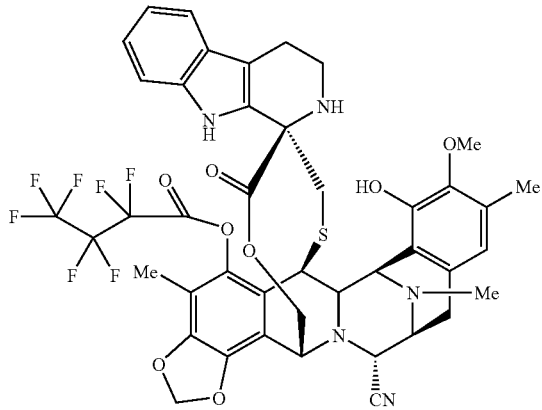

Compound 51: $^1$H-NMR (300 MHz, CDCl$_3$): δ 7.65 (s, 1H); 7.40 (d, 1H); 7.26 (d, 1H); 7.12 (s, 1H); 7.11 (ddd, 1H); 7.04 (ddd, 1H); 6.30 (d, 1H); 6.19 (d, 1H); 5.10 (d, 1H); 4.40-4.30 (m, 2H); 4.23-4.16 (m, 1H); 3.76 (s, 3H); 3.50-3.44 (m, 2H); 3.19-3.13 (m, 2H); 3.03-2.83 (m, 2H); 2.66-2.47 (m, 3H); 2.40 (s, 3H); 3.36-2.22 (m, 2H); 2.16 (s, 3H); 2.07 (s, 3H).

ESI-MS m/z: Calcd. for C$_{43}$H$_{38}$F$_7$N$_5$O$_8$S: 917.2 Found (M+H$^+$): 918.1.

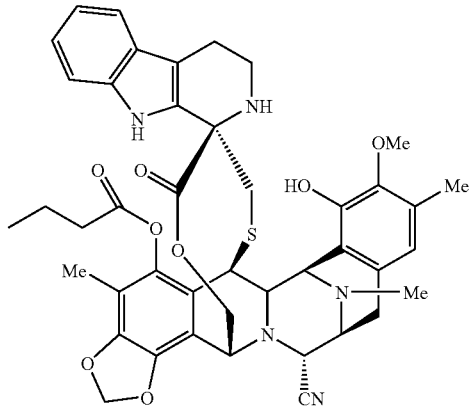

Compound 52: $^1$H-NMR (300 MHz, CDCl$_3$): δ 7.72 (d, 1H), 7.38 (d, 1H), 7.26 (d, 1H), 7.10 (t, 1H). 7.00 (t, 1H), 6.65 (s, 1H), 6.24 (d, 1H), 6.02 (d, 1H), 5.74 (s, 1H), 5.08 (d, 1H), 4.54 (broad s, 1H), 4.33 (s, 1H), 4.27 (d, 1H), 4.21 (s, 1H), 4.20 (d, 1H), 3.80 (s, 3H), 3.43 (m, 2H), 3.20-2.81 (m, 4H), 2.64-2.58 (m, 3H), 2.53 (t, 2H), 2.37 (s, 3H), 2.26 (m, 1H), 2.21 (s, 3H), 2.05 (s, 3H), 1.74 (sext, 2H), 1.01 (t, 3H).

ESI-MS m/z: Calcd. for C$_{43}$H$_{45}$N$_5$O$_8$S: 791.3 Found (M+H$^+$): 792.2.

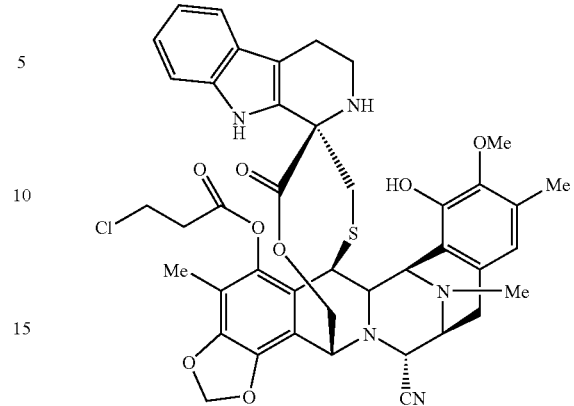

Compound 53: $^1$H-NMR (300 MHz, CDCl$_3$): δ 7.71 (s, 1H), 7.39 (d, 1H), 7.26 (d, 1H), 7.11 (t, 1H), 7.02 (t, 1H), 6.66 (s, 1H), 6.26 (s, 1H), 6.04 (s, 1H), 5.80 (s, 1H), 5.09 (d, 1H), 4.52 (broad s, 1H), 4.34 (s, 1H), 4.27 (d, 1H), 4.22 (d, 1H), 4.20 (m, 1H), 3.82 (s, 3H), 3.79 (m, 2H), 3.42 (m, 2H), 3.16 (m, 1H), 3.07-2.81 (m, 5H), 2.64-2.50 (m, 3H), 2.37 (s, 3H), 2.25 (m, 1H), 2.21 (s, 3H), 2.08 (s, 3H).

ESI-MS m/z: Calcd. for C$_{42}$H$_{42}$ClN$_5$O$_8$S: 811.2 Found (M+H$^+$): 812.2.

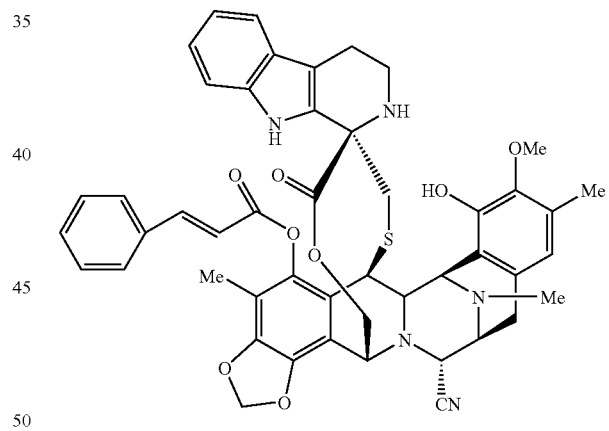

Compound 54: This product was obtained with 4 equiv. of cinnamoyl chloride and 4 equiv. of pyridine.

$^1$H-NMR (300 MHz, CDCl$_3$): δ 7.83 (d, 1H), 7.75 (s, 1H), 7.58 (m, 2H), 7.46 (m, 3H), 7.39 (d, 1H), 7.27 (d, 1H), 7.11 (t, 1H), 7.02 (t, 1H), 6.61 (s, 1H), 6.58 (d, 1H), 6.26 (s, 1H), 6.05 (s, 1H), 5.52 (s, 1H), 5.09 (d, 1H), 4.60 (broad s, 1H), 4.37 (s, 1H), 4.27 (d, 1H), 4.25 (s, 1H), 4.23 (m, 1H), 3.47 (s, 3H), 3.45 (m, 2H), 3.15 (m, 1H), 3.04 (d, 1H), 2.96 (m, 1H), 2.84 (m, 1H), 2.70-2.53 (m, 3H), 2.33 (m, 1H), 2.29 (s, 3H), 2.21 (s, 3H), 2.12 (s, 3H).

ESI-MS m/z: Calcd. for C$_{48}$H$_{45}$N$_5$O$_8$S: 851.3 Found (M+H$^+$): 852.2.

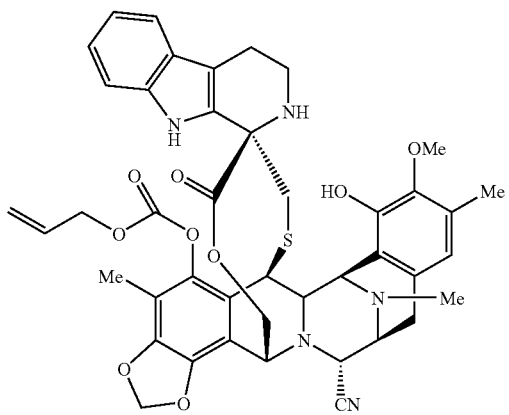
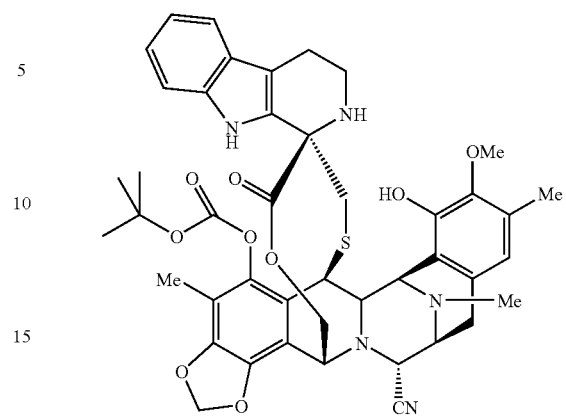

Compound 55: This product was obtained with 6 equiv. of allylchloroformiate and 6 equiv. of pyridine.

$^1$H-NMR (300 MHz, CDCl$_3$): δ 7.74 (s, 1H), 7.39 (d, 1H), 7.25 (d, 1H), 7.10 (t, 1H), 7.01 (t, 1H), 6.65 (s, 1H), 6.25 (s, 1H), 6.03 (s, 1H), 5.90 (ddd, 1H), 5.78 (s, 1H), 5.37 (d, 1H), 5.24 (d, 1H), 5.08 (d, 1H), 4.61 (m, 3H), 4.32 (s, 1H), 4.28 (d, 1H), 4.22 (s, 1H), 4.20 (d, 1H), 3.80 (s, 3H), 3.42 (m, 2H), 3.18 (m, 1H), 3.09-2.81 (m, 3H), 2.59 (m, 3H), 2.37 (s, 3H), 2.26 (m, 1H), 2.21 (s, 3H), 2.12 (s, 3H).

ESI-MS m/z: Calcd. for C$_{43}$H$_{43}$N$_5$O$_9$S: 805.3 Found (M+H$^+$): 806.3

Compound 57: $^1$H-NMR (300 MHz, CDCl$_3$): δ 7.74 (s, 1H), 7.40 (d, 1H), 7.27 (d, 1H), 7.11 (t, 1H), 7.02 (t, 1H), 6.65 (s, 1H), 6.23 (s, 1H), 6.02 (s, 1H), 5.74 (s, 1H), 5.09 (d, 1H), 4.66 (s, 1H), 4.32-4.21 (m, 4H), 3.81 (s, 3H), 3.40 (m, 2H), 3.21-2.86 (m, 3H), 2.80 (m, 1H), 2.64 (m, 3H), 2.37 (s, 3H), 2.29 (m, 1H), 2.21 (s, 3H), 2.11 (s, 3H), 1.45 (s, 9H).

ESI-MS m/z: Calcd. for C$_{44}$H$_{47}$N$_5$O$_9$S: 821.3 Found (M+H$^+$): 822.0.

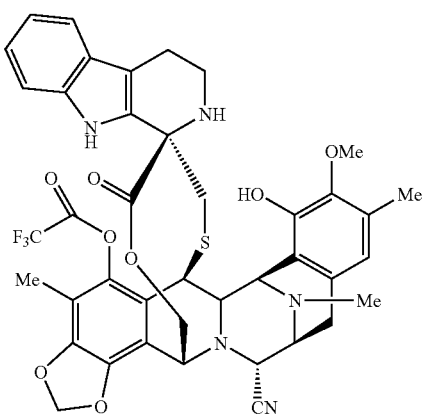
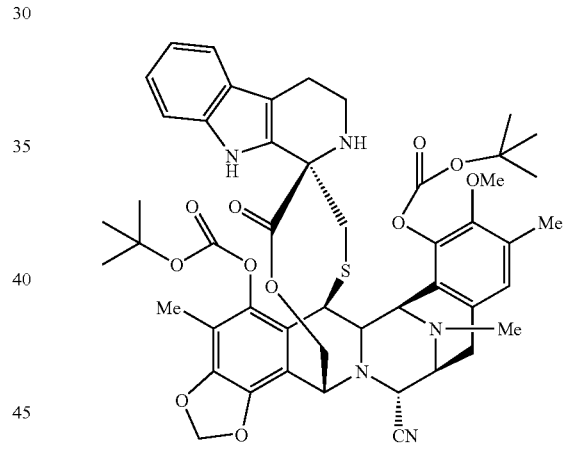

Compound 56: This product was obtained with 3 equiv. of trifluoroacetic anhydride and 3 equiv. of pyridine $^1$H-NMR (300 MHz, CDCl$_3$): δ 7.66 (s, 1H), 7.40 (d, 1H), 7.26 (d, 1H), 7.11 (t, 1H), 7.02 (t, 1H), 6.65 (s, 1H), 6.31 (d, 1H), 6.08 (d, 1H), 5.74 (s, 1H), 5.11 (d, 1H), 4.55 (s, 1H), 4.36 (s, 1H), 4.28 (d, 1H), 4.25 (s, 1H), 4.23 (d, 1H), 3.79 (s, 3H), 3.46 (m, 2H), 3.15 (m, 1H), 3.09-2.46 (m, 6H), 2.36 (s, 3H), 2.23 (s, 3H), 2.20 (m, 1H), 2.01 (s, 3H).

ESI-MS m/z: Calcd. for C$_{41}$H$_{38}$F$_3$N$_5$O$_8$S: 817.2 Found (M+H$^+$): 818.2

Compound 58: $^1$H-NMR (300 MHz, CDCl$_3$): δ 7.72 (s, 1H), 7.39 (d, 1H), 7.26 (d, 1H); 7.11 (t, 1H), 7.02 (t, 1H), 6.99 (s, 1H), 6.24 (s, 1H), 6.03 (s, 1H), 5.09 (d, 1H), 4.61 (s, 1H), 4.30 (s, 1H), 4.20 (m, 2H), 3.98 (s, 1H), 3.83 (s, 3H), 3.45 (m, 2H), 3.21-2.90 (m, 3H), 2.80 (m, 1H), 2.59 (s, 3H), 2.36 (s, 3H), 2.31 (m, 1H), 2.20 (s, 3H), 2.12 (s, 3H), 1.54 (s, 9H), 1.45 (s, 9H).

ESI-MS m/z: Calcd. for C$_{49}$H$_{55}$N$_5$O$_{11}$S: 921.4 Found (M+H$^+$): 922.3.

The monoBoc derivative in C-5 was obtained with 6 equiv. of Boc anhydride and 6 equiv of pyridine. With these conditions traces of diBoc derivative in C-5 and C-18 was isolated as a secondary product. This last compound can be obtained as the major product when the reaction was performed with TEA as base.

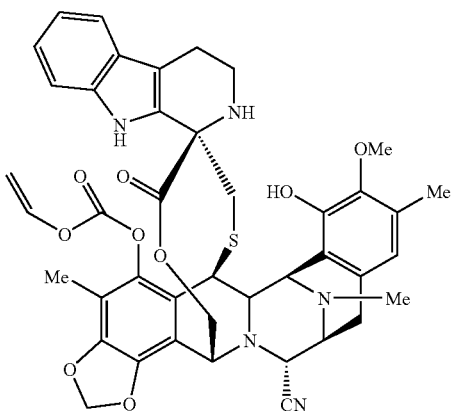

Compound 59: $^1$H-NMR (300 MHz, CDCl$_3$): δ 7.71 (s, 1H), 7.39 (d, 1H), 7.26 (d, 1H), 7.10 (t, 1H), 7.04 (t, 1H), 6.95 (dd, 1H), 6.65 (s, 1H), 6.26 (s, 1H), 6.04 (s, 1H), 5.78 (s, 1H), 5.09 (d, 1H), 4.99 (dd, 1H), 4.63 (s, 1H), 4.60 (dd, 1H), 4.33 (s, 1H), 4.29 (d, 1H), 4.22 (s, 1H), 4.21 (d, 1H), 3.78 (s, 3H), 3.42 (m, 2H), 3.21-2.79 (m, 4H), 2.63 (m, 3H), 2.37 (s, 3H), 2.27 (m, 1H), 2.22 (s, 3H), 2.13 (s, 3H).

ESI-MS m/z: Calcd. for C$_{42}$H$_{41}$N$_5$O$_9$S: 791.3 Found (M+H$^+$): 792.1

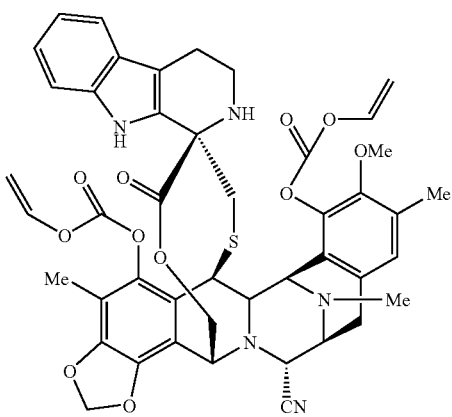

Compound 60: $^1$H-NMR (300 MHz, CDCl$_3$): δ 7.70 (s, 1H), 7.40 (d, 1H), 7.26 (d, 1H), 7.18 Me (dd, 1H), 7.11 (t, 1H), 7.05 (s, 1H), 7.02 (t, 1H), 6.97 (dd, 1H), 6.27 (s, 1H), 6.05 (s, 1H), 5.10 (d, 1H), 5.09-5.00 (m, 1H), 5.05 (s, 1H), 4.72 (dd, 1H), 4.60 (dd, 1H), 4.56 (s, 1H), 4.33 (s, 1H), 4.22 (m, 2H), 3.97 (d, 1H), 3.78 (s, 3H), 3.46 (m, 2H), 3.18 (m, 1H), 3.11 (d, 1H), 2.97 (dd, 1H), 2.85 (m, 1H), 2.71-2.51 (m, 3H), 2.37 (s, 3H), 2.32 (m, 1H), 2.21 (s, 3H), 2.16 (s, 3H).

ESI-MS m/z: Calcd. for C$_{45}$H$_{43}$N$_5$O$_{11}$S: 861.3 Found (M+H$^+$): 862.7.

Method 6: To a solution of 1 equiv. of ET-694-CN, compound 50 in CH$_2$Cl$_2$ (0.032M) under argon at room temperature were added 2 equiv. of acid, 2 equiv. of EDC.HCl and 2 equiv. of DMAP. The reaction was followed by TLC and quenched with an aqueous saturated solution of NaHCO$_3$, extracted with CH$_2$Cl$_2$ and the organic layers dried over Na$_2$SO$_4$. Flash chromatography gives pure compounds.

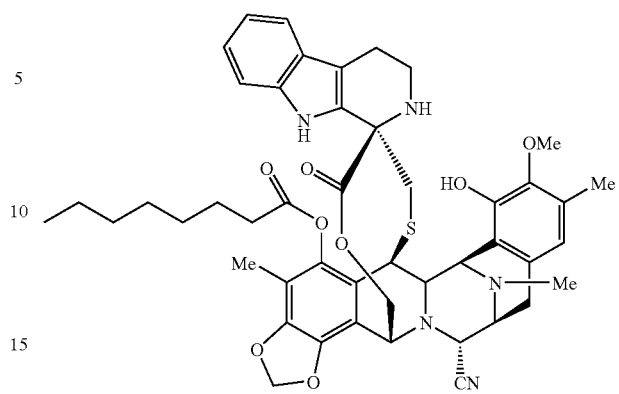

Compound 61: $^1$H-NMR (300 MHz, CDCl$_3$): δ 7.70 (s, 1H), 7.39 (d, 1H), 7.26 (d, 1H), 7.11 (t, 1H), 7.00 (t, 1H), 6.65 (s, 1H), 6.23 (s, 1H), 6.03 (s, 1H), 5.72 (s, 1H), 5.09 (d, 1H), 4.57 (broad s, 1H), 4.33 (s, 1H), 4.26 (d, 1H), 4.21 (s, 1H), 4.19 (d, 1H), 3.80 (s, 3H), 3.44 (m, 2H), 3.16 (m, 1H), 3.03 (d, 1H), 3.00-2.89 (m, 2H), 2.68-2.52 (m, 3H), 2.54 (t, 2H), 2.37 (s, 3H), 2.31 (m, 1H), 2.21 (s, 3H), 2.04 (s, 3H), 1.65 (m, 2H), 1.29 (m, 8H), 0.87 (m, 3H).

ESI-MS m/z: Calcd. for C$_{47}$H$_{53}$N$_5$O$_8$S: 847.4 Found (M+H$^+$): 848.3.

Method 4.—To a solution of 1 equiv. of starting material in CH$_3$CN/H$_2$O 3:2 (0.009M) were added 30 equiv. of AgNO$_3$. After 24 h the reaction was quenched with a mixture 1:1 of saturated solutions of brine and NaHCO$_3$, stirred for 10 min and diluted and extracted with CH$_2$Cl$_2$. The organic layer was dried with Na$_2$SO$_4$. Chromatography gives pure compounds.

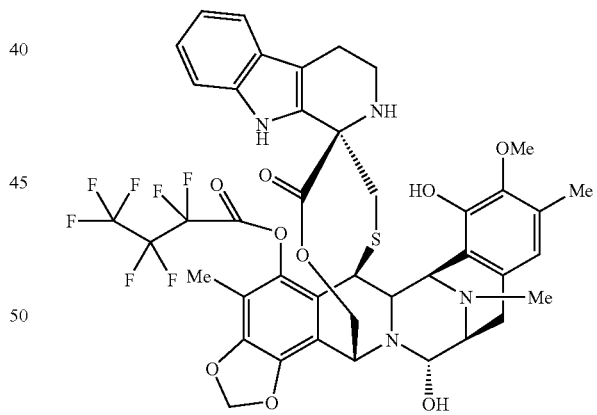

Compound 62: $^1$H-NMR (300 MHz, CDCl$_3$): δ 7.65 (s, 1H); 7.40 (d, 1H); 7.25 (d, 1H); 7.10 (ddd, 1H); 7.01 (ddd, 1H); 6.66 (s, 1H); 6.27 (d, 1H); 6.04 (d, 1H); 5.69 (s, 1H); 5.23 (d, 1H); 4.85 (s, 1H); 4.51 (d, 1H); 4.47 (s, 1H); 4.19 (s, 1H); 4.15 (dd, 1H); 3.78 (s, 3H); 3.52-3.50 (m, 1H); 3.26-3.14 (m, 2H); 3.04-2.80 (m, 3H); 2.72-2.47 (m, 3H); 2.36 (s, 3H); 2.20 (s, 3H); 2.05 (s, 3H).

ESI-MS m/z: Calcd. for C$_{42}$H$_{39}$F$_7$N$_4$O$_9$S: 908.3 Found (M+H$^+$): 909.2.

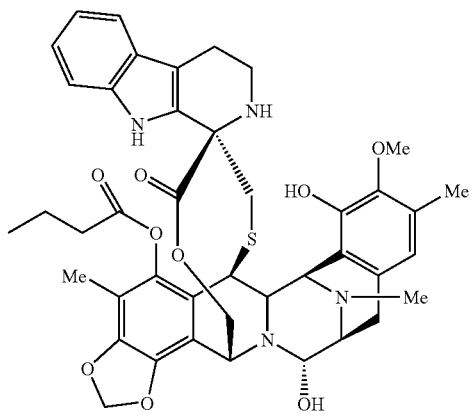

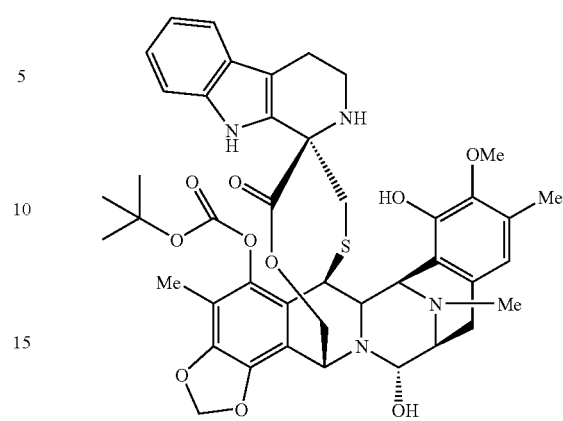

Compound 63: $^1$H-NMR (300 MHz, CDCl$_3$): δ 7.71 (d, 1H), 7.38 (d, 1H), 7.26 (d, 1H), 7.09 (t, 1H), 7.03 (t, 1H), 6.67 (s, 1H), 6.21 (d, 1H), 5.99 (d, 1H), 5.71 (broad s, 1H), 5.18 (d, 1H), 4.83 (s, 1H), 4.50 (d, 1H), 4.46 (broad s, 1H), 4.17 (d, 1H), 4.12 (d, 1H), 3.81 (s, 3H), 3.51 (d, 1H), 3.24-3.18 (m, 2H), 3.00 (d, 1H), 2.85 (m, 2H), 2.70-2.50 (m, 5H), 2.37 (s, 3H), 2.27 (m, 1H), 2.19 (s, 3H), 2.04 (s, 3H), 1.74 (sext, 2H), 1.01 (t, 3H).

ESI-MS m/z: Calcd. for C$_{42}$H$_{46}$N$_4$O$_9$S: 782.3 Found (M+H$^+$): 783.2.

Compound 65: $^1$H-NMR (300 MHz, CDCl$_3$): δ 7.74 (s, 1H), 7.40 (d, 1H), 7.27 (d, 1H), 7.11 (t, 1H), 7.02 (t, 1H), 6.65 (s, 1H), 6.23 (s, 1H), 6.02 (s, 1H), 5.74 (broad s, 1H), 5.20 (d, 1H), 4.82 (s, 1H), 4.58 (s, 1H), 4.49 (m, 1H), 4.13 (m, 2H), 3.81 (s, 3H), 3.49 (m, 1H), 3.21 (m, 2H), 3.02 (d, 1H), 2.80 (m, 3H), 2.64 (m, 2H), 2.37 (s, 3H), 2.29 (m, 1H), 2.21 (s, 3H), 2.11 (s, 3H), 1.45 (s, 9H).

ESI-MS m/z: Calcd. for C$_{43}$H$_{48}$N$_4$O$_{10}$S: 812.3 Found (M+H$^+$): 813.0.

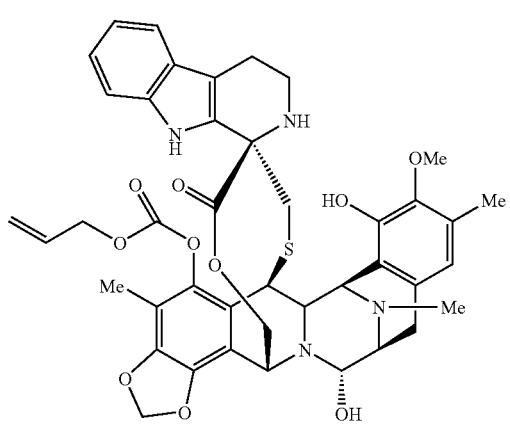

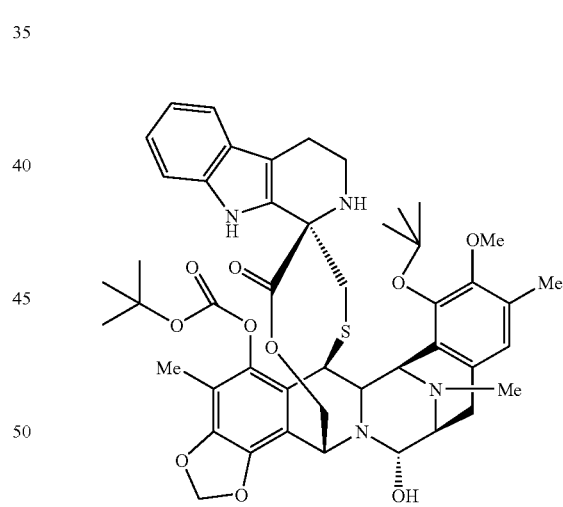

Compound 64: $^1$H-NMR (300 MHz, CDCl$_3$): δ 7.71 (s, 1H), 7.39 (d, 1H), 7.25 (d, 1H), 7.10 (t, 1H), 7.01 (t, 1H), 6.66 (s, 1H), 6.22 (s, 1H), 6.00 (s, 1H), 5.90 (ddd, 1H), 5.74 (broad s, 1H), 5.37 (d, 1H), 5.22 (t, 1H), 4.83 (s, 1H), 4.59 (m, 2H), 4.49 (s, 1H), 4.29 (dd, 1H), 4.15 (m, 2H), 3.80 (s, 3H), 3.65 (m, 1H), 3.51 (m, 2H), 3.18 (m, 1H), 3.09-2.81 (m, 3H), 2.59 (m, 3H), 2.37 (s, 3H), 2.26 (m, 1H), 2.21 (s, 3H), 2.12 (s, 3H).

ESI-MS m/z: Calcd. for C$_{42}$H$_{44}$N$_4$O$_{10}$S: 796.3 Found (M+H$^+$): 797.0

Compound 66: $^1$H-NMR (300 MHz, CDCl$_3$): δ 7.71 (s, 1H), 7.39 (d, 1H), 7.26 (d, 1H); 7.11 (t, 1H), 7.02 (t, 1H), 6.99 (s, 1H), 6.21 (s, 1H), 6.00 (s, 1H), 5.19 (d, 1H), 4.80 (s, 1H), 4.51 (m, 2H), 4.16 (m, 2H), 3.83 (s, 3H), 3.54 (m, 1H), 3.28-3.04 (m, 3H), 2.92-2.78 (m, 2H), 2.59 (m, 3H), 2.36 (s, 3H), 2.31 (m, 1H), 2.18 (s, 3H), 2.11 (s, 3H), 1.54 (s, 9H), 1.45 (s, 9H).

ESI-MS m/z: Calcd. for C$_{48}$H$_{56}$N$_4$O$_{12}$S: 912.4 Found (M+H$^+$): 913.1.

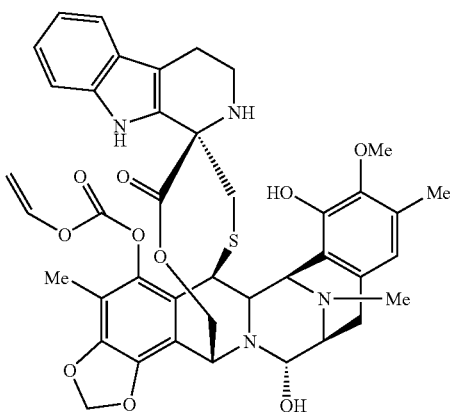

Compound 67: ¹H-NMR (300 MHz, CDCl₃): δ 7.70 (s, 1H), 7.39 (d, 1H), 7.26 (d, 1H), 7.10 (t, 1H), 7.01 (t, 1H), 6.95 (dd, 1H), 6.66 (s, 1H), 6.24 (s, 1H), 6.01 (s, 1H), 5.75 (s, 1H), 5.21 (d, 1H), 4.99 (dd, 1H), 4.84 (s, 1H), 4.58 (dd, 1H), 4.55 (s, 1H), 4.51 (s, 1H), 4.20 (s, 1H), 4.15 (d, 1H), 3.78 (s, 3H), 3.49 (m, 1H), 3.21 (m, 2H), 3.00 (d, 1H), 2.86 (m, 2H), 2.59 (m, 3H), 2.37 (s, 3H), 2.27 (m, 1H), 2.20 (s, 3H), 2.12 (s, 3H).

ESI-MS m/z: Calcd. for $C_{41}H_{42}N_4O_{10}S$: 782.3 Found (M+H⁺): 783.1

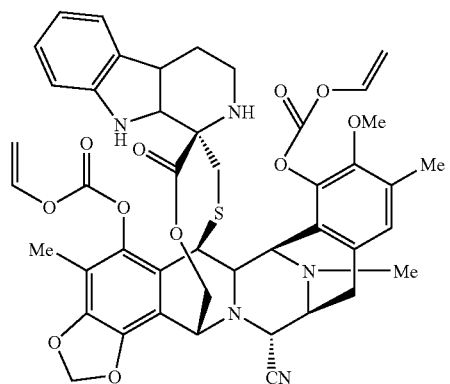

Compound 68: ¹H-NMR (300 MHz, CDCl₃): 7.67 (s, 1H), 7.39 (d, 1H), 7.24 (d, 1H), 7.17 (dd, 1H), 7.10 (t, 1H), 7.05 (s, 1H), 7.02 (t, 1H), 6.97 (dd, 1H), 6.24 (s, 1H), 6.02 (s, 1H), 5.21 (d, 1H), 5.06 (dd, 1H), 5.01 (dd, 1H), 4.83 (s, 1H); 4.72 (dd, 1H), 4.60 (dd, 1H), 4.51 (s, 1H), 4.48 (s, 1H), 4.15 (dd, 1H), 3.86 (d, 1H), 3.78 (s, 3H), 3.54 (d, 1H), 3.28-3.18 (m, 2H), 3.07 (d, 1H), 2.94-2.84 (m, 2H), 2.67-2.52 (m, 3H), 2.37 (s, 3H), 2.32 (m, 1H), 2.18 (s, 3H), 2.14 (s, 3H).

ESI-MS m/z: Calcd. for $C_{44}H_{44}N_4O_{12}S$: 852.3 Found (M+H⁺): 853.5

Bioassays for Antitumor Screening

The finality of these assays is to interrupt the growth of a "in vitro" tumor cell culture by means of a continued exhibition of the cells to the sample to be testing.

Cell Lines

| Name | N° ATCC | Species | Tissue | Characteristics |
|---|---|---|---|---|
| P-388 | CCL-46 | mouse | ascites fluid | lymphoid neoplasm |
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| SW620 | CCL-228 | human | colon | colon adenocarcinoma (lymph node metastasis) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| MCF-7 | HTB-22 | human | breast | breast adenocarcinoma, (pleural effusion) |
| MDA-MB-231 | HTB-26 | human | breast | breast adenocarcinoma, Her2/neu+, (pleural effusion) |
| IGROV-1 | | human | ovary | ovary adenocarcinoma |
| IGROV-ET | | human | ovary | ovary adenocarcinoma, characterized as ET-743 resistant cells |
| SK-OV-3 | HTB-77 | human | ovary | ovary adenocarcinoma (malignant ascites) |
| OVCAR-3 | HTB-161 | human | ovary | ovary adenocarcinoma |
| HeLa | CCL-2 | human | cervix | cervix epitheloid carcinoma |
| HeLa-APL | CCL-3 | human | cervix | cervix epitheloid carcinoma, characterized as aplidine resistant cells |
| A-498 | HTB-44 | human | kidney | kidney carcinoma |
| PANC-1 | CRL-1469 | human | pancreas | pancreatic epitheloid carcinoma |
| HMEC1 | | human | endothelium | |

Inhibition of Cells Growth by Colorimetric Assay

A colorimetric type of assay, using sulphorhodamine B (SRB) reaction has been adapted for a quantitative measurement of cell growth and viability [following the technique described by Philip Skehan, et al. (1990), New colorimetric cytotoxicity assay for anticancer drug screening, *J. Natl. Cancer Inst.*, 82:1107-1112]

This form of the assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulphate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at 5×10³ cells per well in aliquots of 195 μl medium, and they are allowed to attach to the plate surface by growing in drug free medium for 18 hours. Afterward, samples are added in aliquots of 5 μl in a ranging from 10 to $10^{-8}$ μg/ml, dissolved in DMSO/EtOH/PBS (0.5:0.5:99). After 48 hours exposure, the antitumor effect are measured by the SRB methodology: cells are fixed by adding 50 μl of cold 50% (wt/vol) trichloroacetic acid (TCA) and incubating for 60 minutes at 4° C. Plates are washed with deionized water and dried. One hundred μl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean+/− SD of data from triplicate wells are calculated. Some parameters for cellular responses can be calculated: GI=growth inhibition, TGI=total growth inhibition (cytostatic effect) and LC=cell killing (cytotoxic effect).

Obtained results may predict the usefulness of a certain drug as a potential cancer treatment. For this technique, compounds which show $GI_{50}$ values smaller than 10 μg/ml are selected to continue with further studies. $GI_{50}$ data allow to predict that not only could a drug be cystostatic, but also it could have a potential in terms of tumor reduction.

Activity Data (Molar).

|  |  | Compound 1 |
| --- | --- | --- |
| A549 | $IC_{50}$ | 1.31E−09 |
| HT29 |  | 1.31E−09 |

|  |  | Compound 2 | Compound 3 | Compound 4 | Compound 5 | Compound 6 | Compound 7 |
| --- | --- | --- | --- | --- | --- | --- | --- |
| A549 | $GI_{50}$ | 6.30E−10 | 3.45E−07 | 2.30E−06 | 1.29E−08 | 5.13E−09 | 7.67E−07 |
|  | TGI | 6.30E−09 | 3.45E−06 | 6.90E−06 | 1.29E−07 | 5.13E−08 | 1.28E−07 |
|  | $LC_{50}$ | 6.30E−05 | 5.75E−05 | 1.15E−05 | 1.29E−05 | 1.28E−05 | 1.28E−06 |
| HT29 | $GI_{50}$ | 1.26E−09 | 2.30E−07 | 2.30E−06 | 1.29E−08 | 5.13E−09 | 6.39E−08 |
|  | TGI | 1.26E−09 | 2.30E−07 | 2.30E−06 | 1.29E−08 | 5.13E−09 | 6.39E−08 |
|  | $LC_{50}$ | 6.30E−05 | 5.75E−05 | 1.15E−05 | 5.14E−06 | 5.13E−06 | 1.28E−06 |
| H-MEC-1 | $GI_{50}$ |  |  |  |  |  |  |
|  | TGI |  |  |  |  |  |  |
|  | $LC_{50}$ |  |  |  |  |  |  |

|  |  | Compound 8 | Compound 9 | Compound 10 | Compound 11 | Compound 12 | Compound 13 |
| --- | --- | --- | --- | --- | --- | --- | --- |
| A549 | $GI_{50}$ | 2.52E−09 | 2.52E−08 | 3.91E−08 | 1.89E−08 | 7.28E−09 | 6.31E−09 |
|  | TGI | 1.01E−08 | 1.01E−07 | 1.28E−07 | 5.00E−08 | 8.35E−08 | 6.79E−08 |
|  | $LC_{50}$ | 1.26E−05 | 8.82E−06 | 1.28E−05 | 1.29E−07 | 1.26E−05 | 1.26E−05 |
| HT29 | $GI_{50}$ | 2.52E−09 | 3.78E−07 | 4.03E−08 | 3.09E−08 | 1.37E−08 | 3.33E−07 |
|  | TGI | 2.52E−09 | 3.78E−07 | 1.28E−05 | 1.29E−07 | 1.26E−07 | 1.26E−06 |
|  | $LC_{50}$ | 5.04E−06 | 1.26E−05 | 1.28E−05 | 1.29E−05 | 1.26E−05 | 1.26E−05 |
| H-MEC-1 | $GI_{50}$ |  |  |  |  |  |  |
|  | TGI |  |  |  |  |  |  |
|  | $LC_{50}$ |  |  |  |  |  |  |

|  |  | Compound 15 | Compound 16 | Compound 17 | Compound 18 | Compound 19 | Compound 20 |
| --- | --- | --- | --- | --- | --- | --- | --- |
| A549 | $GI_{50}$ | 4.78E−09 | 3.67E−08 | 5.39E−09 | 6.77E−09 | 3.27E−09 | 3.30E−07 |
|  | TGI | 1.31E−08 | 1.28E−07 | 4.41E−08 | 1.29E−07 | 1.29E−08 | 1.20E−06 |
|  | $LC_{50}$ | 1.27E−06 | 4.44E−06 | 6.67E−06 | 1.29E−05 | 1.29E−05 | 6.77E−06 |
| HT29 | $GI_{50}$ | 4.16E−09 | 4.28E−08 | 2.22E−08 | 5.62E−09 | 4.45E−09 | 5.96E−07 |
|  | TGI | 1.31E−08 | 1.28E−07 | 1.28E−08 | 1.29E−07 | 1.29E−07 | 1.20E−05 |
|  | $LC_{50}$ | 1.31E−05 | 1.28E−05 | 1.28E−05 | 1.29E−05 | 1.29E−05 | 1.20E−05 |
| H-MEC-1 | $GI_{50}$ |  |  |  |  |  |  |
|  | TGI |  |  |  |  |  |  |
|  | $LC_{50}$ |  |  |  |  |  |  |

|  |  | Compound 21 | Compound 22 | Compound 23 | Compound 24 | Compound 25 | Compound 50 |
| --- | --- | --- | --- | --- | --- | --- | --- |
| A549 | $GI_{50}$ | 7.58E−07 | 3.93E−08 | 1.18E−07 | 1.24E−05 | 1.18E−05 | 4.16E−07 |
|  | TGI | 6.99E−06 | 1.20E−07 | 1.26E−06 | 1.24E−05 | 1.18E−05 | 6.93E−07 |
|  | $LC_{50}$ | 1.16E−05 | 1.20E−05 | 1.11E−05 | 1.24E−05 | 1.18E−05 | 1.39E−06 |

-continued

|  |  | Compound 21 | Compound 22 | Compound 23 | Compound 24 | Compound 25 | Compound 50 |
|---|---|---|---|---|---|---|---|
| HT29 | $GI_{50}$ | 1.18E−06 | 1.20E−07 | 2.47E−07 | 1.24E−05 | 1.18E−05 | 6.93E−07 |
|  | TGI | 1.16E−05 | 5.70E−06 | 1.11E−05 | 1.24E−05 | 1.18E−05 | 6.93E−07 |
|  | $LC_{50}$ | 1.16E−05 | 1.20E−05 | 1.11E−05 | 1.24E−05 | 1.18E−05 | 6.93E−06 |
| H-MEC-1 | $GI_{50}$ |  |  |  |  |  |  |
|  | TGI |  |  |  |  |  |  |
|  | $LC_{50}$ |  |  |  |  |  |  |

|  |  | Compound 52 | Compound 53 | Compound 54 | Compound 55 | Compound 56 | Compound 58 |
|---|---|---|---|---|---|---|---|
| A549 | $GI_{50}$ | 4.70E−08 | 2.61E−07 | 1.10E−07 | 4.95E−08 | 9.30E−09 | 8.91E−08 |
|  | TGI | 1.26E−07 | 7.84E−07 | 3.53E−07 | 3.11E−07 | 2.36E−07 | 1.34E−06 |
|  | $LC_{50}$ | 9.43E−04 | 1.22E−05 | 1.10E−06 | 1.10E−05 | 3.79E−06 | 1.08E−05 |
| HT29 | $GI_{50}$ | 7.93E−08 | 3.09E−07 | 1.30E−07 | 8.20E−08 | 4.74E−08 | 2.30E−07 |
|  | TGI | 1.26E−05 | 1.23E−06 | 5.41E−07 | 1.24E−06 | 1.22E−05 | 1.08E−05 |
|  | $LC_{50}$ | 1.26E−05 | 1.23E−06 | 3.37E−06 | 1.24E−05 | 1.22E−05 | 1.08E−05 |
| H-MEC-1 | $GI_{50}$ | 3.47E−07 | 1.32E−07 |  | 5.48E−10 | 4.17E−09 | 1.02E−08 |
|  | TGI | 6.95E−09 | 1.23E−05 |  | 1.13E−09 | 9.65E−09 | 1.08E−05 |
|  | $LC_{50}$ | 1.26E−08 | 1.23E−05 |  | 6.68E−09 | 3.78E−07 | 1.08E−05 |

|  |  | Compound 59 | Compound 61 | Compound 63 | Compound 64 | Compound 65 | Compound 66 |
|---|---|---|---|---|---|---|---|
| A549 | $GI_{50}$ | 2.66E−09 | 1.18E−05 | 3.12E−09 | 1.64E−09 | 2.05E−09 | 2.09E−08 |
|  | TGI | 2.26E−06 | 1.18E−05 | 9.53E−09 | 6.83E−09 | 6.30E−09 | 5.75E−08 |
|  | $LC_{50}$ | 4.98E−06 | 1.18E−05 | 3.03E−06 | 1.10E−06 | 4.79E−08 | 3.76E−07 |
| HT29 | $GI_{50}$ | 3.80E−09 | 1.18E−05 | 3.88E−09 | 1.91E−09 | 8.56E−10 | 2.80E−08 |
|  | TGI | 1.84E−08 | 1.18E−05 | 1.28E−08 | 1.25E−08 | 2.05E−08 | 1.13E−07 |
|  | $LC_{50}$ | 1.26E−05 | 1.18E−05 | 1.28E−05 | 1.25E−05 | 1.23E−05 | 1.10E−05 |
| H-MEC-1 | $GI_{50}$ | 4.00E−09 | 3.94E−07 | 2.72E−09 | 3.10E−10 | 6.13E−10 | 2.07E−08 |
|  | TGI | 1.26E−08 | 8.05E−07 | 1.28E−08 | 1.25E−08 | 4.35E−08 | 8.04E−08 |
|  | $LC_{50}$ | 1.26E−05 | 3.40E−06 | 1.28E−05 | 1.25E−05 | 1.23E−05 | 1.10E−05 |

|  |  | Compound 67 |
|---|---|---|
| A549 | $GI_{50}$ | 4.55E−10 |
|  | TGI | 2.86E−09 |
|  | $LC_{50}$ | 1.28E−07 |
| HT29 | $GI_{50}$ | 1.90E−09 |
|  | TGI | 1.28E−07 |
|  | $LC_{50}$ | 1.28E−05 |
| H-MEC-1 | $GI_{50}$ | 5.21E−10 |
|  | TGI | 1.28E−07 |
|  | $LC_{50}$ | 1.28E−05 |

|  |  | Compound 14 | Compound 26 | Compound 27 | Compound 28 | Compound 29 | Compound 30 |
|---|---|---|---|---|---|---|---|
| A549 | $GI_{50}$ | 2.64E−07 | 2.65E−09 | 2.55E−10 | 3.48E−09 | 2.32E−08 | 3.90E−11 |
|  | TGI | 8.25E−07 | 3.97E−09 | 8.92E−10 | 4.65E−08 | 3.48E−08 | 2.60E−10 |
|  | $LC_{50}$ | 6.86E−06 | 1.32E−08 | 6.37E−09 | 3.48E−08 | 9.29E−08 | 1.04E−09 |
| HT29 | $GI_{50}$ | 4.18E−07 | 3.97E−09 | 2.55E−10 | 1.16E−08 | 2.32E−08 | 1.04E−10 |
|  | TGI | 1.59E−06 | 7.95E−09 | 7.64E−10 | 6.97E−08 | 6.97E−08 | 3.90E−10 |
|  | $LC_{50}$ | 1.29E−05 | 1.32E−08 | 1.15E−09 | 1.05E−07 | 1.05E−07 | 1.04E−09 |
| SW-620 | $GI_{50}$ |  | 2.65E−09 | 2.55E−10 | 6.97E−09 | 2.32E−08 | 2.60E−11 |
|  | TGI |  | 7.95E−09 | 6.37E−10 | 2.32E−08 | 6.97E−08 | 3.90E−10 |
|  | $LC_{50}$ |  | 7.95E−09 | 1.15E−09 | 9.29E−08 | 1.05E−07 | 1.30E−09 |
| MEL-28 | $GI_{50}$ | 1.98E−07 | 2.65E−09 | 2.55E−10 | 2.32E−08 | 2.32E−08 | 2.60E−11 |
|  | TGI | 5.19E−07 | 5.30E−09 | 6.37E−10 | 3.48E−08 | 3.48E−08 | 1.30E−10 |
|  | $LC_{50}$ | 2.37E−06 | 1.06E−08 | 1.27E−09 | 8.13E−08 | 8.13E−08 | 6.50E−10 |
| OVCAR | $GI_{50}$ |  |  |  |  |  |  |
|  | TGI |  |  |  |  |  |  |
|  | $LC_{50}$ |  |  |  |  |  |  |

-continued

|  |  | Compound 14 | Compound 26 | Compound 27 | Compound 28 | Compound 29 | Compound 30 |
|---|---|---|---|---|---|---|---|
| A498 | $GI_{50}$ |  | 2.65E−09 | 2.55E−10 | 3.48E−09 | 3.48E−09 | 1.30E−10 |
|  | TGI |  | 6.62E−09 | 5.10E−10 | 1.16E−08 | 1.16E−08 | 5.20E−10 |
|  | $LC_{50}$ |  | 2.65E−08 | 1.27E−09 | 5.81E−08 | 1.16E−07 | 2.60E−09 |
| DU145 | $GI_{50}$ | 9.46E−08 | 2.65E−09 | 2.55E−11 | 2.32E−09 | 2.32E−08 | 1.30E−11 |
|  | TGI | 1.39E−06 | 3.97E−09 | 8.92E−11 | 3.48E−09 | 3.48E−08 | 3.90E−11 |
|  | $LC_{50}$ | 1.29E−05 | 1.06E−08 | 3.82E−09 | 9.29E−08 | 9.29E−08 | 1.30E−10 |
| MCF | $GI_{50}$ |  | 2.65E−09 | 2.55E−10 | 5.81E−09 | 2.32E−08 | 2.60E−10 |
|  | TGI |  | 5.30E−09 | 1.27E−09 | 2.32E−08 | 3.48E−08 | 3.90E−10 |
|  | $LC_{50}$ |  | 1.19E−08 | 1.15E−08 | 1.16E−07 | 1.16E−07 | 2.60E−09 |
| MB231 | $GI_{50}$ |  | 2.65E−09 | 2.55E−10 | 3.48E−09 | 2.32E−08 | 2.60E−12 |
|  | TGI |  | 5.30E−09 | 6.37E−09 | 9.29E−09 | 4.65E−08 | 1.30E−10 |
|  | $LC_{50}$ |  | 1.32E−08 | 1.27E−08 | 1.16E−07 | 1.16E−07 | 3.90E−09 |
| H-MEC-1 | $GI_{50}$ |  |  |  |  |  |  |
|  | TGI |  |  |  |  |  |  |
|  | $LC_{50}$ |  |  |  |  |  |  |
| LNCAP | $GI_{50}$ | 6.12E−08 |  |  |  |  |  |
|  | TGI | 1.77E−07 |  |  |  |  |  |
|  | $LC_{50}$ | 5.35E−07 |  |  |  |  |  |
| SK-OV3 | $GI_{50}$ |  |  |  |  |  |  |
|  | TGI |  |  |  |  |  |  |
|  | $LC_{50}$ |  |  |  |  |  |  |
| IGROV | $GI_{50}$ | 2.26E−07 |  |  |  |  |  |
|  | TGI | 7.44E−07 |  |  |  |  |  |
|  | $LC_{50}$ | 5.14E−06 |  |  |  |  |  |
| IGROV-ET | $GI_{50}$ | 5.69E−07 |  |  |  |  |  |
|  | TGI | 1.30E−06 |  |  |  |  |  |
|  | $LC_{50}$ | 1.29E−05 |  |  |  |  |  |
| SK-BR3 | $GI_{50}$ | 2.17E−07 |  |  |  |  |  |
|  | TGI | 5.37E−07 |  |  |  |  |  |
|  | $LC_{50}$ | 1.62E−06 |  |  |  |  |  |
| K562 | $GI_{50}$ | 4.47E−08 |  |  |  |  |  |
|  | TGI | 1.74E−07 |  |  |  |  |  |
|  | $LC_{50}$ | 1.29E−06 |  |  |  |  |  |
| PANC-1 | $GI_{50}$ | 2.76E−07 |  |  |  |  |  |
|  | TGI | 8.25E−07 |  |  |  |  |  |
|  | $LC_{50}$ | 1.29E−05 |  |  |  |  |  |
| LOVO | $GI_{50}$ | 1.41E−07 |  |  |  |  |  |
|  | TGI | 3.93E−07 |  |  |  |  |  |
|  | $LC_{50}$ | 1.10E−06 |  |  |  |  |  |
| LOVO-DOX | $GI_{50}$ | 5.84E−07 |  |  |  |  |  |
|  | TGI | 3.84E−06 |  |  |  |  |  |
|  | $LC_{50}$ | 1.29E−05 |  |  |  |  |  |
| HELA | $GI_{50}$ | 1.14E−07 |  |  |  |  |  |
|  | TGI | 3.10E−07 |  |  |  |  |  |
|  | $LC_{50}$ | 8.10E−07 |  |  |  |  |  |
| HELA-APL | $GI_{50}$ | 2.43E−07 |  |  |  |  |  |
|  | TGI | 4.88E−07 |  |  |  |  |  |
|  | $LC_{50}$ | 9.80E−07 |  |  |  |  |  |

|  |  | Compound 31 | Compound 32 | Compound 33 | Compound 34 | Compound 35 | Compound 36 |
|---|---|---|---|---|---|---|---|
| A549 | $GI_{50}$ | 2.59E−09 | 3.88E−09 | 3.82E−10 | 5.10E−09 | 3.03E−09 | 2.84E−08 |
|  | TGI | 5.19E−09 | 2.59E−08 | 1.27E−09 | 2.55E−08 | 7.65E−09 | 5.07E−08 |
|  | $LC_{50}$ | 3.89E−08 | 9.06E−08 | 5.10E−09 | 8.92E−08 | 4.09E−06 | 9.09E−08 |
| HT29 | $GI_{50}$ | 3.89E−09 | 7.76E−09 | 2.55E−10 | 7.64E−09 | 4.19E−09 | 6.18E−08 |
|  | TGI | 7.78E−09 | 2.59E−08 | 7.64E−10 | 2.54E−09 | 1.32E−08 | 1.87E−07 |
|  | $LC_{50}$ | 1.30E−08 | 1.03E−07 | 1.15E−09 | 1.15E−08 | 1.29E−05 | 1.30E−05 |
| SW-620 | $GI_{50}$ | 2.59E−09 | 5.17E−09 | 2.55E−10 | 1.02E−08 |  |  |
|  | TGI | 3.89E−09 | 2.59E−08 | 1.15E−09 | 3.82E−08 |  |  |
|  | $LC_{50}$ | 1.17E−08 | 1.29E−07 | 1.02E−08 | 1.02E−07 |  |  |
| MEL-28 | $GI_{50}$ | 2.59E−09 | 2.59E−09 | 2.55E−10 | 3.82E−09 | 2.78E−09 | 2.16E−09 |
|  | TGI | 3.89E−09 | 1.03E−08 | 6.37E−10 | 1.27E−08 | 7.16E−09 | 5.23E−09 |
|  | $LC_{50}$ | 1.04E−08 | 2.59E−08 | 1.15E−09 | 6.37E−08 | 4.70E−08 | 1.26E−08 |
| OVCAR | $GI_{50}$ |  |  |  |  |  |  |
|  | TGI |  |  |  |  |  |  |
|  | $LC_{50}$ |  |  |  |  |  |  |
| A498 | $GI_{50}$ | 2.59E−09 | 2.59E−09 | 2.55E−10 | 3.82E−09 |  |  |
|  | TGI | 6.49E−09 | 9.06E−09 | 5.10E−10 | 1.27E−08 |  |  |
|  | $LC_{50}$ | 1.30E−08 | 5.17E−08 | 1.27E−09 | 6.37E−08 |  |  |
| DU145 | $GI_{50}$ | 1.30E−09 | 1.29E−09 | 3.82E−10 | 2.55E−09 | 3.83E−09 | 5.41E−09 |
|  | TGI | 3.89E−09 | 2.59E−09 | 8.92E−10 | 3.82E−09 | 1.20E−08 | 9.39E−09 |
|  | $LC_{50}$ | 9.08E−09 | 3.88E−09 | 3.82E−09 | 1.02E−08 | 1.29E−05 | 1.30E−05 |

-continued

|  |  | Compound 31 | Compound 32 | Compound 33 | Compound 34 | Compound 35 | Compound 36 |
|---|---|---|---|---|---|---|---|
| MCF | $GI_{50}$ | 2.59E−09 | 9.06E−09 | 1.02E−09 | 5.10E−09 |  |  |
|  | TGI | 5.19E−09 | 2.59E−08 | 2.55E−09 | 2.55E−08 |  |  |
|  | $LC_{50}$ | 1.17E−08 | 1.29E−07 | 1.15E−08 | 1.27E−07 |  |  |
| MB231 | $GI_{50}$ | 1.30E−09 | 2.59E−09 | 2.55E−10 | 3.82E−09 |  |  |
|  | TGI | 5.19E−09 | 9.06E−09 | 1.27E−09 | 1.02E−08 |  |  |
|  | $LC_{50}$ | 1.30E−08 | 9.06E−08 | 1.27E−08 | 1.27E−07 |  |  |
| H-MEC-1 | $GI_{50}$ |  |  |  |  | 2.60E−09 | 8.43E−08 |
|  | TGI |  |  |  |  | 3.04E−08 | 7.83E−07 |
|  | $LC_{50}$ |  |  |  |  | 1.29E−05 | 1.30E−05 |
| LNCAP | $GI_{50}$ |  |  |  |  | 8.16E−10 | 6.14E−09 |
|  | TGI |  |  |  |  | 2.50E−09 | 9.48E−09 |
|  | $LC_{50}$ |  |  |  |  | 7.48E−09 | 2.51E−08 |
| SK-OV3 | $GI_{50}$ |  |  |  |  | 4.37E−09 | 5.07E−08 |
|  | TGI |  |  |  |  | 1.46E−08 | 2.05E−07 |
|  | $LC_{50}$ |  |  |  |  | 1.29E−05 | 1.30E−05 |
| IGROV | $GI_{50}$ |  |  |  |  | 3.45E−09 | 3.72E−09 |
|  | TGI |  |  |  |  | 7.72E−09 | 7.21E−09 |
|  | $LC_{50}$ |  |  |  |  | 3.38E−06 | 2.71E−08 |
| IGROV-ET | $GI_{50}$ |  |  |  |  | 5.53E−09 | 5.03E−08 |
|  | TGI |  |  |  |  | 2.35E−08 | 1.03E−07 |
|  | $LC_{50}$ |  |  |  |  | 1.29E−05 | 1.30E−07 |
| SK-BR3 | $GI_{50}$ |  |  |  |  | 2.21E−09 | 1.18E−08 |
|  | TGI |  |  |  |  | 6.55E−09 | 3.20E−08 |
|  | $LC_{50}$ |  |  |  |  | 1.09E−06 | 8.64E−08 |
| K562 | $GI_{50}$ |  |  |  |  | 1.14E−09 | 6.15E−09 |
|  | TGI |  |  |  |  | 2.67E−09 | 9.92E−09 |
|  | $LC_{50}$ |  |  |  |  | 1.02E−08 | 1.09E−07 |
| PANC-1 | $GI_{50}$ |  |  |  |  | 4.52E−09 | 4.21E−08 |
|  | TGI |  |  |  |  | 4.21E−08 | 1.04E−07 |
|  | $LC_{50}$ |  |  |  |  | 1.29E−05 | 1.30E−05 |
| LOVO | $GI_{50}$ |  |  |  |  | 2.26E−09 | 2.73E−08 |
|  | TGI |  |  |  |  | 5.68E−09 | 5.46E−08 |
|  | $LC_{50}$ |  |  |  |  | 1.29E−08 | 1.09E−07 |
| LOVO-DOX | $GI_{50}$ |  |  |  |  | 2.68E−08 | 7.04E−08 |
|  | TGI |  |  |  |  | 1.24E−07 | 9.77E−07 |
|  | $LC_{50}$ |  |  |  |  | 1.29E−05 | 1.30E−05 |
| HELA | $GI_{50}$ |  |  |  |  |  |  |
|  | TGI |  |  |  |  |  |  |
|  | $LC_{50}$ |  |  |  |  |  |  |
| HELA-APL | $GI_{50}$ |  |  |  |  |  |  |
|  | TGI |  |  |  |  |  |  |
|  | $LC_{50}$ |  |  |  |  |  |  |

|  |  | Compound 37 | Compound 38 | Compound 39 | Compound 40 | Compound 41 | Compound 42 |
|---|---|---|---|---|---|---|---|
| A549 | $GI_{50}$ | 4.23E−09 | 2.38E−09 | 4.67E−08 | 2.41E−09 | 1.98E−08 | 2.20E−08 |
|  | TGI | 2.17E−08 | 5.24E−09 | 8.74E−08 | 4.11E−08 | 4.68E−08 | 4.09E−08 |
|  | $LC_{50}$ | 1.38E−07 | 1.15E−08 | 2.32E−06 | 7.02E−09 | 1.10E−07 | 7.59E−08 |
| HT29 | $GI_{50}$ | 3.71E−09 | 4.20E−09 | 4.85E−08 | 3.26E−09 | 5.66E−09 | 3.41E−08 |
|  | TGI | 1.40E−08 | 1.69E−08 | 1.73E−05 | 1.06E−08 | 6.07E−08 | 1.42E−07 |
|  | $LC_{50}$ | 1.27E−05 | 1.27E−05 | 1.30E−05 | 1.30E−05 | 1.27E−05 | 1.27E−05 |
| SW-620 | $GI_{50}$ |  |  |  |  |  |  |
|  | TGI |  |  |  |  |  |  |
|  | $LC_{50}$ |  |  |  |  |  |  |
| MEL-28 | $GI_{50}$ | 2.40E−09 | 2.73E−09 | 3.47E−08 | 1.96E−08 | 6.72E−09 | 4.04E−10 |
|  | TGI | 6.82E−09 | 5.33E−09 | 6.91E−08 | 4.70E−08 | 2.66E−08 | 9.77E−10 |
|  | $LC_{50}$ | 3.35E−08 | 1.04E−08 | 1.81E−07 | 1.12E−07 | 1.02E−07 | 6.19E−09 |
| OVCAR | $GI_{50}$ |  |  |  |  |  |  |
|  | TGI |  |  |  |  |  |  |
|  | $LC_{50}$ |  |  |  |  |  |  |
| A498 | $GI_{50}$ |  |  |  |  |  |  |
|  | TGI |  |  |  |  |  |  |
|  | $LC_{50}$ |  |  |  |  |  |  |
| DU145 | $GI_{50}$ | 4.60E−09 | 2.04E−09 | 5.59E−08 | 2.35E−09 | 3.49E−09 | 3.51E−09 |
|  | TGI | 1.06E−08 | 6.80E−09 | 2.03E−06 | 6.41E−09 | 8.37E−09 | 7.97E−09 |
|  | $LC_{50}$ | 1.27E−05 | 1.27E−05 | 1.30E−05 | 2.45E−06 | 9.90E−06 | 1.27E−08 |
| MCF | $GI_{50}$ |  |  |  |  |  |  |
|  | TGI |  |  |  |  |  |  |
|  | $LC_{50}$ |  |  |  |  |  |  |
| MB231 | $GI_{50}$ |  |  |  |  |  |  |
|  | TGI |  |  |  |  |  |  |
|  | $LC_{50}$ |  |  |  |  |  |  |

-continued

|  |  | Compound 37 | Compound 38 | Compound 39 | Compound 40 | Compound 41 | Compound 42 |
|---|---|---|---|---|---|---|---|
| H-MEC-1 | $GI_{50}$ | 2.22E−09 | 3.06E−09 | 5.81E−08 | 2.45E−09 | 4.68E−09 | 4.04E−08 |
|  | TGI | 3.58E−08 | 8.93E−09 | 1.46E−06 | 5.31E−09 | 4.08E−08 | 2.47E−07 |
|  | $LC_{50}$ | 1.27E−05 | 1.27E−05 | 1.30E−05 | 1.15E−08 | 1.27E−05 | 1.27E−05 |
| LNCAP | $GI_{50}$ | 2.60E−10 | 2.00E−10 | 2.05E−08 | 1.02E−09 | 2.62E−09 | 3.74E−09 |
|  | TGI | 8.56E−10 | 7.21E−10 | 4.41E−08 | 2.48E−09 | 5.17E−09 | 6.61E−09 |
|  | $LC_{50}$ | 4.75E−09 | 3.07E−09 | 9.47E−08 | 5.88E−09 | 1.02E−08 | 1.17E−08 |
| SK-OV3 | $GI_{50}$ | 3.57E−09 | 2.55E−09 | 6.24E−08 | 2.90E−09 | 3.85E−09 | 7.37E−09 |
|  | TGI | 1.07E−08 | 7.13E−09 | 3.19E−07 | 6.28E−09 | 9.82E−09 | 7.92E−07 |
|  | $LC_{50}$ | 1.27E−05 | 1.27E−05 | 1.30E−05 | 1.30E−08 | 1.27E−05 | 1.27E−05 |
| IGROV | $GI_{50}$ | 2.82E−09 | 7.57E−10 | 4.30E−08 | 1.96E−09 | 1.94E−09 | 2.44E−09 |
|  | TGI | 7.06E−09 | 2.89E−09 | 8.15E−08 | 4.17E−09 | 4.14E−09 | 5.12E−09 |
|  | $LC_{50}$ | 6.13E−07 | 8.40E−09 | 2.32E−06 | 8.86E−09 | 8.86E−09 | 1.07E−08 |
| IGROV-ET | $GI_{50}$ | 3.76E−08 | 1.57E−08 | 8.25E−08 | 2.42E−09 | 3.14E−09 | 4.32E−08 |
|  | TGI | 1.19E−07 | 6.59E−08 | 4.04E−06 | 8.66E−09 | 2.00E−08 | 9.42E−08 |
|  | $LC_{50}$ | 1.27E−05 | 6.51E−06 | 1.30E−05 | 4.80E−06 | 3.86E−06 | 1.27E−05 |
| SK-BR3 | $GI_{50}$ | 2.96E−09 | 1.07E−09 | 4.99E−08 | 2.56E−09 | 2.33E−09 | 6.63E−09 |
|  | TGI | 6.80E−09 | 3.38E−09 | 1.10E−07 | 6.50E−09 | 6.86E−09 | 2.44E−08 |
|  | $LC_{50}$ | 1.41E−07 | 9.54E−09 | 9.44E−07 | 2.80E−08 | 3.63E−08 | 8.73E−08 |
| K562 | $GI_{50}$ | 4.92E−10 | 4.22E−10 | 2.51E−08 | 8.43E−10 | 1.10E−10 | 4.77E−09 |
|  | TGI | 1.36E−09 | 8.18E−10 | 4.46E−08 | 6.87E−09 | 2.19E−09 | 9.15E−09 |
|  | $LC_{50}$ | 1.27E−08 | 3.15E−09 | 7.92E−08 | 8.00E−08 | 5.57E−09 | 2.81E−06 |
| PANC-1 | $GI_{50}$ | 3.12E−09 | 3.22E−09 | 6.01E−08 | 2.82E−09 | 1.08E−08 | 1.69E−08 |
|  | TGI | 1.18E−08 | 8.37E−09 | 9.22E−07 | 7.17E−09 | 4.89E−08 | 8.25E−08 |
|  | $LC_{50}$ | 3.02E−06 | 4.28E−07 | 1.30E−05 | 1.28E−07 | 5.06E−07 | 1.27E−05 |
| LOVO | $GI_{50}$ | 2.92E−09 | 3.55E−09 | 3.21E−08 | 2.51E−09 | 4.42E−09 | 1.35E−08 |
|  | TGI | 8.97E−09 | 1.03E−08 | 6.22E−08 | 5.98E−09 | 2.44E−08 | 4.37E−08 |
|  | $LC_{50}$ | 1.27E−05 | 1.27E−05 | 1.20E−05 | 2.38E−08 | 4.10E−07 | 1.27E−05 |
| LOVO-DOX | $GI_{50}$ | 6.17E−08 | 5.53E−08 | 2.34E−07 | 3.04E−08 | 3.05E−08 | 4.59E−08 |
|  | TGI | 4.10E−07 | 8.42E−07 | 9.94E−07 | 9.12E−08 | 9.99E−08 | 2.05E−07 |
|  | $LC_{50}$ | 1.27E−05 | 1.27E−05 | 1.30E−05 | 5.51E−07 | 1.27E−05 | 1.27E−05 |
| HELA | $GI_{50}$ |  |  |  |  |  |  |
|  | TGI |  |  |  |  |  |  |
|  | $LC_{50}$ |  |  |  |  |  |  |
| HELA-APL | $GI_{50}$ |  |  |  |  |  |  |
|  | TGI |  |  |  |  |  |  |
|  | $LC_{50}$ |  |  |  |  |  |  |

|  |  | Compound 43 | Compound 44 | Compound 45 | Compound 46 | Compound 47 | Compound 48 |
|---|---|---|---|---|---|---|---|
| A549 | $GI_{50}$ | 5.12E−09 | 2.74E−08 | 6.89E−08 | 3.33E−08 | 3.33E−08 | 5.56E−07 |
|  | TGI | 1.08E−08 | 4.76E−08 | 3.01E−07 | 6.78E−08 | 7.50E−08 | 1.09E−06 |
|  | $LC_{50}$ | 3.28E−08 | 8.23E−08 | 4.47E−06 | 3.35E−07 | 1.33E−06 | 1.26E−05 |
| HT29 | $GI_{50}$ | 4.64E−08 | 5.98E−08 | 8.78E−08 | 4.44E−08 | 3.88E−08 | 5.01E−07 |
|  | TGI | 1.04E−07 | 4.59E−07 | 1.21E−06 | 1.22E−06 | 1.21E−05 | 1.26E−06 |
|  | $LC_{50}$ | 1.30E−05 | 1.30E−05 | 1.21E−05 | 1.17E−05 | 1.21E−05 | 1.26E−05 |
| SW-620 | $GI_{50}$ |  |  |  |  |  |  |
|  | TGI |  |  |  |  |  |  |
|  | $LC_{50}$ |  |  |  |  |  |  |
| MEL-28 | $GI_{50}$ | 3.08E−07 | 2.63E−09 | 3.07E−08 | 1.24E−08 | 4.26E−09 | 3.59E−07 |
|  | TGI | 5.81E−07 | 5.22E−09 | 7.03E−08 | 4.07E−08 | 1.00E−08 | 7.12E−07 |
|  | $LC_{50}$ | 1.09E−06 | 1.03E−08 | 3.78E−07 | 1.53E−07 | 2.07E−07 | 3.09E−06 |
| OVCAR | $GI_{50}$ |  |  |  |  |  |  |
|  | TGI |  |  |  |  |  |  |
|  | $LC_{50}$ |  |  |  |  |  |  |
| A498 | $GI_{50}$ |  |  |  |  |  |  |
|  | TGI |  |  |  |  |  |  |
|  | $LC_{50}$ |  |  |  |  |  |  |
| DU145 | $GI_{50}$ | 4.76E−09 | 6.54E−09 | 3.92E−08 | 6.48E−09 | 5.46E−09 | 6.97E−07 |
|  | TGI | 9.04E−09 | 1.18E−08 | 9.54E−08 | 4.61E−08 | 2.06E−08 | 1.08E−05 |
|  | $LC_{50}$ | 1.30E−08 | 1.30E−05 | 1.21E−05 | 1.17E−05 | 1.21E−05 | 1.26E−05 |
| MCF | $GI_{50}$ |  |  |  |  |  |  |
|  | TGI |  |  |  |  |  |  |
|  | $LC_{50}$ |  |  |  |  |  |  |
| MB231 | $GI_{50}$ |  |  |  |  |  |  |
|  | TGI |  |  |  |  |  |  |
|  | $LC_{50}$ |  |  |  |  |  |  |
| H-MEC-1 | $GI_{50}$ | 1.18E−08 | 7.53E−08 | 4.79E−08 | 2.60E−08 | 6.78E−09 | 5.70E−07 |
|  | TGI | 1.77E−07 | 1.31E−06 | 8.41E−06 | 1.17E−06 | 1.50E−07 | 1.26E−05 |
|  | $LC_{50}$ | 1.30E−05 | 1.30E−05 | 1.21E−05 | 1.17E−05 | 1.21E−05 | 1.26E−05 |
| LNCAP | $GI_{50}$ | 2.02E−09 | 4.30E−09 | 3.83E−09 | 1.17E−10 | 2.65E−09 | 2.16E−07 |
|  | TGI | 3.76E−09 | 8.84E−09 | 1.21E−08 | 3.25E−09 | 5.08E−09 | 4.28E−07 |
|  | $LC_{50}$ | 7.00E−09 | 3.11E−08 | 4.82E−08 | 1.75E−08 | 9.76E−09 | 8.45E−07 |

-continued

|  |  | Compound 43 | Compound 44 | Compound 45 | Compound 46 | Compound 47 | Compound 48 |
| --- | --- | --- | --- | --- | --- | --- | --- |
| SK-OV3 | $GI_{50}$ | 3.39E−09 | 3.75E−08 | 4.06E−08 | 3.06E−08 | 8.98E−09 | 5.50E−07 |
|  | TGI | 7.17E−09 | 1.31E−07 | 1.24E−07 | 2.00E−06 | 2.88E−07 | 1.12E−06 |
|  | $LC_{50}$ | 1.30E−08 | 1.30E−05 | 1.21E−05 | 1.17E−05 | 1.21E−05 | 1.26E−05 |
| IGROV | $GI_{50}$ | 2.73E−09 | 4.29E−09 | 4.35E−08 | 2.32E−08 | 1.06E−08 | 4.21E−07 |
|  | TGI | 5.20E−09 | 1.22E−08 | 9.49E−08 | 5.40E−08 | 4.07E−08 | 8.32E−07 |
|  | $LC_{50}$ | 9.88E−09 | 9.30E−08 | 2.24E−06 | 1.92E−07 | 9.09E−07 | 5.62E−06 |
| IGROV-ET | $GI_{50}$ | 9.10E−09 | 2.85E−08 | 2.33E−07 | 4.95E−08 | 6.97E−08 | 8.76E−07 |
|  | TGI | 2.35E−08 | 7.06E−08 | 2.56E−06 | 1.29E−07 | 3.61E−06 | 1.26E−05 |
|  | $LC_{50}$ | 1.30E−05 | 1.30E−07 | 1.21E−05 | 7.35E−06 | 1.21E−05 | 1.26E−05 |
| SK-BR3 | $GI_{50}$ | 3.77E−09 | 1.27E−08 | 6.68E−08 | 1.63E−08 | 7.56E−09 | 6.11E−07 |
|  | TGI | 8.65E−09 | 4.27E−08 | 2.50E−07 | 5.84E−08 | 3.47E−08 | 1.69E−06 |
|  | $LC_{50}$ | 4.11E−08 | 1.77E−07 | 1.21E−06 | 4.12E−07 | 6.93E−07 | 1.15E−05 |
| K562 | $GI_{50}$ | 2.51E−09 | 3.94E−09 | 2.13E−08 | 1.22E−06 | 1.31E−08 | 5.01E−07 |
|  | TGI | 4.88E−09 | 9.38E−09 | 5.45E−08 | 2.02E−06 | 2.11E−06 | 1.76E−06 |
|  | $LC_{50}$ | 9.49E−09 | 1.07E−07 | 2.10E−07 | 3.38E−06 | 6.32E−06 | 3.55E−06 |
| PANC-1 | $GI_{50}$ | 5.28E−09 | 5.67E−08 | 2.86E−08 | 4.11E−08 | 4.24E−08 | 7.06E−07 |
|  | TGI | 1.15E−08 | 1.55E−07 | 1.15E−06 | 2.58E−07 | 1.70E−06 | 1.21E−05 |
|  | $LC_{50}$ | 3.90E−08 | 1.30E−05 | 1.21E−05 | 1.17E−05 | 1.21E−05 | 1.26E−05 |
| LOVO | $GI_{50}$ | 3.50E−09 | 2.71E−08 | 4.29E−08 | 1.56E−08 | 6.26E−09 | 3.22E−07 |
|  | TGI | 8.32E−09 | 5.10E−08 | 1.17E−07 | 5.70E−08 | 4.64E−08 | 6.28E−07 |
|  | $LC_{50}$ | 3.89E−08 | 9.61E−08 | 1.21E−05 | 1.17E−05 | 1.21E−05 | 1.22E−06 |
| LOVO-DOX | $GI_{50}$ | 3.98E−08 | 9.10E−08 | 3.49E−07 | 3.82E−08 | 4.07E−08 | 1.35E−06 |
|  | TGI | 1.06E−07 | 8.53E−07 | 1.03E−06 | 2.41E−07 | 1.17E−07 | 6.21E−06 |
|  | $LC_{50}$ | 1.30E−05 | 1.30E−05 | 1.21E−05 | 1.17E−05 | 1.21E−05 | 1.26E−05 |
| HELA | $GI_{50}$ |  |  |  |  |  |  |
|  | TGI |  |  |  |  |  |  |
|  | $LC_{50}$ |  |  |  |  |  |  |
| HELA-APL | $GI_{50}$ |  |  |  |  |  |  |
|  | TGI |  |  |  |  |  |  |
|  | $LC_{50}$ |  |  |  |  |  |  |

|  |  | Compound 49 | Compound 51 | Compound 57 | Compound 62 | Compound 68 |
| --- | --- | --- | --- | --- | --- | --- |
| A549 | $GI_{50}$ | 2.64E−06 | 2.67E−08 | 1.03E−07 | 8.80E−09 | 2.83E−08 |
|  | TGI | 4.97E−06 | 6.11E−08 | 6.07E−07 | 3.30E−08 | 4.95E−08 |
|  | $LC_{50}$ | 9.37E−06 | 1.29E−06 | 1.22E−05 | 7.70E−08 | 1.01E−07 |
| HT29 | $GI_{50}$ | 4.50E−06 | 3.82E−08 | 1.65E−07 | 1.10E−08 | 3.17E−07 |
|  | TGI | 1.26E−05 | 1.31E−06 | 1.41E−06 | 6.60E−08 | 9.59E−08 |
|  | $LC_{50}$ | 1.26E−05 | 1.11E−05 | 1.22E−05 | 9.90E−08 | 1.17E−05 |
| SW-620 | $GI_{50}$ |  |  |  | 2.20E−08 |  |
|  | TGI |  |  |  | 5.50E−08 |  |
|  | $LC_{50}$ |  |  |  | 1.10E−07 |  |
| MEL-28 | $GI_{50}$ |  | 2.84E−08 | 6.47E−08 | 3.30E−09 | 7.52E−09 |
|  | TGI |  | 5.03E−08 | 2.09E−07 | 1.10E−09 | 2.24E−08 |
|  | $LC_{50}$ |  | 8.93E−08 | 6.62E−07 | 3.30E−08 | 6.72E−08 |
| OVCAR | $GI_{50}$ |  |  |  |  |  |
|  | TGI |  |  |  |  |  |
|  | $LC_{50}$ |  |  |  |  |  |
| A498 | $GI_{50}$ |  |  |  | 3.30E−09 |  |
|  | TGI |  |  |  | 4.40E−09 |  |
|  | $LC_{50}$ |  |  |  | 1.10E−08 |  |
| DU145 | $GI_{50}$ |  | 4.83E−08 | 4.77E−08 | 2.20E−09 | 2.99E−08 |
|  | TGI |  | 3.23E−07 | 1.84E−06 | 4.40E−09 | 8.65E−08 |
|  | $LC_{50}$ |  | 1.12E−05 | 1.22E−05 | 9.90E−09 | 1.03E−05 |
| MCF | $GI_{50}$ |  |  |  | 2.20E−09 |  |
|  | TGI |  |  |  | 9.90E−09 |  |
|  | $LC_{50}$ |  |  |  | 1.10E−07 |  |
| MB231 | $GI_{50}$ |  |  |  | 1.10E−09 |  |
|  | TGI |  |  |  | 5.50E−09 |  |
|  | $LC_{50}$ |  |  |  | 3.30E−08 |  |
| H-MEC-1 | $GI_{50}$ | 1.99E−06 |  |  |  |  |
|  | TGI | 4.12E−06 |  |  |  |  |
|  | $LC_{50}$ | 8.54E−06 |  |  |  |  |
| LNCAP | $GI_{50}$ |  | 1.31E−08 | 3.33E−08 |  | 1.15E−08 |
|  | TGI |  | 2.70E−08 | 7.17E−08 |  | 2.66E−08 |
|  | $LC_{50}$ |  | 5.48E−08 | 2.32E−08 |  | 6.13E−08 |
| SK-OV3 | $GI_{50}$ |  |  |  |  |  |
|  | TGI |  |  |  |  |  |
|  | $LC_{50}$ |  |  |  |  |  |
| IGROV | $GI_{50}$ |  | 3.23E−08 | 7.18E−08 |  | 2.17E−08 |
|  | TGI |  | 6.33E−08 | 4.60E−07 |  | 6.16E−08 |
|  | $LC_{50}$ |  | 3.55E−06 | 7.43E−06 |  | 1.09E−06 |

-continued

|  |  | Compound 49 | Compound 51 | Compound 57 | Compound 62 | Compound 68 |
|---|---|---|---|---|---|---|
| IGROV-ET | $GI_{50}$ |  | 2.63E−07 | 3.94E−07 |  | 3.08E−08 |
|  | TGI |  | 7.47E−06 | 1.15E−06 |  | 6.89E−08 |
|  | $LC_{50}$ |  | 1.12E−05 | 1.22E−05 |  | 2.06E−07 |
| SK-BR3 | $GI_{50}$ |  | 3.98E−08 | 6.76E−08 |  | 2.90E−08 |
|  | TGI |  | 9.93E−08 | 3.13E−07 |  | 6.09E−08 |
|  | $LC_{50}$ |  | 3.11E−06 | 7.99E−06 |  | 2.06E−07 |
| K562 | $GI_{50}$ |  | 1.65E−08 | 4.77E−08 |  | 2.04E−08 |
|  | TGI |  | 4.62E−08 | 4.66E−07 |  | 4.47E−08 |
|  | $LC_{50}$ |  | 1.14E−07 | 1.22E−05 |  | 9.75E−08 |
| PANC-1 | $GI_{50}$ |  | 4.19E−08 | 1.13E−07 |  | 4.81E−08 |
|  | TGI |  | 1.33E−07 | 6.62E−07 |  | 1.25E−07 |
|  | $LC_{50}$ |  | 2.00E−06 | 1.22E−05 |  | 1.17E−05 |
| LOVO | $GI_{50}$ |  | 2.11E−08 | 7.30E−08 |  | 2.71E−08 |
|  | TGI |  | 3.88E−08 | 2.57E−07 |  | 4.97E−08 |
|  | $LC_{50}$ |  | 7.10E−08 | 9.05E−07 |  | 9.13E−08 |
| LOVO-DOX | $GI_{50}$ |  | 3.81E−07 | 4.87E−07 |  | 1.12E−07 |
|  | TGI |  | 3.09E−06 | 6.70E−06 |  | 7.43E−07 |
|  | $LC_{50}$ |  | 1.12E−05 | 1.22E−05 |  | 1.17E−05 |
| HELA | $GI_{50}$ |  | 2.40E−08 | 4.37E−08 |  | 3.25E−08 |
|  | TGI |  | 4.85E−08 | 1.46E−07 |  | 6.03E−08 |
|  | $LC_{50}$ |  | 9.80E−08 | 6.52E−07 |  | 1.12E−07 |
| HELA-APL | $GI_{50}$ |  | 2.91E−08 | 6.14E−08 |  | 3.70E−08 |
|  | TGI |  | 4.97E−08 | 2.03E−07 |  | 6.19E−08 |
|  | $LC_{50}$ |  | 8.46E−08 | 8.50E−07 |  | 1.03E−07 |

Toxicity Data

Toxicity was asssessed by the methods reported in Toxicology in Vitro, 15 (2001) 571-577, J. Luber Narod et al.: "Evaluation of the use of in vitro methodologies as tools for screening new compounds for potential in vivo toxicity".

Methods

In order to assess the cytotoxicity of the drugs to normal cells, we used 96 well plates plated at a density of 5000 cells per well (except for the FDC-P1 which were plated at 12,000 cells per well) with normal cell lines (ATCC, Table 1) maintained as per the directions of the ATCC: AML-12, normal mouse liver cells; NRK-52E, normal rat kidney cells; L8, normal rat skeletal muscle cells; FDC-P1, normal mouse myelogeous stem cells; and H9c2 (2-1), normal rat cardiac muscle cells. The cells in each plate were permitted to settle overnight before adding the test drug. In addition, primary neuronal cultures were prepared from embryonic (day e-17) whole brain (forebrain and brainstem) and spinal cord using established methods (Federoff and Richardson, 1997).

To each well (100 μl medium) 10 μl of drug in media was added at varying concentrations (1×10-10-0.01 mg/ml final concentration) and further incubated overnight at 37° C. with 5% CO2. After 24 h the following assays were performed. All experiments were repeated at least 3 times and were assayed in duplicate.

1. MTS assay (CellTiter 96 aqueous) was performed according to the manufacturer's (Promega) directions (for all cell types). Cell viability (mitochondrial activity) is determined via enzymatic conversion of the formazan substrate.

| Compound n° | Liver | Heart | Myelo | Skeletal | Kidney |
|---|---|---|---|---|---|
| 26 | 1.06E−06 | 6.43E−07 | 1.03E−07 | 3.71E−08 | 4.60E−08 |
| 27 | 1.48E−08 | 9.93E−08 | 1.75E−08 | 1.54E−08 | 1.01E−08 |
| 28 | 1.42E−07 | 1.84E−07 | 2.00E−07 | 1.45E−07 | 8.37E−08 |
| 29 | 1.59E−08 | 7.22E−08 | 1.79E−08 | 3.29E−07 | 1.94E−08 |
| 30 | 2.72E−07 | 5.06E−07 | 7.58E−09 | 2.51E−08 | 4.19E−09 |
| 31 | 1.89E−08 | 6.65E−08 | 3.18E−08 | 1.35E−08 | 4.27E−08 |
| 32 | 6.00E−07 | 2.42E−07 | 5.25E−07 | 1.51E−08 | 1.45E−07 |
| 33 | 1.05E−08 | 1.27E−06 | 1.92E−08 | 1.41E−08 | 7.78E−09 |
| 34 | 2.55E−06 | 4.96E−07 | 1.15E−05 | 1.48E−08 | 2.74E−07 |
| 35 | 4.88E−08 | 1.93E−08 | 4.08E−08 | 3.07E−08 | 3.42E−08 |
| 36 | 3.19E−07 | 8.86E−07 | 2.05E−07 | 2.71E−08 | 3.56E−07 |
| 37 | 5.46E−09 | 1.74E−08 | 4.59E−09 | 2.22E−08 | 2.92E−08 |
| 38 | 1.39E−10 | 2.96E−09 | 9.66E−11 | 1.29E−08 | 9.85E−08 |
| 39 | 1.14E−06 | NT | 4.10E−07 | 4.58E−07 | 9.88E−05 |
| 40 | 3.86E−08 | NT | 4.08E−08 | 2.11E−07 | 2.95E−07 |
| 41 | 6.30E−08 | 3.49E−08 | 1.39E−07 | 2.39E−07 | 1.89E−08 |
| 42 | 1.86E−07 | 1.42E−07 | 6.41E−08 | 3.37E−08 | 1.12E−09 |
| 43 | 7.57E−08 | 9.42E−08 | 6.23E−08 | 1.60E−07 | 4.38E−08 |
| 44 | 4.33E−07 | 5.20E−06 | 1.21E−07 | 4.02E−08 | 4.15E−07 |
| 46 | 5.01E−08 | 3.51E−08 | 1.17E−07 | 2.16E−07 | 4.01E−08 |
| 47 | 3.04E−08 | 7.36E−08 | 6.76E−08 | 2.57E−08 | 3.15E−08 |

In Vitro Evaluation of the Compounds for ADME-TOX Profile

Partition Coefficient (log D)

The partition coefficient of a chemical compound provides a thermodynamic measure of its hydrophilicity-lipophylicity balance. Lipophilicity is a major structural factor that influences the pharmacokinetic and pharmacodynamic behavior of compounds. The partition coefficient between water or buffer and 1-octanol is the most widely used measure of chemical compound lipophilicity.

The measurement of partition coefficient was evaluated based on a miniaturized shake-flask procedure. Buffer (Dulbecco's PBS, pH 7.40) was used as the aqueous phase. The tested compound was dissolved in DMSO, at the concentration of 100 µM. The final DMSO concentration (1%.) during the octanol-buffer partitioning are very low to avoid bias on the partitioning. The amount of compound in the buffer phase was determined by HPLC with photodiode array detection after an equilibration phase of 60 min. The amount of compound in the octanol phase is calculated by subtraction of the amount of compound in buffer from the total amount of compound, which is determined from a calibration sample.

Log D is calculated as the $Log_{10}$ of the amount of compound in the octanol phase divided by the amount of compound in the buffer phase. The effective range of the log D microassay is approximately −0.5 to +4.5.

In Vitro Intestinal Absorption Assays

The intestinal epithelium permeability is a critical characteristic that determines the rate and extent of human absorption and ultimately the bioavailability of a drug candidate. Caco-2 permeability assay allows a rapid assessment of membrane permeability and thus helps to rank-order compounds in terms of their absorption potential.

The Caco-2 cell line is a human colon adenocarcinoma cell line that differentiates in culture and resembles the epithelial lining of the human small intestine. It has been widely used as an in vitro intestinal epithelial model for drug transport and permeability screening of discovery compounds.

The apparent permeability coefficients ($P_{app}$) was determined in the apical-to-basolateral (A-to-B) direction across the cell monolayers (TC-7 sub-clone of the Caco-2) cultured on polycarbonate membrane filters. Compounds were tested at 50 µM with at a final DMSO concentration of 1%. Samples were analyzed by HPLC-MS or HPLC-MS/MS.

The test compound was added to the apical side and the $P_{app}$ was determined based on the rate of appearance of the test compound in the basolateral side after 2 h-incubation. Two reference compounds, propranolol (highly permeable) and ranitidine (poorly permeable), are tested in each assay as controls. Results from this assay can be used to rank-order compounds in terms of their absorption potential. Compounds with $P_{app}$ equals to or greater than 20×10-6 cm/s could be considered highly permeable and are likely to be "not permeability-limited". Compounds with $P_{app}$ less than 5×10-6 cm/s are considered poorly permeable and are likely to be "permeability-limited". Compounds with $P_{app}$ greater than 5×10-6 but less than 20×10-6 cm/s" are considered to have medium permeability.

Metabolism

Hepatic metabolism is a primary determinant of pharmacokinetic behavior, and rapid first-pass metabolism is a major cause of low bioavailability. Pooled liver microsomes and recombinant cytochrome P450's are used for the metabolic assessment of hits, leads, and new pharmaceutical compounds. The results of the metabolic screening studies are useful in:

Determining the initial rate at which compounds are metabolized

Investigating the major pathways of drug metabolism

Predicting in vivo pharmacokinetic behavior

Investigating the potential for drug-drug interactions

The metabolic stability was determined used human liver S9 homogenate that including both microsomal and cytosolic enzyme activities. The test compound was diluted in methanol (0.625%) and acetonitrile (0.625%) at the concentration 1 µM and incubated in the human liver pool (protein=1 mg/mL) during 60 min at 37° C. Peak areas corresponding to all analytes (metabolic products) were determined by HPLC-MS/MS. Areas were recorded and ratios of peak areas of analytes to that of internal standard for each analyte were determined. The ratio of precursor compound remaining after 60 minutes and the amount remaining at time zero, expressed as percent, are reported as metabolic stability. Higher values mean higher metabolic stability.

Inhibition of Cytochromes P450 (CYP450)

The cytochromes P450 are a group of related enzymes primarily located in the liver and responsible of the metabolism of drugs. The inhibition of these CYP by drugs are related with drug-drug interactions and toxicities.

CYP3A4 is the most common form of the CYP3A enzymes found in adults and is the form implicated in most drug interactions. CYP2D6 metabolize more than 25% of the clinically useful medications.

For CYP2D6 inhibition assay, the compound are tested at 10 µM in duplicate with a 0.25% final concentration of both methanol and acetonitrile in presence of the fluorescent substrate AMMC (3-[2-N,N-diethyl-N-methylammonium) ethyl]-7-methoxy-4-methylcoumarin) at the concentration of 1.5 µM). The conversion of the AMMC in AHMC (3-[2-N, N-diethyl-N-methylammonium)ethyl]-7-hydroxy-4-methyl-coumarin) is determined spectrofluorimetry after incubation with the enzyme during 450 min at 37° C.

For CYP3A4 inhibition assay, the compound were tested at 10 µM in duplicate with a 0.25% final concentration of both methanol and acetonitrile in presence of the fluorescent substrate BFC (50 µM). The conversion of the BFC (7-benzyloxy-4-trifluoromethylcoumarin) in HFC (7-hydroxy-4-trifluoromethylcoumarin) was determined spectro-fluormetry after incubation with the enzyme during 30 min at 37° C.

For both assays, the fluorescent intensity measured at t=0 is subtracted from that measured after the appropriate incubation time. The ratio of signal-to-noise is calculated by comparing the fluorescence in incubations containing the test compound to the control samples containing the same solvent vehicle. The percent of control activity is calculated and reported as percent inhibition.

In vitro Safety Assessment. Cell Viability

The toxic potential of compounds was investigated in vitro using primary human hepatocytes (HEPG2). The compounds were tested at 30 µM in duplicate with a final DMSO concentration of 1%. After incubation during 24 h at 37° C. the cell viability was determined by the conversion of oxided alarmarBlue (resazurin) to reduced alarmarBlue (resorufin). Chlorpromazine was used as reference compound. Results are expressed as a percent of inhibition of control values.

Results of the Studies ADME-TOX

| Compound | Relative Peak Area of Principal Peak (Chromatographic Purity) (%) | Solubility Dulbecco's PBS pH 7.4 (μM) | log D n-Octanol-Dulbecco's PBS pH 7.4 | Permeability A to B TC 7 Cells $P_{app}$ ($10^{-6}$ cm/s) |
|---|---|---|---|---|
| 31 | 97.4 | 18.28 | 3.61 | <0.32 |
| 35 | 99.0 | <1 est | >5.0 | PD |
| 26 (ET-736) | 62.9 | <1 est | >5.0 | PD |
| 27 | 84.9 | 2.99 | >5.0 | <1.18 |
| 34 | 98.6 | 17.65 | >5.0 | 5.00 |
| 33 | 82.6 | 68.94 | 3.50 | 7.77 |
| 28 | 88.8 | <1 est | >4.6 | ND |
| 29 | 97.5 | 1.59 | >4.9 | ND |
| 30 | 100.0 | 2.24 | >4.9 | ND |
| 32 | 92.8 | 14.28 | >4.3 | PD |
| 36 | 98.4 | 26.03 | >4.4 | PD |
| 43 | 96.0 | 5.85 | >4.5 | ND |
| 44 | 97.4 | 20.69 | >4.9 | PD |
| 41 | 92.9 | <1 est | >4.5 | ND |
| 42 | 96.8 | 10.37 | >4.8 | PD |
| 46 | 95.9 | 1.37 | >5.0 | PD |
| 47 | 87.4 | <1 est | >5.0 | PD |

| Compound | Human Liver S9 Metabolic Stability (% remaining) | CYP2D6 (% inhibition) | CYP3A4 (% inhibition) | Cell Viability (% inhibition) |
|---|---|---|---|---|
| 31 | 17 | — | 84 | 22 |
| 35 | 4 | — | 24 | 23 |
| 26 (ET-736) | 3 | 12 | 45 | — |
| 27 | 7 | 13 | 53 | — |
| 34 | 24 | 28 | 80 | 45 |
| 33 | 10 | 28 | 84 | 32 |
| 28 | 33 | 34 | 79 | 17 |
| 29 | 9 | 27 | 55 | 29 |
| 30 | 6 | — | 25 | — |
| 32 | 9 | 12 | 83 | 39 |
| 36 | 2 | 15 | 78 | 33 |
| 43 | 3 | — | 15 | — |
| 44 | 4 | 16 | 72 | 73 |
| 41 | 7 | 16 | 22 | 16 |
| 42 | 5 | 19 | 78 | 67 |
| 46 | 7 | 16 | 60 | 33 |
| 47 | 5 | 10 | 38 | 18 |

The invention claimed is:
1. A compound of the general formula I:

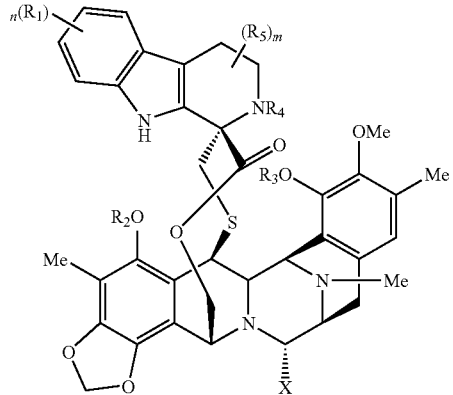

wherein $R_1$ is OH, OR', SH, SR', SOR', $SO_2R'$, $NO_2$, $NH_2$, NHR', $N(R')_2$, NHC(=O)R', CN, halogen, substituted or unsubstituted $C_1$-$C_{25}$ alkyl, substituted or unsubstituted $C_2$-$C_{18}$ alkenyl, substituted or unsubstituted $C_2$-$C_{18}$ alkynyl, substituted or unsubstituted carbocyclic aryl selected from phenyl, naphthyl, biphenyl, phenanthryl and anthracyl, substituted or unsubstituted heterocyclic selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrrolidinyl;

$R_2$, $R_3$, $R_4$, and $R_5$ are each independently selected from H, OH, OR', SH, SR', SOR', $SO_2R'$, C(=O)R', C(=O)OR', $NO_2$, $NH_2$, NHR', $N(R')_2$, NHC(=O)R', CN, halogen, substituted or unsubstituted $C_1$-$C_{25}$ alkyl, substituted or unsubstituted $C_2$-$C_{18}$ alkenyl, substituted or unsubstituted $C_2$-$C_{18}$ alkynyl, substituted or unsubstituted carbocyclic aryl selected from phenyl, naphthyl, biphenyl, phenanthryl and anthracyl, and substituted or unsubstituted heterocyclic selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrrolidinyl;

wherein X is independently selected from OR', CN, (=O), and H;

wherein each of the R' groups is independently selected from the group consisting of H, OH, $NO_2$, $NH_2$, SH, CN, halogen, =O, C(=O)H, C(=O)$CH_3$, $CO_2H$, substituted or unsubstituted $C_1$-$C_{25}$ alkyl, substituted or unsubstituted $C_2$-$C_{18}$ alkenyl, substituted or unsubstituted $C_2$-$C_{18}$ alkynyl, and substituted or unsubstituted carbocyclic aryl selected from phenyl, naphthyl, biphenyl, phenanthryl and anthracyl;

wherein m is 0, 1 or 2; and wherein n is 1, 2, 3 or 4.

2. A compound according to claim 1, wherein:
$R_1$ is hydroxy, halogen, alkyl, alkoxy or aralkyl;
$R_2$ and $R_3$ are each independently selected from hydrogen, C(=O)R', COOR', and optionally substituted alkyl and optionally substituted alkenyl, wherein R' is optionally substituted alkyl or optionally substituted alkenyl and wherein the optional substituents being chosen from halo, amino, amino derived from amino acid, carbocyclic aryl selected from phenyl, naphthyl, biphenyl, phenanthryl and anthracyl, or heterocyclic selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrrolindinyl;

$R_4$ is hydrogen, alkyl, alkenyl or C(=O)OR', where R' is alkenyl;

$R_5$ is hydrogen or alkyl;

X is hydrogen, hydroxy, cyano or (=O);

m is 0 or 1; and n is 1.

3. A compound according to claim 1, wherein $R_1$ is hydroxy, fluorine, methyl, methoxy or benzyloxy, and n is 1.

4. A compound according to claim 1, wherein $R_2$ is hydrogen, acetyl, trifluoromethylcarbonyl, heptafluorobutyryl, 3-chloropropionyl, cinnamoyl, t-butyl-O—CO—, allyl-O—CO— or vinyl-O—CO.

5. A compound according to claim 1 wherein $R_3$ is hydrogen, allyl, $CH_3$—$(CH_2)_n$—CO— where n is 1, 2, 4, 6, 12, 14 or 16; t-butyl-O—CO—, allyl-O—CO— or vinyl-O—CO.

6. A compound according to claim 1 wherein $R_4$ is hydrogen, $C_1$ to $C_3$ alkyl, allyl, or vinyl-O—CO.

7. A compound according to claim 1 wherein $R_5$ is hydrogen or methyl and m is 1.

8. A compound according to claim 1, wherein X is hydroxy.

9. A compound according to claim 1 wherein $R_2$ is not acetyl.

10. A compound according to claim 1 wherein $R_3$ is not hydrogen.

11. A compound according to claim 1 wherein $R_5$ is not hydrogen.

12. A pharmaceutical composition which comprises a compound according to claim 1 together with a pharmaceutically acceptable diluent.

13. A method for the treatment of lung cancer, colon cancer, kidney cancer, prostate cancer, cervical cancer, ovarian cancer, breast cancer, pancreatic cancer, leukaemia or melanoma in a mammal, comprising administering to a mammal in need of such treatment an effective amount of a compound of general formula according to claim 1.

14. A compound according to claim 2, wherein $R_1$ is hydroxy, fluorine, methyl, methoxy or benzyloxy, and n is 1.

15. A compound according to claim 2 wherein $R_2$ is hydrogen, acetyl, trifluoromethylcarbonyl, heptafluorobutyryl, 3-chloropropionyl, cinnamoyl, t-butyl-O—CO—, allyl-O—CO— or vinyl-O—CO.

16. A compound according to claim 2 wherein $R_3$ is hydrogen, allyl, $CH_3$—$(CH_2)_n$—CO— where n is 1, 2, 4, 6, 12, 14 or 16, t-butyl-O—CO—, allyl-O—CO— or vinyl-O—CO—.

17. A compound according to claim 2 wherein $R_4$ is hydrogen, $C_1$ to $C_3$ alkyl, allyl or vinyl-O—CO—.

18. A compound according to claim 2 wherein $R_5$ is hydrogen or methyl and m is 1.

19. A compound according to claim 2 wherein X is hydroxy.

20. A compound according to claim 2 wherein X is cyano.

21. A compound according to claim 1 wherein X is cyano.

22. A compound according to claim 1 of formula:

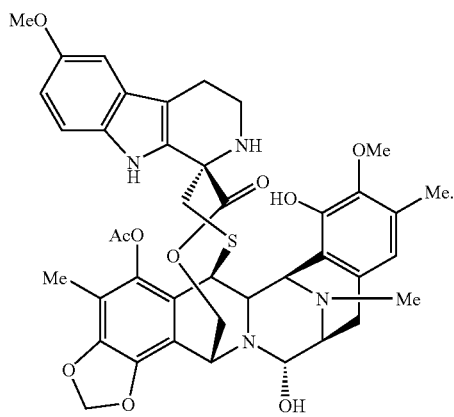

23. A compound according to claim 1 of formula:

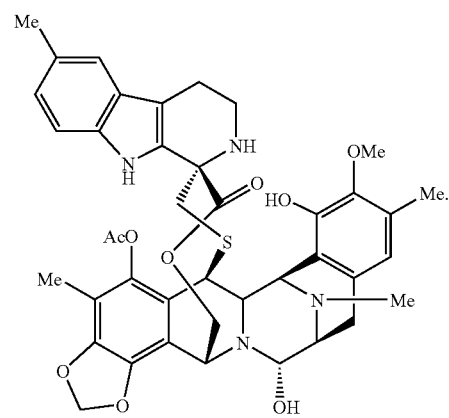

24. A compound according to claim 1 of formula:

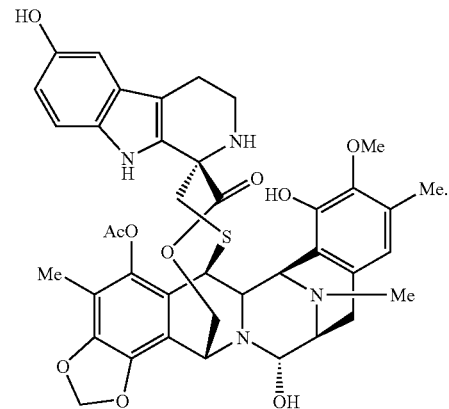

25. A compound according to claim 1 of formula:

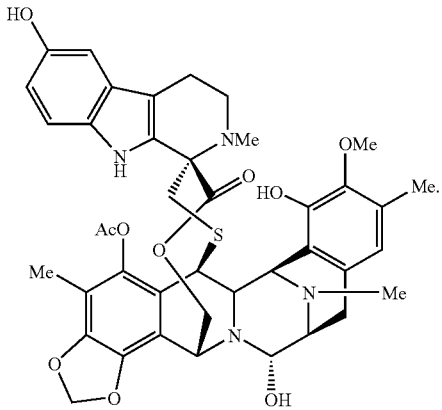

26. A compound according to claim 1 of formula:

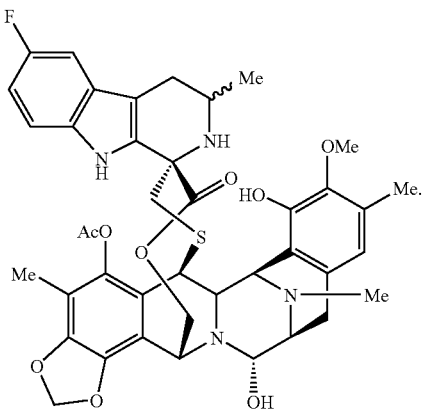

27. A compound according to claim 1 of formula:

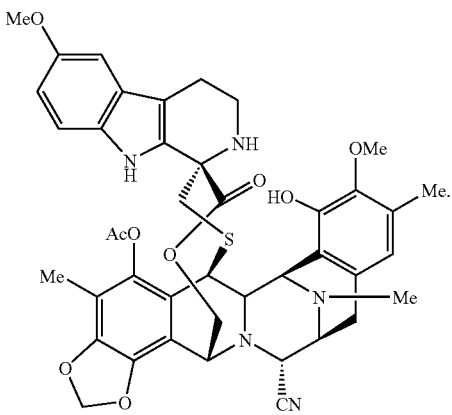

28. A compound according to claim 1 of formula:

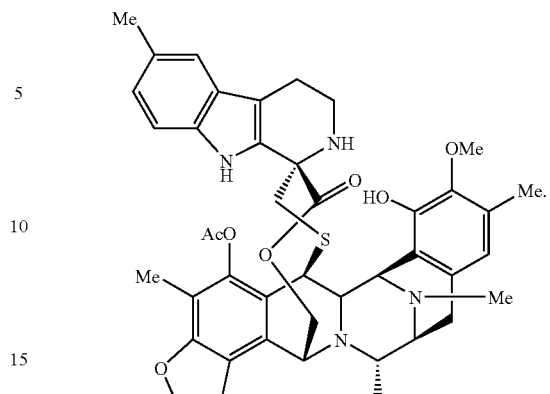

29. A compound according to claim 1 of formula:

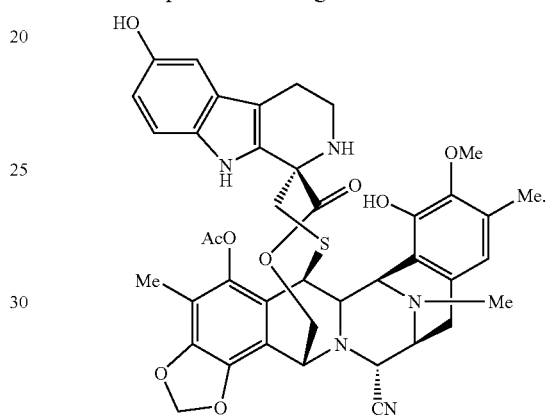

30. A compound according to claim 1 of formula:

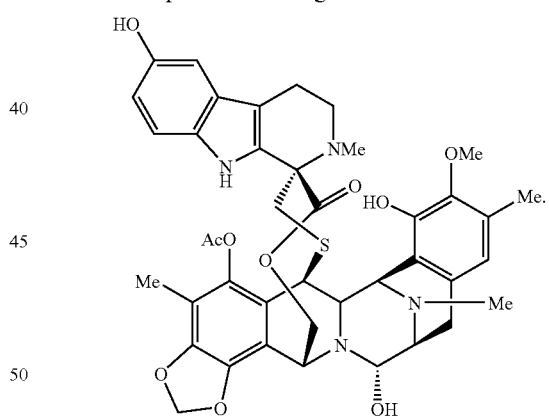

31. A pharmaceutical composition which comprises a compound according to claim 2 together with a pharmaceutically acceptable diluent.

32. A method for the treatment of lung cancer, colon cancer, kidney cancer, prostate cancer, cervical cancer, ovarian cancer, breast cancer, pancreatic cancer, leukaemia or melanoma in a mammal, comprising administering to a mammal in need of such treatment an effective amount of a compound of general formula according to claim 2.

* * * * *

UNITED STATES PATENT AND TRADEMARK OFFICE
CERTIFICATE OF CORRECTION

PATENT NO. : 7,763,615 B2
APPLICATION NO. : 10/485536
DATED : July 27, 2010
INVENTOR(S) : Pilar Gallego et al.

Page 1 of 3

It is certified that error appears in the above-identified patent and that said Letters Patent is hereby corrected as shown below:

In the Claims

Claim 22, Column 66, Lines 5-20, the chemical structure should be as follows:

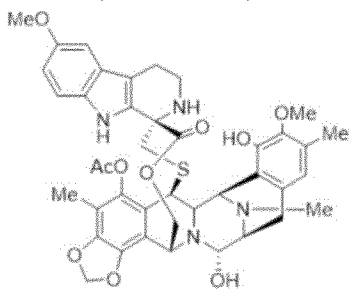

Claim 23, Column 66, Lines 25-45, the chemical structure should be as follows:

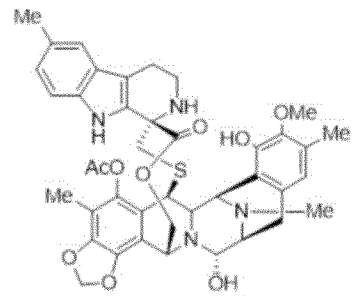

Signed and Sealed this
Twenty-eighth Day of January, 2020

Andrei Iancu
*Director of the United States Patent and Trademark Office*

CERTIFICATE OF CORRECTION (continued)
U.S. Pat. No. 7,763,615 B2

Claim 24, Column 66, Lines 50-65, the chemical structure should be as follows:

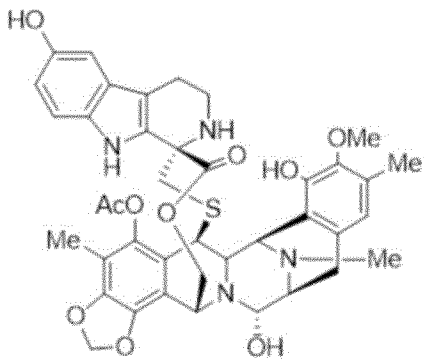

Claim 25, Column 67, Lines 4-20, the chemical structure should be as follows:

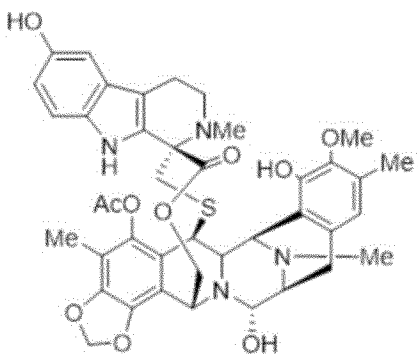

Claim 26, Column 67, Lines 25-40, the chemical structure should be as follows:

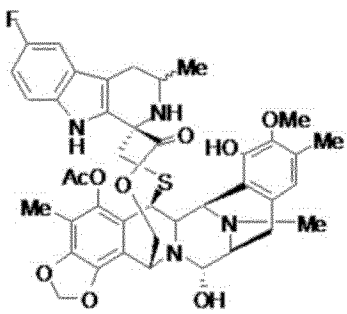

Claim 27, Column 67, Lines 44-60, the chemical structure should be as follows:

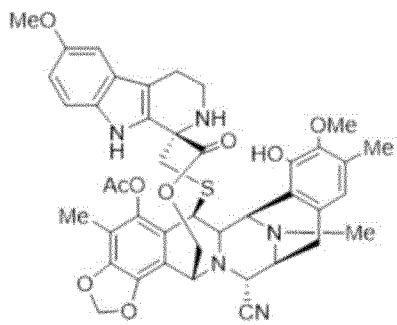

Claim 28, Column 68, Lines 2-17, the chemical structure should be as follows:
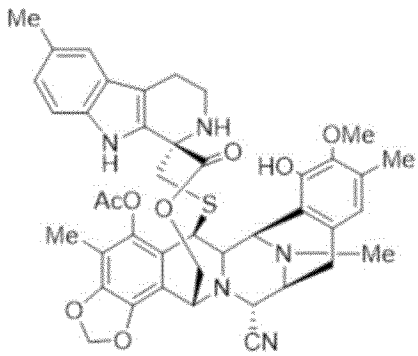
Claim 29, Column 68, Lines 20-34, the chemical structure should be as follows:
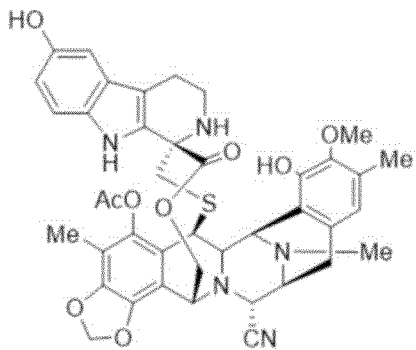
Claim 30, Column 68, Lines 37-52, the chemical structure should be as follows:
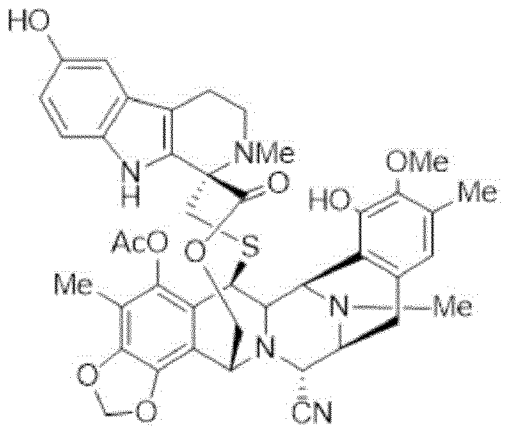

UNITED STATES PATENT AND TRADEMARK OFFICE
CERTIFICATE OF CORRECTION

PATENT NO. : 7,763,615 B2
APPLICATION NO. : 10/485536
DATED : July 27, 2010
INVENTOR(S) : Pilar Gallego et al.

Page 1 of 1

It is certified that error appears in the above-identified patent and that said Letters Patent is hereby corrected as shown below:

In the Specification

Column 26: Line 35, the modular formula "$C_{40}H_{42}N_4O_8S$" should read "$C_{41}H_{44}N_4O_{10}S$"

Signed and Sealed this
Eighth Day of September, 2020

Andrei Iancu
*Director of the United States Patent and Trademark Office*